(12) United States Patent
Liang et al.

(10) Patent No.: US 12,297,206 B2
(45) Date of Patent: May 13, 2025

(54) METHOD FOR SYNTHESIZING FUROIMIDAZOPYRIDINE COMPOUND, POLYMORPHIC SUBSTANCE AND POLYMORPHIC SUBSTANCE OF SALT

(71) Applicant: HANGZHOU HIGHLIGHTLL PHARMACEUTICAL CO., LTD, Zhejiang (CN)

(72) Inventors: Congxin Liang, Jupiter, FL (US); Laibao Wang, Shanghai (CN); Haihui Liu, Shanghai (CN)

(73) Assignee: Biohaven Therapeutics Ltd., Tortola (VG)

( * ) Notice: Subject to any disclaimer, the term of this patent is extended or adjusted under 35 U.S.C. 154(b) by 835 days.

(21) Appl. No.: 17/615,437

(22) PCT Filed: Apr. 30, 2020

(86) PCT No.: PCT/CN2020/088122
§ 371 (c)(1),
(2) Date: Nov. 30, 2021

(87) PCT Pub. No.: WO2020/244349
PCT Pub. Date: Dec. 10, 2020

(65) Prior Publication Data
US 2022/0242873 A1    Aug. 4, 2022

(30) Foreign Application Priority Data
Jun. 6, 2019   (CN) .......................... 201910490711.4

(51) Int. Cl.
*C07D 491/147*    (2006.01)
(52) U.S. Cl.
CPC ...... *C07D 491/147* (2013.01); *C07B 2200/13* (2013.01)

(58) Field of Classification Search
CPC ............. C07D 491/147; C07B 2200/13; Y02P 20/55; A61P 29/00; A61P 35/00;
(Continued)

(56) References Cited

U.S. PATENT DOCUMENTS 9,181,271 B2    11/2015    Li et al.
9,802,957 B2    10/2017    Zhou et al.
(Continued)

FOREIGN PATENT DOCUMENTS

CN     104918945 A    9/2015
CN     106687462 A    5/2017
(Continued)

OTHER PUBLICATIONS

First Office Action for Chinese Patent Application No. 202080037087.3 dated Jun. 15, 2023; 10 pp.
(Continued)

*Primary Examiner* — Alicia L Otton
*Assistant Examiner* — David M Shim

(57) ABSTRACT

A method for synthesizing a compound 2-[(2R,5S)-5-[2-methylfuro[3,2-b]imidazo[4,5-d]pyridin-1-yl]tetrahydropyran-2-yl]acetonitr ile as a selective JAK1/TYK2 kinase inhibitor. The compound is prepared by taking 7-chloro-6-nitrofuro[3,2-b]pyridine as the starting material, and by nucleophilic substitution, palladium on carbon reduction and cyclization reactions. The present synthesis method has mild reaction conditions, high product yield and high purity, and is suitable for industrial production. A crystal form of the compound, crystal forms of the salts thereof and preparation methods thereof. The crystal form of the compound and the crystal forms of the salts thereof have good physical and chemical properties and are suitable for drug development.

3 Claims, 28 Drawing Sheets

(58) Field of Classification Search
CPC ............... A61P 19/02; A61K 31/4155; A61K 31/437; A61K 31/519
See application file for complete search history.

(56) References Cited

U.S. PATENT DOCUMENTS

| | | |
|---|---|---|
| 10,738,060 B2 | 8/2020 | Liang |
| 2018/0099978 A1 | 4/2018 | Zhou et al. |
| 2019/0256523 A1 | 8/2019 | Liang |

FOREIGN PATENT DOCUMENTS

| | | | | |
|---|---|---|---|---|
| CN | 108366994 A | * | 8/2018 | ......... A61K 31/4155 |
| WO | 2014071031 A1 | | 5/2014 | |
| WO | 2015168246 A1 | | 11/2015 | |
| WO | WO 2018/067422 A1 | * | 4/2018 | ......... A61K 31/4155 |

OTHER PUBLICATIONS

International Search Report for International Application No. PCT/CN2020/088122, mailed Jun. 30, 2020, 4 pages.

P. Murray, "The JAK-STAT Signaling Pathway: Input and Output Integration", The Journal of Immunology, vol. 178, No. 5, Mar. 1, 2007, pp. 2623-2629.

Ghoreschi et al., "Janus kinases in immune cell signaling", Immunological Reviews, vol. 228, No. 1, Mar. 2009, pp. 273-287.

Schindler et al., "JAK-STAT signaling: from interferons to cytokines", Journal of Biological Chemistry, vol. 282, No. 28, Jul. 13, 2007, pp. 20059-20063.

Guschin et al. "A major role for the protein tyrosine kinase JAK1 in the JAK/STAT signal transduction pathway in response to interleukin-6", The Embo Journal, vol. 14, No. 7, Apr. 3, 1995, pp. 1421-1429.

Maini et al. "Double-blind randomized controlled clinical trial of the interleukin-6 receptor antagonist, tocilizumab, in European patients with rheumatoid arthritis who had an incomplete response to methotrexate", Arthritis and Rheumatology, vol. 54, No. 9, Sep. 2006, pp. 2817-2829.

Extended European Search Report for Patent Application 20817954.9 dated Feb. 10, 2023; 11 pp.

Caira, Mino R., "Crystalline Polymorphism of Organic Compounds," Current Chemistry, vol. 198, 1998; 46 pp.

First Examination Report for Indian Patent Application No. 202248044451 dated Aug. 26, 2022; 5 pp.

First Examination Report for Patent Application IN 202147056206 mailed Feb. 9, 2022; 7 pp.

Office Action for Russian Patent Application No. 202192871 mailed Dec. 12, 2022; 6 pp.

* cited by examiner

METHOD FOR SYNTHESIZING FUROIMIDAZOPYRIDINE COMPOUND, POLYMORPHIC SUBSTANCE AND POLYMORPHIC SUBSTANCE OF SALT

CROSS-REFERENCE TO RELATED APPLICATIONS

This application is a U.S. National Phase Application of PCT/CN2020/088122, filed on Apr. 30, 2020, which claims the benefit of Chinese Patent Application No. 201910490711.4, filed on Jun. 6, 2019, the contents of which are hereby expressly incorporated by reference in their entirety.

TECHNICAL FIELD

The present invention relates to the field of drug substance synthesis, specifically to the synthesis method of the compound 2-[(2R,5S)-5-[2-methylfuro[3,2-b]imidazo[4,5-d]pyridin-1-yl] tetrahydropyran-2-yl] acetonitrile (hereinafter referred to as compound I or a compound of formula I) as a selective JAK1/TYK2 kinase inhibitor. The present invention also relates to the crystal forms of compound I and its salts and their preparation methods. In addition, the present invention also relates to a pharmaceutical composition and pharmaceutical formulation comprising the crystal form of compound I and/or crystal form of its salts as well as use of crystal forms of compound I and its salts in treating JAK1/TYK2-related diseases and conditions.

BACKGROUND

Protein kinases represent a family of proteins that play an important role in modulating multiple cell processes and maintaining cell functions. These kinases at least include: non-receptor tyrosine kinase, such as Janus kinase family (JAK1, JAK2, JAK3 and TYK2); receptor tyrosine kinase, such as platelet-derived growth factor receptors (PDGFR); and serine/threonine kinase, such as b-RAF.

Janus kinase family includes 4 known family members: JAK1, JAK2, JAK3 and tyrosine kinase 2 (TYK2). These cytoplasmic tyrosine kinases are related to membrane cytokine receptor (such as common γ-chain receptor and glycoprotein 130 (gp130) transmembrane protein) (Murray, *J. Immunol.* 178 (5): 2623-2629, 2007). Almost 40 cytokine receptors transmit signals by the combination of these four JAK family members and their 7 downstream substrates: signal transduction activator of transcription (STAT) family members (Ghoreschi et al., *Immunol Rev.* 228 (1): 273-287, 2009). Cytokine that binds to its receptor activates JAK by trans and/or autophosphorylation. In turn, the activated JAK family kinase phosphorylates a cytokine receptor, generates binding sites for proteins (such as STAT factor and other regulator) containing Src homology 2 (SH2), and JAK phosphorylation then activates them. The activated STAT enters the cell nucleus, starts to promote the expression of survival factors, cytokines, chemokines and molecules of white blood cell transport (Schindler et al., *J. Biol. Chem.* 282(28):20059-20063, 2007). JAK activation also causes cell proliferation by pathways mediated by phosphoinositide-3-kinase (PI3K) and protein kinase B.

JAK3 and JAK1 are components of common γ-chain cytokine receptor compound, and blocking any one of the two can inhibit signal transduction of inflammatory cytokines (interleukin (IL)-2, 4, 7, 9, 15 and 21) (Ghoreschi et al., *Immunol. Rev.* 228 (1): 273-287, 2009). In contrast, other pathologically related cytokines (such as IL-6) only depend on JAK1. Therefore, JAK1 blocking inhibits signal transduction of many proinflammatory cytokines (Guschin et al, EMBO J. 14 (7): 1421-1429, 1995). Clinical efficacy of IL-6 receptor neutralizing antibody—tocilizumab in rheumatoid arthritis (RA) has been observed (Maini et al, *Arthritis Rheum.* 54(9):2817-2829, 2006).

International patent application WO2018067422A1 discloses 1H-furo[3,2-b]imidazo[4,5-d]pyridine derivatives as selective JAK1 kinase inhibitors and their preparation method, including compound I and its preparation method. The synthesis route is as follows:

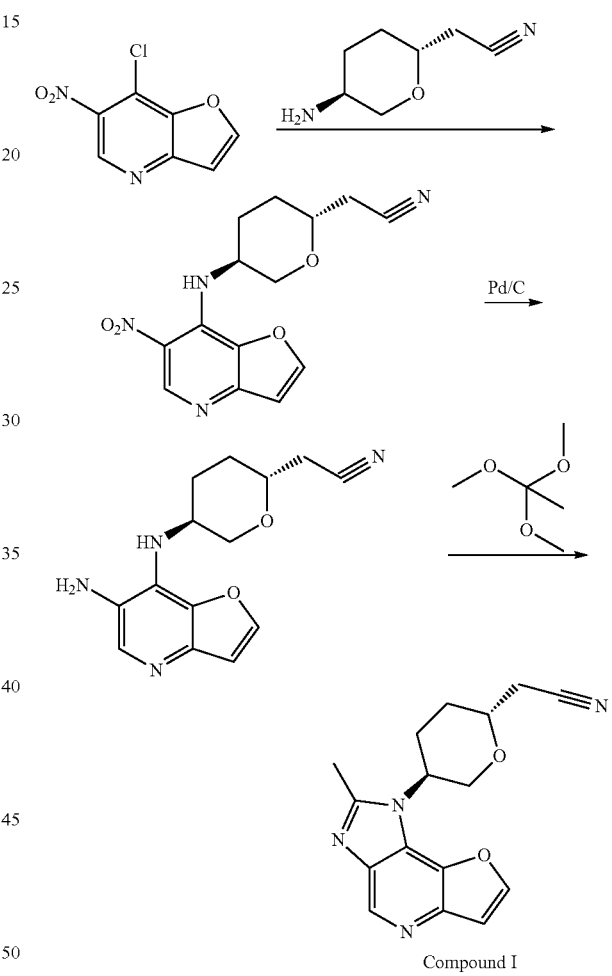

Compound I

Biological tests indicate that compound I is a potent and selective JAK1 inhibitor, demonstrates selective inhibition of IL-6-induced STAT3 phosphorylation and does not show selective inhibition of thrombopoietin-induced STAT3 phosphorylation. However, international patent application WO2018067422A1 doesn't disclose the biological activities of TYK2. In addition, the disclosed preparation method of compound I involves high temperature, produces too many impurities, and has low yield, hereby is not suitable for large scale production. Therefore, it is necessary to develop a preparation method of compound I with milder reaction conditions, higher product yield, higher purity and is suitable for large scale/industrial production.

Currently, there is no report of the crystal form of compound I and its salts. Comprehensive and systematic polymorph screening and the selection of a crystal form that is most suitable for development are one of the indispensable and important research contents. Accordingly, it is necessary to further screen the crystal form of compound I and its salts, develop a crystal form with good stability, low hygroscopicity and is suitable for large scale production and provides more and better choices for subsequent developments of drugs.

SUMMARY

The objective of the present invention is to provide a method for preparing a compound of formula I (that is, compound I) with mild reaction conditions, high product yield and purity and is suitable for industrial production. The synthesis route of the method is as follows:

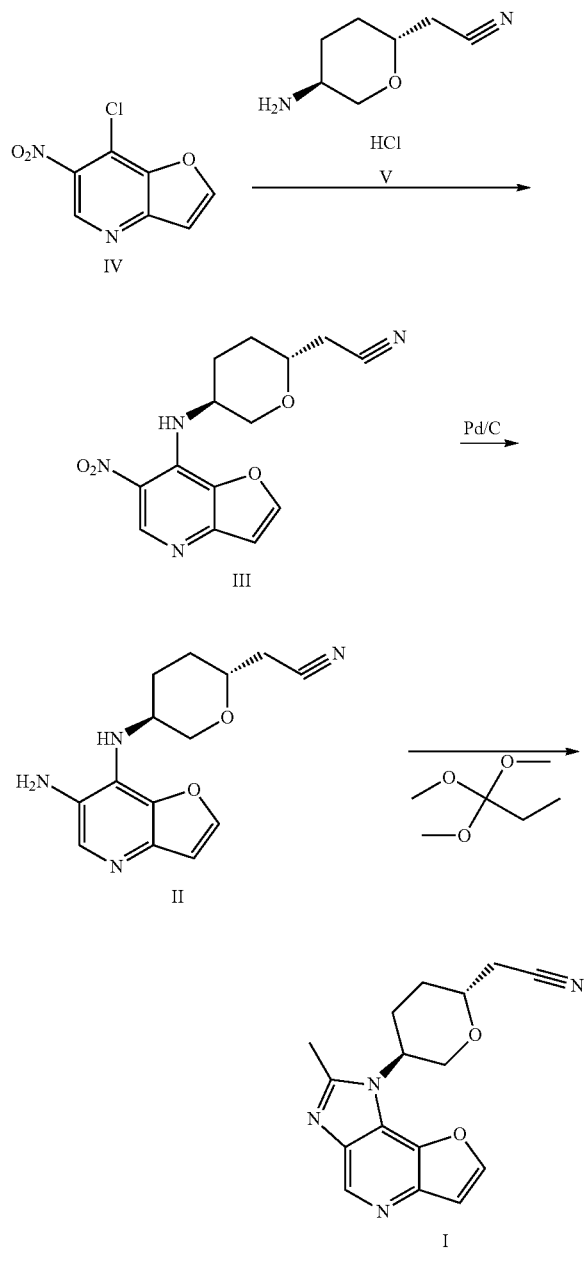

the method comprises the following steps:
step 1:
adding ethanol, a compound of formula IV, a compound of formula V and DIPEA to a reaction container, starting stirring;
heating to raise the temperature to 65-90° C., maintaining the temperature and stirring overnight;
terminating the reaction and lowerring the temperature of the system to 15-30° C.;
adding water to the system dropwise and keeping stirring; filterring and washing the filter cake;
drying the filter cake to obtain a compound of formula III;
step 2:
adding tetrahydrofuran, the compound of formula III obtained in step 1 and palladium on carbon to a reaction container;
purging the system with nitrogen and then hydrogen;
maintaining the temperature between 20-35° C. and stirring for 16-120 hours under 0.1-1.0 MPa hydrogen pressure;
after the reaction is completed, filterring the reaction liquid and washing the filter cake;
combining the filtrate and concentrating to obtain a compound of formula II concentrate;
step 3:
adding the compound of formula II concentrate or the compound of formula II obtained in step 2, and trimethyl orthoacetate and tetrahydrofuran to a reaction container; heating the material system in the reaction container until tetrahydrofuran reflux; adding pyridine hydrochloride to the reaction container, reacting the obtained material system for 4-20 hours at a temperature between 50-90° C., separating and purifying to obtain a compound of formula I.

In some of the embodiments of the above step 1:
the volume mass ratio (mL/g) of ethanol to the compound of formula IV is between 5:1 and 20:1, preferably 10:1;
the molar ratio of the compound of formula IV, the compound of formula V and DIPEA is 1:1-1.1:2-3, preferably 1:1.01:2.2;
after starting stirring, under nitrogen protection, heating to raise the temperature to 65-90° C., preferably 70-90° C., more preferably 70-80° C., maintaining the temperature and stirring for 5-16 hours, preferably 10-16 hours;
after terminating the reaction, lowering the temperature of the system to 15-25° C.;
the volume mass ratio (mL/g) of the water added to the system to the compound of formula IV is between 10:1 and 20:1, preferably 15:1;
after adding water to the system, stirring for 2-6 hours, preferably 4 hours, at a temperature between 0-30° C., preferably 5-15° C., more preferably 5-10° C.;
the filter cake is washed with ethanol aqueous solution, the volume ratio (mL/mL) of ethanol to water in the ethanol aqueous solution is between 1:1 and 1:2, preferably 1:1.5-1:2; the volume mass ratio (mL/g) of the ethanol aqueous solution to the compound of formula IV is between 2:1 and 10:1, preferably 2:1-5:1, more preferably 2:1-3:1;
drying the filter cake under vacuum or with an air blower at a temperature between 45-55° C., preferably 50° C.

In some of the embodiments of the above step 2:
the volume mass ratio (mL/g) of tetrahydrofuran to the compound of formula III is between 10:1 and 70:1, preferably 20:1-70:1;
the palladium on carbon is 5% Pd/C, 50% water wet, the mass ratio (g/g) of the palladium on carbon to the compound of formula III is between 0.15:1 and 0.16:1, preferably 0.15:1;
maintaining the temperature between 25-35° C. and stirring for 24-96 hours under 0.5-1.0 MPa hydrogen pressure;

the compound of formula II concentrate obtained by combining the filtrate and concentrating is a compound of formula II in tetrahydrofuran, wherein the volume mass ratio (mL/g) of the tetrahydrofuran for washing to the compound of formula II is between 2:1 and 4:1, preferably 2:1-3:1 (the mass of the compound of formula II calculated according to a 100% yield of step 2); preferably, exchanging the compound of formula II in tetrahydrofuran with ethanol to obtain a compound of formula II in ethanol, wherein the volume mass ratio (mL/g) of ethanol to the compound of formula II is between 2:1 and 5:1, preferably 2:1-4:1, more preferably 2:1-3:1 (the mass of the compound of formula II calculated according to a 100% yield of step 2).

In some of the embodiments of the above step 3, the volume mass ratio (mL:mg) of tetrahydrofuran to the compound of formula II in the compound of formula II concentrate is between 1.5:1 and 5.0:1; or in some of the embodiments of the above step 3, the volume mass ratio (mL:mg) of tetrahydrofuran to the compound of formula II is between 1.5:1 and 5.0:1.

In some of the embodiments of the above step 3, exchanging the compound of formula II concentrate with toluene, tetrahydrofuran or methyl tertiary-butyl ether for subsequent steps; in some of the embodiments, the volume mass ratio (mL:mg) of toluene, tetrahydrofuran or methyl tertiary-butyl ether used for exchanging to the compound of formula II concentrate is between 2.0:1 and 4.0:1;

in some of the embodiments of the above step 3, the molar ratio of the compound of formula II in the compound of formula II concentrate to trimethyl orthoacetate is between 3.0:1 and 3.5:1; or in some of the embodiments of the above step 3, the molar ratio of the compound of formula II to trimethyl orthoacetate is between 3.0:1 and 3.5:1;

in some of the embodiments of the above step 3, the molar ratio of the compound of formula II in the compound of formula II concentrate to pyridine hydrochloride is between 0.2:1 and 0.3:1; or in some of the embodiments of the above step 3, the molar ratio of the compound of formula II to pyridine hydrochloride is between 0.2:1 and 0.3:1;

in some of the embodiments of the above step 3, after adding the compound of formula II concentrate or the compound of formula II, and trimethyl orthoacetate and the solvent to the reaction container, under nitrogen protection, heating the material system in the reaction container until the solvent reflux;

after adding pyridine hydrochloride to the reactor, under nitrogen protection, reacting the material system for 4-20 hours, preferably 5-15 hours at a temperature between 50-90° C., preferably 65-75° C.;

in some of the embodiments of the above step 3, after the reaction is completed, purifying the product with a solvent selected from the group consisting of water, methanol, ethanol, methyl tertiary-butyl ether and any combinations thereof.

In some of the embodiments of the above step 3, separating and purifying the compound of formula I obtained by column chromatography, wherein the eluent is a mixed solution of ethyl acetate and n-heptane ($V_{EA}:V_{n\text{-}heptane}$=1: 1-1:0, mL/mL);

in some of the embodiments of the above step 3, the obtained compound of formula I is dried under vacuum or with an air blower between 50-55° C.

Another objective of the present invention is to provide a crystal form of a compound of formula I, which is named as crystal form 1 of a compound of formula I hereinafter.

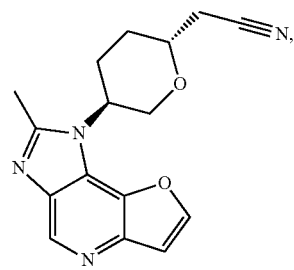

Crystal form 1 of a compound of formula I has an X-ray powder diffraction pattern showing characteristic peaks at 2theta (2θ) angles of 13.4°±0.2°, 17.6°±0.2° and 21.9°±0.2°.

In some embodiments, the X-ray powder diffraction pattern of crystal form 1 of a compound of formula I shows characteristic peaks at 2theta angles of 9.0°±0.2°, 13.4°±0.2°, 17.6°±0.2°, 18.1°±0.2°, 21.9°±0.2° and 27.3°±0.2°.

In some embodiments, the X-ray powder diffraction pattern of crystal form 1 of a compound of formula I shows characteristic peaks at 2theta angles of 9.0°±0.2°, 10.4°±0.2°, 13.4°±0.2°, 17.6°±0.2°, 18.1°±0.2°, 18.7°±0.2°, 21.9°±0.2°, 24.1°±0.2° and 27.3°±0.2°.

Non-restrictively, the X-ray powder diffraction data of crystal form 1 of a compound of formula I of the invention are shown in Table 1.

TABLE 1

| Diffraction angle 2θ (°) | d (Å) | Relative diffraction intensity I% (based on peak height) |
|---|---|---|
| 9.0 | 9.84 | 25.0 |
| 10.4 | 8.51 | 20.9 |
| 13.4 | 6.60 | 63.7 |
| 17.6 | 5.02 | 37.5 |
| 18.1 | 4.91 | 27.3 |
| 18.7 | 4.74 | 20.8 |
| 21.9 | 4.05 | 100.0 |
| 24.1 | 3.69 | 16.4 |
| 27.3 | 3.26 | 25.8 |

Non-restrictively, the X-ray powder diffraction (XRPD) pattern of crystal form 1 of a compound of formula I of the invention is shown in FIG. 1.

Non-restrictively, the differential scanning calorimetry (DSC) thermogram of crystal form 1 of a compound of formula I of the invention is shown in FIG. 2. The DSC thermogram shows that the initial melting point of crystal form 1 of a compound of formula I of the invention is 173.38° C.

Non-restrictively, the thermogravimetic analysis (TGA) thermogram of crystal form 1 of a compound of formula I of the invention is shown in FIG. 3. The TGA thermogram shows that there is only a 0.42% weight loss of crystal form 1 of a compound of formula I of the invention from 25° C. to 162° C. Crystal form 1 of a compound of formula I doesn't contain crystal water or solvent.

Non-restrictively, the dynamic vapour sorption (DVS) isotherm plot of crystal form 1 of a compound of formula I of the invention is shown in FIG. 4. The DVS isotherm plot shows a 13.86% weight gain of crystal form 1 of a compound of formula I of the invention by moisture absorption from 0% RH to 95% RH, indicating that the sample is hygroscopic. The moisture absorption curve during desorption exhibited hysteresis, combining with XRPD pattern of the sample before and after the DVS test (see FIG. 5 for the XRPD pattern after the test), show that after moisture absorption of crystal form 1 of a compound of formula I, the crystal form changes.

The present invention provides a preparation method of crystal form 1 of a compound of formula I, specifically, the method is described as follows:

dissolving a compound of formula I crude product with methanol, stirring between 40-60° C. for 0.5-2 hours, cooling to 5-15° C., stirring for 15 minutes-1 hour, filterring, washing the filter cake with MTBE, and drying to obtain crystal form 1 of a compound of formula I.

In some embodiments, after dissolving the compound of formula I crude product with methanol, stirring at 50° C. for 1 hour, cooling to 10° C., stirring for 0.5 hour, filterring, washing the filter cake with MTBE, and drying the filter cake under vacuum at 50° C. for 16 hours to obtain crystal form 1 of a compound of formula I.

In some embodiments, the volume ratio of methanol to MTBE is between 3:1-2:1, preferably 8:3;

In some embodiments, after dissolving the compound of formula I crude product with methanol, adding a silicon-based metal eliminator and an activated carbon to the system.\

Another objective of the present invention is to provide crystal forms of a compound of formula I, specifically, a crystal form of a hydrochloride, a crystal form of a sulfate, a crystal form of a phosphate, a crystal form of a mesylate, a crystal form of a hydrobromide, a crystal form of a fumarate, a crystal form of a benzene sulfonate, a crystal form of a citrate, a crystal form of a L-(+)-tartrate (which is named as tartrate for short in the present application) of a compound of formula I, they are named as crystal form A of a hydrochloride, crystal form B of a hydrlchloride, crystal form C of a hydrochloride, crystal form D of a sulfate, crystal form E of a phosphate, crystal form F of a phosphate, crystal form G of a mesylate, crystal form H of a hydrobromide, crystal form J of a hydrobromide, crystal form K of a hydrobromide, crystal form L of a fumarate, crystal form M of a benzene sulfonate, crystal form N of a citrate, crystal form O of a tartrate of a compound of formula I respectively hereinafter.

Crystal form A of a hydrochloride of a compound of formula I of the present invention has an X-ray powder diffraction pattern showing characteristic peaks at 2theta angles of 7.3°±0.2°, 12.1°±0.2° and 20.9°±0.2°.

In some embodiments, the X-ray powder diffraction pattern of crystal form A of a hydrochloride of a compound of formula I shows characteristic peaks at 2theta angles of 7.3°±0.2°, 12.1°±0.2°, 18.7°±0.2°, 20.9°±0.2°, 23.5°±0.2° and 24.0°±0.2°.

In some embodiments, the X-ray powder diffraction pattern of crystal form A of a hydrochloride of a compound of formula I shows characteristic peaks at 2theta angles of 7.3°±0.2°, 10.6°±0.2°, 12.1°±0.2°, 12.8°±0.2°, 14.0°±0.2°, 18.7°±0.2°, 20.9°±0.2°, 23.5°±0.2° and 24.0°±0.2°.

Non-restrictively, the X-ray powder diffraction data of crystal form A of a hydrochloride of a compound of formula I of the invention are shown in Table 2.

TABLE 2

| Diffraction angle 2θ (°) | d (A) | Relative diffraction intensity I% (based on peak height) |
|---|---|---|
| 7.3 | 12.12 | 91.5 |
| 10.6 | 8.30 | 30.4 |
| 12.1 | 7.29 | 91.2 |

TABLE 2-continued

| Diffraction angle 2θ (°) | d (A) | Relative diffraction intensity I% (based on peak height) |
|---|---|---|
| 12.8 | 6.92 | 31.1 |
| 14.0 | 6.32 | 22.5 |
| 18.7 | 4.73 | 41.0 |
| 20.9 | 4.24 | 100.0 |
| 23.5 | 3.79 | 40.9 |
| 24.0 | 3.70 | 42.3 |

Non-restrictively, the XRPD pattern of crystal form A of a hydrochloride of a compound of formula I of the invention is shown in FIG. 6.

Non-restrictively, the DSC thermogram of crystal form A of a hydrochloride of a compound of formula I of the invention is shown in FIG. 7.

The present invention provides a preparation method of the crystal form A of a hydrochloride of a compound of formula I, specifically, the method is described as follows:

dissolving a compound of formula I with acetone to obtain a compound of formula I in acetone, and adding hydrochloric acid in acetone to the compound of formula I in acetone under stirring, keeping stirring, collecting the solid, and drying to obtain crystal form A of a hydrochloride of a compound of formula I.

In some embodiments, the compound of formula I is subjected to ultrasonication, heating and then is dissolved in acetone;

In some embodiments, the concentration of the compound of formula I in acetone is 10-50 mg/mL, preferably 20 mg/mL;

In some embodiments, the concentration of the hydrochloric acid in acetone is 15-35 mg/mL, preferably 25 mg/mL;

In some embodiments, after adding the hydrochloric acid in acetone, keeping stirring at a room temperature for 4-48 hours, preferably 24 hours;

In some embodiments, collecting the solid by centrifugation and drying overnight under vacuum at 30-60° C.

Crystal form B of a hydrochloride of a compound of formula I of the present invention has an X-ray powder diffraction pattern showing characteristic peaks at 2theta angles of 7.2°±0.2°, 20.0°±0.2° and 22.6°±0.2°.

In some embodiments, the X-ray powder diffraction pattern of the crystal form B of a hydrochloride of a compound of formula I shows characteristic peaks at 2theta angles of 7.2°±0.2°, 10.2°±0.2°, 11.5°±0.2°, 18.0°±0.2°, 20.0°±0.2°, 22.6°±0.2° and 25.9°±0.2°.

In some embodiments, the X-ray powder diffraction pattern of the crystal form B of a hydrochloride of a compound of formula I shows characteristic peaks at 2theta angles of 7.2°±0.2°, 10.2°±0.2°, 11.5°±0.2°, 14.1°±0.2°, 14.5°±0.2°, 18.0°±0.2°, 20.0°±0.2°, 22.6°±0.2° and 25.9°±0.2°.

Non-restrictively, the X-ray powder diffraction data of crystal form B of a hydrochloride of a compound of formula I of the invention are shown in Table 3:

TABLE 3

| Diffraction angle 2θ (°) | d (A) | Relative diffraction intensity I% (based on peak height) |
|---|---|---|
| 7.2 | 12.26 | 100.0 |
| 10.2 | 8.62 | 41.7 |
| 11.5 | 7.72 | 41.5 |

TABLE 3-continued

| Diffraction angle 2θ (°) | d (A) | Relative diffraction intensity I% (based on peak height) |
|---|---|---|
| 14.1 | 6.29 | 35.3 |
| 14.5 | 6.09 | 25.6 |
| 18.0 | 4.93 | 48.9 |
| 20.0 | 4.44 | 69.9 |
| 22.6 | 3.93 | 62.3 |
| 25.9 | 3.43 | 41.8 |

Non-restrictively, the XRPD pattern of crystal form B of a hydrochloride of a compound of formula I of the invention is shown in FIG. 8.

Non-restrictively, the DSC thermogramthermogram of crystal form B of a hydrochloride of a compound of formula I of the invention is shown in FIG. 9.

The present invention provides a preparation method of crystal form B of a hydrochloride of a compound of formula I, specifically, the method is described as follows:

dissolving a compound of formula I with ethyl acetate to obtain a compound of formula I in ethyl acetate, and adding hydrochloric acid in ethyl acetate to the compound of formula I in ethyl acetate under stirring, keeping stirring, collecting the solid, and drying to obtain crystal form B of a hydrochloride of a compound of formula I.

In some embodiments, the compound of formula I is subjected to ultrasonication, heating and is then dissolved in ethyl acetate;

In some embodiments, the concentration of the compound of formula I in ethyl acetate is 10-30 mg/mL, preferably 20 mg/mL;

In some embodiments, the concentration of the hydrochloric acid in ethyl acetate is 15-35 mg/mL, preferably 25 mg/mL;

In some embodiments, after adding the hydrochloric acid in ethyl acetate, keeping stirring at room temperature for 4-48 hours, preferably 24 hours;

In some embodiments, collecting the solid by centrifugation and drying overnight under vacuum at 30-60° C.

Crystal form C of a hydrochloride of a compound of formula I of the present invention has an X-ray powder diffraction pattern showing characteristic peaks at 2theta angles of 10.7°±0.2°, 21.5°±0.2° and 24.3°±0.2°.

In some embodiments, the X-ray powder diffraction pattern of the crystal form C of a hydrochloride of a compound of formula I shows characteristic peaks at 2theta angles of 5.3°±0.2°, 10.7°±0.2°, 21.5°±0.2°, 24.3°±0.2°, and 30.4°±0.2°.

Non-restrictively, the X-ray powder diffraction data of crystal form C of a hydrochloride of a compound of formula I of the invention are shown in Table 4:

TABLE 4

| Diffraction angle 2θ (°) | d (A) | Relative diffraction intensity I% (based on peak height) |
|---|---|---|
| 5.3 | 16.5427 | 10.1 |
| 10.7 | 8.2756 | 100.0 |
| 21.5 | 4.1379 | 52.3 |
| 24.3 | 3.6532 | 20.1 |
| 30.4 | 2.9351 | 15.8 |

Non-restrictively, the XRPD pattern of crystal form C of a hydrochloride of a compound of formula I of the invention is shown in FIG. 10.

Non-restrictively, the DSC thermogram of crystal form C of a hydrochloride of a compound of formula I of the invention is shown in FIG. 11.

Conducting recrystallization or crystal transformation of crystal form A of a hydrochloride of a compound of formula I with a solvent to obtain crystal form C of a hydrochloride of a compound of formula I, wherein the solvent is selected from of the group consisting of methanol, acetonitrile, n-heptane, methyl ethyl ketone and any combinations thereof.

In some embodiments, mixing the solvent with crystal form A of a hydrochloride of a compound of formula I to prepare suspension, stirring at room temperature, collecting the solid, and drying to obtain crystal form C of a hydrochloride of a compound of formula I.

In some embodiments, adding the solvent to a container with crystal form A of a hydrochloride of a compound of formula Ito prepare suspension, stirring at room temperature, collecting the solid, and drying to obtain crystal form C of a hydrlcholride of a compound of formula I.

In some embodiments, the duration of the stirring is 4-48 hours, preferably 24 hours.

In some embodiments, collecting the solid by centrifugation and drying overnight under vacuum at 30-60° C.

Crystal form D of a sulfate of a compound of formula I of the presenti invention has an X-ray power diffraction pattern showing characteristic peaks at 2theta angles of 6.0°±0.2°, 22.8°±0.2° and 25.2°±0.2°.

In some embodiments, the X-ray powder diffraction pattern of the crystal form D of a sulfate of a compound of formula I shows characteristic peaks at 2theta angles of 6.0°±0.2°, 12.3°±0.2°, 17.5°±0.2°, 22.8°±0.2°, and 25.2°±0.2°.

Non-restrictively, the X-ray powder diffraction data of crystal form D of a sulfate of a compound of formula I of the invention are shown in Table 5:

TABLE 5

| Diffraction angle 2Θ (°) | d (A) | Relative diffraction intensity I% (based on peak height) |
|---|---|---|
| 6.0 | 14.59 | 100.0 |
| 12.3 | 7.19 | 12.0 |
| 17.5 | 5.06 | 9.0 |
| 22.8 | 3.90 | 36.3 |
| 25.0 | 3.53 | 17.1 |

Non-restrictively, the XRPD pattern of crystal form D of a sulfate of a compound of formula I of the invention is shown in FIG. 12.

Non-restrictively, the DSC thermogram of crystal form D of a sulfate of a compound of formula I of the invention is shown in FIG. 13.

The present invention provides a preparation method of crystal form D of a sulfate of a compound of formula I, specifically, the method is described as follows:

dissolving a compound of formula I with acetone to obtaina compound of formula I in acetone, and adding sulfuric acid in acetone to the compound of formula I in acetone under stirring, keeping stirring, collecting the solid, and drying to obtain crystal form D of a sulfate of a compound of formula I.

In some embodiments, the compound of formula I is subjected to ultrasonication, heating and is then dissolved in acetone.

In some embodiments, the concentration of the compound of formula I in acetone is 10-30 mg/mL, preferably 20 mg/mL.

In some embodiments, the concentration of the sulfuric acid in acetone is 15-35 mg/mL, preferably 25 mg/mL.

In some embodiments, after adding sulfuric acid in acetone, keeping stirring at room temperature for 4-48 hours, preferably 24 hours.

In some embodiments, collecting the solid by centrifugation and drying overnight under vacuum at 30-60° C.

Crystal form E of a phosphate of a compound of formula I of the present invention has an X-ray power diffraction pattern showing characteristic peaks at 2theta angles of 6.2°±0.2°, 15.5°±0.2°, 17.4°±0.2° and 24.6°±0.2°.

Non-restrictively, the X-ray powder diffraction data of crystal form E of a phosphate of a compound of formula I of the invention are shown in Table 6:

TABLE 6

| Diffraction angle 2θ (°) | d (A) | Relative diffraction intensity I% (based on peak height) |
|---|---|---|
| 6.2 | 14.24 | 100.0 |
| 15.5 | 5.70 | 22.4 |
| 17.4 | 5.09 | 16.9 |
| 24.6 | 3.62 | 16.1 |

Non-restrictively, the XRPD pattern of crystal form E of a phosphate of a compound of formula I of the invention is shown in FIG. 14.

Non-restrictively, the DSC thermogramthermogram of crystal form E of a phosphate of a compound of formula I of the invention is shown in FIG. 15.

The present invention provides a preparation method of crystal form E of a phosphate of a compound of formula I, specifically, the method is described as follows:

dissolving a compound of formula I with acetone to obtain a compound of formula I in acetone, and adding phosphoric acid in acetone to the compound of formula I in acetone under stirring, keeping stirring, collecting the solid, and drying to obtain crystal form E of a phosphate of a compound of formula I.

In some embodiments, the compound of formula I is subjected to ultrasonication, heating and is then dissolved in acetone.

In some embodiments, the molar ratio of the compound of formula I to phosphoric acid is between 1:1.0-1:1.5.

In some embodiments, the concentration of the compound of formula I in acetone is 10-30 mg/mL, preferably 20 mg/mL.

In some embodiments, the concentration of the phosphoric acid in acetone is 15-35 mg/mL, preferably 25 mg/mL.

In some embodiments, after adding the phosphoric acid in acetone, keeping stirring at room temperature for 4-48 hours, preferably 24 hours.

In some embodiments, collecting the solid by centrifugation and drying overnight under vacuum at 30-60° C.

In some embodiments, conducting recrystallization or crystal transformation of crystal form E of a phosphate of a compound of formula I with a solvent, and the product is still crystal form E of a phosphate of a compound of formula I, wherein the solvent is selected from the group consisting of methanol, acetonitrile, n-heptane, methyl ethyl ketone and any combinations thereof.

In some embodiments, during recrystallization or crystal transformation, mixing the solvent and crystal form E of a phosphate of a compound of formula Ito prepare suspension, stirring at room temperature, collecting the solid, and drying.

In some embodiments, during recrystallization or crystal transformation, the duration of the stirring is between 4-48 hours, preferably stirring overnight;

In some embodiments, during recrystallization or crystal transformation, collecting the solid by centrifugation and drying overnight under vacuum at 30-60° C.

Crystal form F of a phosphate of a compound of formula I of the present inveniton has an X-ray power diffraction pattern showing characteristic peaks at 2theta angles of 16.6°±0.2°, 17.2°±0.2° and 22.6°±0.2°.

In some embodiments, the X-ray powder diffraction pattern of the crystal form F of a phosphate of a compound of formula I shows characteristic peaks at 2theta angles of 11.6°±0.2°, 14.8°±0.2°, 16.6°±0.2°, 17.2°±0.2°, 22.6°±0.2° and 26.6°±0.2°.

In some embodiments, the X-ray powder diffraction pattern of the crystal form F of a phosphate of a compound of formula I shows characteristic peaks at 2theta angles of 11.1°±0.2°, 11.6°±0.2°, 14.8°±0.2°, 16.6°±0.2°, 17.2°±0.2°, 21.2°±0.2°, 22.6°±0.2° and 26.6°±0.2°.

Non-restrictively, the X-ray powder diffraction data of crystal form F of a phosphate of a compound of formula I of the invention are shown in Table 7:

TABLE 7

| Diffraction angle 2θ (°) | d (A) | Relative diffraction intensity I% (based on peak height) |
|---|---|---|
| 11.1 | 7.97 | 15.9 |
| 11.6 | 7.65 | 35.0 |
| 14.8 | 5.97 | 32.4 |
| 16.6 | 5.33 | 69.7 |
| 17.2 | 5.16 | 49.1 |
| 21.2 | 4.19 | 25.3 |
| 22.6 | 3.93 | 100.0 |
| 26.6 | 3.34 | 31.9 |

Non-restrictively, the XRPD pattern of crystal form F of a phosphate of a compound of formula I of the invention is shown in FIG. 16.

Non-restrictively, the DSC thermogramthermogram of crystal form F of a phosphate of a compound of formula I of the invention is shown in FIG. 17. The DSC thermogramthermogram shows that the initial melting point of crystal form F of a phosphate of a compound of formula I of the invention is 198.78° C.

Non-restrictively, the DVS isotherm plot of crystal form F of a phosphate of a compound of formula I of the invention is shown in FIG. 18. The DVS isotherm plotisotherm plot shows a 6.5% weight gain of crystal form F of a phosphate of a compound of formula I of the invention by moisture absorption from 0% RH to 95% RH. At a humidity of 85% RH, crystal form F of a phosphate of a compound of formula I reaches a weight gain of 0.72%; at 70% RH, crystal form F of a phosphate of a compound of formula I reaches a weight gain of 1.95%. After the moisture absorption, crystal form F of a phosphate of a compound of formula I doesn't change (see FIG. 19 for the XRPD pattern after the moisture absorption).

The present invention provides a preparation method of crystal form F of a phosphate of a compound of formula I, specifically, the method is described as follows:

dissolving crystal form E of a phosphate of a compound of formula I with a first solvent to obtain crystal form E of a phosphate of a compound of formula I in the first solvent, adding an anti-solvent, stirring, collecting the solid, and drying to obtain crystal form F of a phosphate of a compound of formula I; or in some embodiments, the first solvent is a solvent that can dissolve crystal form E of a phosphate of a compound of formula I, preferably methanol; the anti-solvent is a solvent that is difficult to dissolve crystal form E of a phosphate of a compound of formula I, preferably isopropyl acetate.

In some embodiments, the first solvent is added in an amount that can completely dissolve crystal form E of a phosphate of a compound of formula I.

In some embodiments, the anti-solvent is used to dilute crystal form E of a phosphate of a compound of formula I in the first solvent at 5-15 folds, preferably 10 folds.

In some embodiments, after dissolving crystal form E of a phosphate of a compound of formula I with the first solvent, adding a smally amount of seed crystals of crystal form F of a phosphate of a compound of formula I until the system is slightly turbid, then adding the anti-solvent.

In some embodiments, after adding the anti-solvent, keeping stirring at room temperature for 4-48 hours, preferably 24 hours.

In some embodiments, collecting the solid by centrifugation and drying under vacuum between 30-60° C., preferably 50° C.

Crystal form G of a mesylate of a compound of formula I of the present invention has an X-ray powder diffraction pattern showing characteristic peaks at 2theta angles of 8.6°±0.2°, 19.9°±0.2° and 24.9°±0.2°.

In some embodiments, the X-ray powder diffraction pattern of the crystal form G of a mesylate of a compound of formula I shows characteristic peaks at 2theta angles of 8.6°±0.2°, 18.1°±0.2°, 18.6°±0.2°, 19.9°±0.2°, 24.0°±0.2° and 24.9°±0.2°.

Non-restrictively, the X-ray powder diffraction data of crystal form G of a mesylate of a compound of formula I of the invention are shown in Table 8.

TABLE 8

| Diffraction angle 2θ (°) | d (A) | Relative diffraction intensity I% (based on peak height) |
|---|---|---|
| 8.6 | 10.32 | 100.0 |
| 18.1 | 4.88 | 56.9 |
| 18.6 | 4.76 | 62.7 |
| 19.9 | 4.456 | 87.1 |
| 24.0 | 3.71 | 23.0 |
| 25.0 | 3.57 | 76.1 |

Non-restrictively, the XRPD pattern of a crystal form G of a mesylate of a compound of formula I of the invention is shown in FIG. 20.

Non-restrictively, the DSC thermogram of crystal form G of a mesylate of a compound of formula I of the invention is shown in FIG. 21. The DSC thermogramthermogram shows that the initial melting point of crystal form G of a mesylate of a compound of formula I of the invention is 218.78° C.

Non-restrictively, the DVS isotherm plotisotherm plot of crystal form G of a mesylate of a compound of formula I of the invention is shown in FIG. 22.

The present invention provides a preparation method of crystal form G of a mesylate of a compound of formula I, specifically, the method is described as follows:

dissolving a compound of formula I with acetone to obtain a compound of formula I in acetone, and adding methylsulfonic acid in acetone to the compound of formula I in acetone under stirring, keeping stirring, collecting the solid, and drying to obtain crystal form G of a mesylate of a compound of formula I.

In some embodiments, the compound of formula I is subjected to ultrasonication, heating and is then dissolved in acetone.

In some embodiments, the concentration of the compound of formula I in acetone is 10-30 mg/mL, preferably 20 mg/mL.

In some embodiments, the concentration of the methanesulfonic acid in acetone is 15-35 mg/mL, preferably 25 mg/mL.

In some embodiments, after adding the methanesulfonic acid in acetone, keeping stirring at room temperature for 4-48 hours, preferably 24 hours.

In some embodiments, collecting the solid by centrifugation and drying overnight under vacuum at 30-60° C.

Crystal form H of a hydrobromide of a compound of formula I of the present invention has an X-ray powder diffraction pattern showing characteristic peaks at 2theta angles of 7.2°±0.2°, 20.7°±0.2° and 24.0°±0.2°.

In some embodiments, the X-ray powder diffraction pattern of the crystal form H of a hydrobromide of a compound of formula I shows characteristic peaks at 2theta angles of 7.2°±0.2°, 17.9°±0.2°, 18.8°±0.2°, 20.7°±0.2° and 24.0°±0.2°.

In some embodiments, the X-ray powder diffraction pattern of the crystal form H of a hydrobromide of a compound of formula I shows characteristic peaks at 2theta angles of 7.2°±0.2°, 11.9°±0.2°, 17.0°±0.2°, 17.9°±0.2°, 18.8°±0.2°, 20.7°±0.2°, 24.0°±0.2° and 27.5°±0.2°.

Non-restrictively, the X-ray powder diffraction data of crystal form H of a hydrobromide of a compound of formula I of the invention are shown in Table 9.

TABLE 9

| Diffraction angle 2θ (°) | d (A) | Relative diffraction intensity I% (based on peak height) |
|---|---|---|
| 7.2 | 12.34 | 100.0 |
| 11.9 | 7.40 | 22.1 |
| 17.0 | 5.21 | 29.1 |
| 17.9 | 4.94 | 50.0 |
| 18.8 | 4.73 | 45.7 |
| 20.7 | 4.28 | 73.1 |
| 24.0 | 3.70 | 57.3 |
| 27.5 | 3.24 | 18.9 |

Non-restrictively, the XRPD pattern of crystal form H of a hydrobromide of a compound of formula I of the invention is shown in FIG. 23.

Non-restrictively, the DSC thermogram of crystal form H of a hydrobromide of a compound of formula I of the invention is shown in FIG. 24.

The present invention provides a preparation method of crystal form H of a hydrobromide of a compound of formula I, specifically, the method is described as follows:

dissolving a compound of formula I with acetone to obtain a compound of formula I in acetone, and adding hydrobromic acid in acetone to the compound of formula I in acetone under stirring, keeping stirring, collecting the solid, and drying to obtain crystal form H of a hydrobromide of a compound of formula I.

In some embodiments, the compound of formula I is subjected to ultrasonication, heating and is then dissolved in acetone.

In some embodiments, the concentration of the compound of formula I in acetone is 10-30 mg/mL, preferably 20 mg/mL.

In some embodiments, the concentration of the hydrobromic acid in acetone is 15-35 mg/mL, preferably 25 mg/mL.

In some embodiments, after adding the hydrobromic acid in acetone, keeping stirring at room temperature for 4-48 hours, preferably 24 hour.

In some embodiments, collecting the solid by centrifugation and drying under vacuum overnight at 30-60° C.

In some embodiments, conducting recrystallization or crystal transformation of crystal form H of a hydrobromide of a compound of formula I with a solvent, and the product is still crystal form H of a hydrobromide, wherein the solvent is selecte from the group consisting of acetonitrile, methyl ethyl ketone and any combinations thereof.

In some embodiments, the recrystallization or crystal transformation comprises the following steps:

mixing one or both of acetonitrile and methyl ethyl ketone with crystal form H of a hydrobromide of a compound of formula I, to prepare suspension, stirring at room temperature, centrifuging, collecting the solid and drying;

preferably, adding one or both of acetonitrile and methyl ethyl ketone to a container with crystal form H of a hydrobromide of a compound of formula I, to prepare suspension, stirring at room temperature, centrifuging, collecting the solid and drying.

Crystal form J of a hydrobromide of a compound of formula I of the present invention has an X-ray powder diffraction pattern showing characteristic peaks at 2theta angles of 6.2°±0.2° and 15.0°±0.2°.

Non-restrictively, the X-ray powder diffraction data of crystal form J of a hydrobromide of a compound of formula I of the invention are shown in Table 10.

TABLE 10

| Diffraction angle 2θ (°) | d (A) | Relative diffraction intensity I% (based on peak height) |
| --- | --- | --- |
| 6.2 | 14.23 | 51.2 |
| 15.0 | 5.88 | 43.0 |

Non-restrictively, the XRPD pattern of crystal form J of a hydrobromide of a compound of formula I of the invention is shown in FIG. 25.

The present invention provides a preparation method of crystal form J of a hydrobromide of a compound of formula I, specifically, the method is described as follows:

dissolving a compound of formula I with ethyl acetate to obtain a compound of formula I in ethyl acetate, and adding hydrobromic acid in ethyl acetate to the compounf of formula I in ethyl acetate under stirring, keeping stirring, collecting the solid, and dringy to obtain crystal form J of a hydrobromide of a compound of formula I.

In some embodiments, the compound of formula I is subjected to ultrasonication, heating and is then dissolved in ethyl acetate.

In some embodiments, the concentration of the compound of formula I in ethyl acetate is 10-30 mg/mL, preferably 20 mg/mL.

In some embodiments, the concentration of the hydrobromic acid in ethyl acetate is 15-35 mg/mL, preferably 25 mg/mL.

In some embodiments, after adding the hydrobromic acid in ethyl acetate, keeping stirring at room temperature for 4-48 hours, preferably 24 hours;

In some embodiments, collecting the solid by centrifugation and drying overnight under vacuum at 30-60° C.

Crystal form K of a hydrobromide of a compound of formula I of the present invention has an X-ray powder diffraction pattern showing characteristic peaks at 2theta angles of 17.1°±0.2°, 22.0°±0.2° and 24.2°±0.2°.

The X-ray powder diffraction pattern of the crystal form K of a hydrobromide of a compound of formula I shows characteristic peaks at 2theta angles of 17.1°±0.2°, 20.1°±0.2°, 22.0°±0.2°, 22.6°±0.2°, 24.2°±0.2° and 28.8°±0.2°.

The X-ray powder diffraction pattern of the crystal form K of a hydrobromide of a compound of formula I shows characteristic peaks at 2theta angles of 9.5°±0.2°, 17.1°±0.2°, 20.1°±0.2°, 22.0°±0.2°, 22.6°±0.2°, 24.2°±0.2°, 27.7°±0.2° and 28.8°±0.2°.

Non-restrictively, the X-ray powder diffraction data of crystal form K of a hydrobromide of a compound of formula I of the invention are shown in Table 11:

TABLE 11

| Diffraction angle 2θ (°) | d (A) | Relative diffraction intensity I% (based on peak height) |
| --- | --- | --- |
| 9.5 | 9.26 | 23.3 |
| 17.1 | 5.19 | 55.6 |
| 20.1 | 4.40 | 33.9 |
| 22.0 | 4.04 | 100.0 |
| 22.6 | 3.94 | 31.1 |
| 23.6 | 3.76 | 30.6 |
| 24.2 | 3.67 | 36.7 |
| 27.7 | 3.21 | 19.3 |
| 28.8 | 3.10 | 32.9 |

Non-restrictively, the XRPD pattern of crystal form K of a hydrobromide of a compound of formula I of the invention is shown in FIG. 26.

Non-restrictively, the DSC thermogramthermogram of crystal form K of a hydrobromide of a compound of formula I of the invention is shown in FIG. 27.

Non-restrictively, the DVS isotherm plotisothermo plot of crystal form K of a hydrobromide of a compound of formula I of the invention is shown in FIG. 28. The DVS isothermo plot shows a 11.84% weight gain of crystal form K of a hydrobromide of a compound of formula I of the invention by moisture absorption from 0% RH to 95% RH, indicating that the sample is hygroscopic. The moisture absorption curve during desorption exhibited hysteresis, combining with the XRPD pattern of the sample before and after the DVS test (see FIG. 29 for the XRPD pattern after the test), showing that the crystal form of crystal form K of a hydrobromide of a compound of formula I changed after moisture absorption.

The present invention provides a preparation method of the crystal form K of a hydrobromide of a compound of formula I, specifically, the method is described as follows:

conducting recrystallization or crystal transformation of crystal form H of a hydrobromide of a compound of formula I with n-heptane, to obtain crystal form K of a hydrobromide of a compound of formula I.

In some embodiments, mixing n-heptane with crystal form H of a hydrobromide of a compound of formula I to prepare suspension, stirring at room temperature, collectting the solid, and drying to obtain crystal form K of a hydrobromide of a compound of formula I.

In some embodiments, adding n-heptane to a container with crystal form H of a hydrobromide of a compound of formula I to prepare suspension, stirring at room temperature, collectting the solid, and drying to obtain crystal form K of a hydrobromide of a compound of formula I.

In some embodiments, the duration of the stirring is 4-48 hours, preferably 24 hours;

In some embodiments, collecting the solid by centrifugation and drying overnight under vacuuumat 30-60° C.

Crystal form L of a fumarate of a compound of formula I of the present invention has an X-ray powder diffraction pattern showing characteristic peaks at 2theta angles of 6.1°±0.2°, 16.3°±0.2° and 26.4°±0.2°.

The X-ray powder diffraction pattern of the crystal form L of a fumarate of a compound of formula I shows characteristic peaks at 2theta angles of 6.1°±0.2°, 13.4°±0.2°, 15.7°±0.2°, 16.3°±0.2° and 26.4°±0.2°.

The X-ray powder diffraction pattern of the crystal form L of a fumarate of a compound of formula I shows characteristic peaks at 2theta angles of 6.1°±0.2°, 13.4°±0.2°, 15.7°±0.2°, 16.3°±0.2°, 22.6°±0.2°, 23.2°±0.2°, 23.8°±0.2° and 26.4°±0.2°.

Non-restrictively, the X-ray powder diffraction data of crystal form L of a fumarate of a compound of formula I of the invention are shown in Table 12.

TABLE 12

| Diffraction angle 2θ (°) | d (A) | Relative diffraction intensity I% (based on peak height) |
| --- | --- | --- |
| 6.1 | 14.56 | 100.0 |
| 13.4 | 6.60 | 12.6 |
| 15.7 | 5.63 | 15.8 |
| 16.3 | 5.43 | 68.1 |
| 22.6 | 3.93 | 11.4 |
| 23.2 | 3.84 | 11.3 |
| 23.8 | 3.74 | 9.6 |
| 26.4 | 3.37 | 37.6 |

Non-restrictively, the XRPD pattern of crystal form L of a fumarate of a compound of formula I of the invention is shown in FIG. 30.

Non-restrictively, the DSC thermogramthermogram of crystal form L of a fumarate of a compound of formula I of the invention is shown in FIG. 31.

The present invention provides a preparation method of crystal form L of a fumarate of a compound of formula I, specifically, the method is described as follows:

dissolving a compound of formula I with a solvent to obtain a compound of formula I in the solvent, and adding fumaric acid in ethanol to the compound of formula I in the solvent under stirring, keeping stirring, collecting the solid, and drying to obtain crystal form L of a fumarate of a compound of formula I.

In some embodiments, the compound of formula I is subjected to ultrasonication, heating and is then dissolved in a solvent, wherein the solvent is selected from the group consisting of ethyl acetate, acetone and any combinations thereof.

In some embodiments, the concentration of the compound of formula I in the solvent is 10-30 mg/mL, preferably 20 mg/mL.

In some embodiments, the concentration of the fumaric acid in ethanol is 15-35 mg/mL, preferably 25 mg/mL.

In some embodiments, after adding the fumaric acid in ethanol, keeping stirring at room temperature for 4-48 hours, preferably 24 hours.

In some embodiments, collecting the solid by centrifugation and drying overnight under vacuum at 30-60° C.

Crystal form M of a benzene sulfonate of a compound of formula I of the present invention has an X-ray powder diffraction pattern showing characteristic peaks at 2theta angles of 7.5°±0.2°, 18.5°±0.2°, 25.2°±0.2° and 29.8°±0.2°.

The X-ray powder diffraction pattern of the crystal form M of a benzene sulfonate of a compound of formula I shows characteristic peaks at 2theta angles of 7.5°±0.2°, 14.1°±0.2°, 15.2°±0.2°, 18.5°±0.2°, 22.4°±0.2°, 23.0°±0.2°, 25.2°±0.2° and 29.8°±0.2°.

The X-ray powder diffraction pattern of the crystal form M of a benzene sulfonate of a compound of formula I shows characteristic peaks at 2theta angles of 7.5°±0.2°, 12.5°±0.2°, 14.1°±0.2°, 15.2°±0.2°, 18.5°±0.2°, 22.4°±0.2°, 23.0°±0.2°, 24.6°±0.2°, 25.2°±0.2° and 29.8°±0.2°.

Non-restrictively, the X-ray powder diffraction data of crystal form M of a benzene sulfonate of a compound of formula I of the invention are shown in Table 13.

TABLE 13

| Diffraction angle 2θ (°) | d (A) | Relative diffraction intensity I% (based on peak height) |
| --- | --- | --- |
| 7.5 | 11.72 | 100.0 |
| 12.5 | 7.08 | 16.5 |
| 14.1 | 6.28 | 19.4 |
| 15.2 | 5.82 | 19.0 |
| 18.5 | 4.80 | 48.6 |
| 22.4 | 3.96 | 39.3 |
| 23.0 | 3.87 | 22.7 |
| 24.6 | 3.62 | 17.6 |
| 25.2 | 3.54 | 45.3 |
| 29.8 | 2.99 | 51.3 |

Non-restrictively, the XRPD pattern of crystal form M of a benzene sulfonate of a compound of formula I of the invention is shown in FIG. 32.

Non-restrictively, the DSC thermogramthermogram of crystal form M of a benzene sulfonate of a compound of formula I of the invention is shown in FIG. 33. The DSC thermogram shows that the initial melting point of crystal form M of a benzene sulfonate of a compound of formula I of the invention is 198.73° C.

Non-restrictively, the DVS isotherm plotisotherm plot of crystal form M of a benzene sulfonate of a compound of formula I of the invention is shown in FIG. 34. The DVS isotherm plot shows a 4.6% weight gain of crystalform M of a benzene sulfonate of a compound of formula I of the invention by moisture absorption from 0% RH to 95% RH. At a humidity of 85% RH, crystal form M of a benzene sulfonate of a compound of formula I reaches a weight gain of 0.54%; at 70% RH, crystal form M of a benzene sulfonate of a compound of formula I reaches a weight gain of 0.97%. After moisture absorption, the crystal form of crystal form M of a benzene sulfonate of a compound of formula I doesn't change (see FIG. 35 for the XRPD pattern after moisture absorption).

The present invention provides a preparation method of crystal form M of a benzene sulfonate of a compound of formula I, specifically, the method is described as follows:

dissolving a compound of formula I with acetone to obtain a compound of formula I in acetone, and adding benzenesulfonic acid in acetone to the compound of formula I in acetone under stirring, keeping stirring, collecting the solid, and drying to obtain crystal form M of a benzene sulfonate of a compound of formula I.

In some embodiments, the compound of formula I is subjected to ultrasonication, heating and is then dissolved in acetone.

In some embodiments, the concentration of the compound of formula I in acetone is 10-30 mg/mL, preferably 20 mg/mL;

In some embodiments, the concentration of the benzenesulfonic acid in acetone is 15-35 mg/mL, preferably 25 mg/mL;

In some embodiments, after adding the benzenesulfonic acid in acetone, keeping stirring at room temperature for 4-48 hours, preferably 24 hours;

In some embodiments, collecting the solid by centrifugation and drying overnight under vacuum at 30-60° C.

Crystal form N of a citrate of a compound of formula I of the present invention has an X-ray powder diffraction pattern showing characteristic peaks at 2theta angles of 15.8°±0.2°, 17.0°±0.2° and 21.1°±0.2°.

Non-restrictively, the X-ray powder diffraction data of crystal form N of a citrate of a compound of formula I of the invention are shown in Table 14.

TABLE 14

| Diffraction angle 2θ (°) | d (A) | Relative diffraction intensity I% (based on peak height) |
| --- | --- | --- |
| 4.8 | 18.35 | 4.3 |
| 15.8 | 5.62 | 81.4 |
| 17.0 | 5.21 | 17.7 |
| 21.1 | 4.21 | 15.5 |

Non-restrictively, the XRPD pattern of crystal form N of a citrate of a of compound of formula I of the invention is shown in FIG. 36.

Non-restrictively, the DSC thermogram of crystal form N of a citrate of a compound of formula I of the invention is shown in FIG. 37.

The present invention provides a preparation method of the crystal form N of a citrate of a compound of formula I, specifically, the method is described as follows:

dissolving a compound of formula I with ethyl acetate to obtain a compound of formula I in ethyl acetate, and adding citric acid in ethyl acetate to the compounf of formula I in ethyl acetate under stirring, keeping stirring, collecting the solid, and drying to obtain crystal form N of a citrate of a compound of formula I.

In some embodiments, the compound of formula I is subjected to ultrasonication, heating and is then dissolved in ethyl acetate;

In some embodiments, the concentration of the compound of formula I in ethyl acetate is 10-30 mg/mL, preferably 20 mg/mL;

In some embodiments, the concentration of the citric acid in ethyl acetate is 15-35 mg/mL, preferably 25 mg/mL;

In some embodiments, after adding the citric acid in ethyl acetate, keeping stirring at room temperature for 4-48 hours, preferably 24 hours;

In some embodiments, collecting the solid by centrifugation and drying overnight under vacuum at 30-60° C.

Crystal form O of a tartrate of a compound of formula I of the present invention has an X-ray powder diffraction pattern showing characteristic peaks at 2theta angles of 6.3°±0.2°, 26.1°±0.2° and 26.9°±0.2°.

In some embodiments, the X-ray powder diffraction pattern of the crystal form O of a tartrate of a compound of formula I shows characteristic peaks at 2theta angles of 6.3°±0.2°, 12.5°±0.2°, 15.1°±0.2°, 26.1°±0.2°, 26.9°±0.2° and 27.5°±0.2°.

In some embodiments, the X-ray powder diffraction pattern of the crystal form O of a tartrate of a compound of formula I shows characteristic peaks at 2theta angles of 6.3°±0.2°, 11.4°±0.2°, 12.5°±0.2°, 14.1°±0.2°, 14.4°±0.2°, 15.1°±0.2°, 26.1°±0.2°, 26.9°±0.2° and 27.5°±0.2°.

Non-restrictively, the X-ray powder diffraction data of crystal form O of a tartrate of a compound of formula I of the invention are shown in Table 15:

TABLE 15

| Diffraction angle 2θ (°) | d (A) | Relative diffraction intensity I % (based on peak height) |
| --- | --- | --- |
| 6.3 | 14.00 | 100.0 |
| 11.4 | 7.73 | 11.0 |
| 12.5 | 7.05 | 18.3 |
| 14.1 | 6.26 | 10.9 |
| 14.4 | 6.14 | 6.2 |
| 15.1 | 5.86 | 12.6 |
| 26.1 | 3.41 | 38.5 |
| 26.9 | 3.32 | 24.2 |
| 27.5 | 3.24 | 11.7 |

Non-restrictively, the XRPD pattern of crystal form O of a tartrate of a compound of formula I of the invention is shown in FIG. 38.

Non-restrictively, the DSC thermogram of crystal form O of a tartrate of a compound of formula I of the invention is shown in FIG. 39. The DSC thermogramthermogram shows that the initial melting point of crystal form O of a tartrate of a compound of formula I of the invention is 218.80° C.

Non-restrictively, the TGA thermogramthermogram of crystal form O of a tartrate of a compound of formula I of the invention is shown in FIG. 40. The TGA thermogramthermogram shows that there is only a 0.05% weight loss of crystal form O of a tartrate of a compound of formula I of the invention from 26° C. to 120° C., indicating crystal form O of a tartrate of a compound of formula I doesn't contain crystal water or solvent.

Non-restrictively, the DVS isotherm plotisotherm plot of crystal form O of a tartrate of a compound of formula I of the invention is shown in FIG. 41. The DVS isotherm plot shows a 6.85% weight gain of crystal form O of a tartrate of a compound of formula I of the invention by moisture absorption from 0% RH to 95% RH. At a humidity of 80% RH, crystal form O of a tartrate of a compound of formula I reaches a 1.80% weight gain. After moisture absorption, the crystal form of crystal form O of a tartrate of a compound of formula I doesn't change (see FIG. 42 for the XRPD pattern after moisture absorption).

The present invention provides a preparation method of crystal form O of a tartrate of a compound of formula I, specifically, the method is described as follows:

mixing a compound of formula I with a first solvent, dissolving the compound until the solution is clear and obtaining a compound of formula I in the first solvent; mixing tartaric acid with a second solvent, dissolving the compound until the solution is clear, and obtaining tartaric acid in the second solvent; adding the tartaric acid in the second solvent to the compound of formula I in the first solvent under stirring, conducting controlled-rate cooling under stirring, collecting the solid, drying and obtaining crystal form O of a tartrate of a compound of formula I.

In some embodiments, the first solvent and the second solvent are selected from the group consisting of acetone, ethyl acetate and any combinations thereof.

In some embodiments, the molar ratio of the compound of formula I to tartaric acid is 1: (0.5-1.5), preferably 1: (0.5-0.7), more preferably 1: (0.55-0.6).

In some embodiments, in the crystal form O of a tartrate of a compound of formula I, the molar ratio of the compound of formula I to tartaric acid is 2:1.

In some embodiments, the concentration of the compound of formula I in acetone is 15-70 mg/mL, preferably 40-60 mg/mL, more preferably 50 mg/mL.

In some embodiments, the concentration of the tartaric acid in acetone is 5-35 mg/mL, preferably 10-25 mg/mL, more preferably 15 mg/mL.

In some embodiments, mixing the compound of formula I with acetone, raising the temperature to 40-60° C., preferably 50-55° C., to dissolve the compound of formula I until the solution is clear.

In some embodiments, mixing the tartaric acid with acetone, raising the temperature to 40-60° C., preferably 50-55° C., to dissolve the tartaric acid until the solution is clear.

In some embodiments, adding the tartaric acid in acetone at 40-60° C., preferably 45-55° C., to the compound of formula I in acetone.

In some embodiments, the controlled-rate cooling is realized by the following steps:
    stirring the system for 0.5-3 hours, preferably 1-2 hours, at room temperature between 35-60° C., preferably 40-60° C.;
    keeping cooling the system to 15-35° C., maintaining the temperature, stirring for 0.5-3 hours, preferably 1-2 hours;
    keeping cooling the system to 5-15° C., such as 5-10° C., and maintaining the temperature, stirring for 0.5-3 hours, preferably 1-2 hours.

In the present invention, the controlled-rate cooling can gradually cool the system in steps, and maintain a specific temperature range for a certain duration.

In some embodiments, during the controlled-rate cooling, after stirring the system for 0.5-3 hours, preferably 1-2 hours, at room temperature between 35-60° C., preferably 40-60° C., concentrating the system to one third to two thirds of the original volume, preferably half of the original volume.

In some embodiments, during the controlled-rate cooling, after keeping cooling the system to 15-35° C., maintaining the temperature and stirring for 0.5-3 hours, preferably 1-2 hours, concentrating the system to one third to two thirds of the original volume, preferably half of the original volume.

In some embodiments, the purity of the compound of formula I is more than 90%, preferably more than 95%, more preferably more than 99%.

In some embodiments, drying the collected solid between 40-60° C. under reduced pressure or with an air blower for 5-48 hours, preferably 16-28 hours.

The present invention also provides a pharmaceutical composition comprising crystal form 1 of a compound of formula I, crystal form A of a hydrocholoride of a compound of formula I, crystal form B of a hydrochloride of a compound of formula I, crystal form C of a hydrochloride of a compound of formula I, crystal form D of a sulfate of a compound of formula I, crystal for E of a phosphate of a compound of formula I, crystal form F of a phosphate of a compound of formula I, crystal form G of a mesylate of a compound of formula I, crystal form H of a hydrobromide of a compound of formula I, crystal form J of a hydrobromide of a compound of formula I, cyrstal form K of a hydrobromide of a compound of formula I, crystal form L of a fumarate of a compound of formula I, crystal form M of a benzene sulfonate of a compound of formula I, crystal form N of a citrate crystal of a compound of formula I and/or crystal form O of a tartrate of a compound of formula I.

The present invention also provides a pharmaceutical formulation comprising crystal form 1 of a compound of formula I, crystal form A of a hydrochloride of a compound of formula I, crystal form B of a hydrochloride of a compound of formula I, crystal form C of a hydrochloride of a compound of formula I, crystal form D of a sulfate of a compound of formula I, crystal form E of a phosphate of a compound of formula I, crystal form F of a phosphate of a compound of formula I, crystal form G of a mesylate of a compound of formula I, crystal form H of a hydrobromide of a compound of formula I, crystal form J of a hydrobromide of a compound of formula I, crystal form K of a hydrobromide of a compound of formula I, crystal form L of a fumarate of a compound of formula I, crystal form M of a benzene sulfonate of a compound of formula I, crystal form N of a citratee of a compound of formula I and/or crystal form O of a tartrate of a compound of formula I.

Use of crystal form 1 of a compound of formula I, crystal form A of a hydrochloride of a compound of formula I, crystal form B of a hydrochloride of a compound of formula I, crystal form C of a hydrochloride of a compound of formula I, crystal form D of a sulfate of a compound of formula I, crystal form E of a phosphate of a compound of formula I, crystal form F of a phosphate of a compound of formula I, crystal form G of a mesylate of a compound of formula I, crystal form H of a hydrobromide of a compound of formula I, crystal form J of a hydrobromide of a compound of formula I, crystal form K of a hydrobromide of a compound of formula I, crystal form L of a fumarate of a compound of formula I, crystal form M of a benzene sulfonate of a compound of formula I, crystal form N of a citrate of a compound of formula I and/or crystal form O of a tartrate of a compound of formula I in preparing medicaments for treating JAK1/TYK2-related diseases or conditions, wherein the diseases or conditions can be autoimmune diseases or disorders, such as rheumatoid arthritis or inflammatory diseases or disorders, and cancers or tumor proliferative diseases or disorders.

In the present invention, unless otherwise specified, the involved temperatures refer to the internal temperatures of the reaction system.

In terms of the melting point, a person skilled in the art can understand that in a DSC test, there are a certain range of changes in the actually measured initial melting point due to the influences of measuring instrument, heating rate and crystalline shape, etc.; generally, these changes are within ±5° C.

EMBODIMENTS

Figure 1:
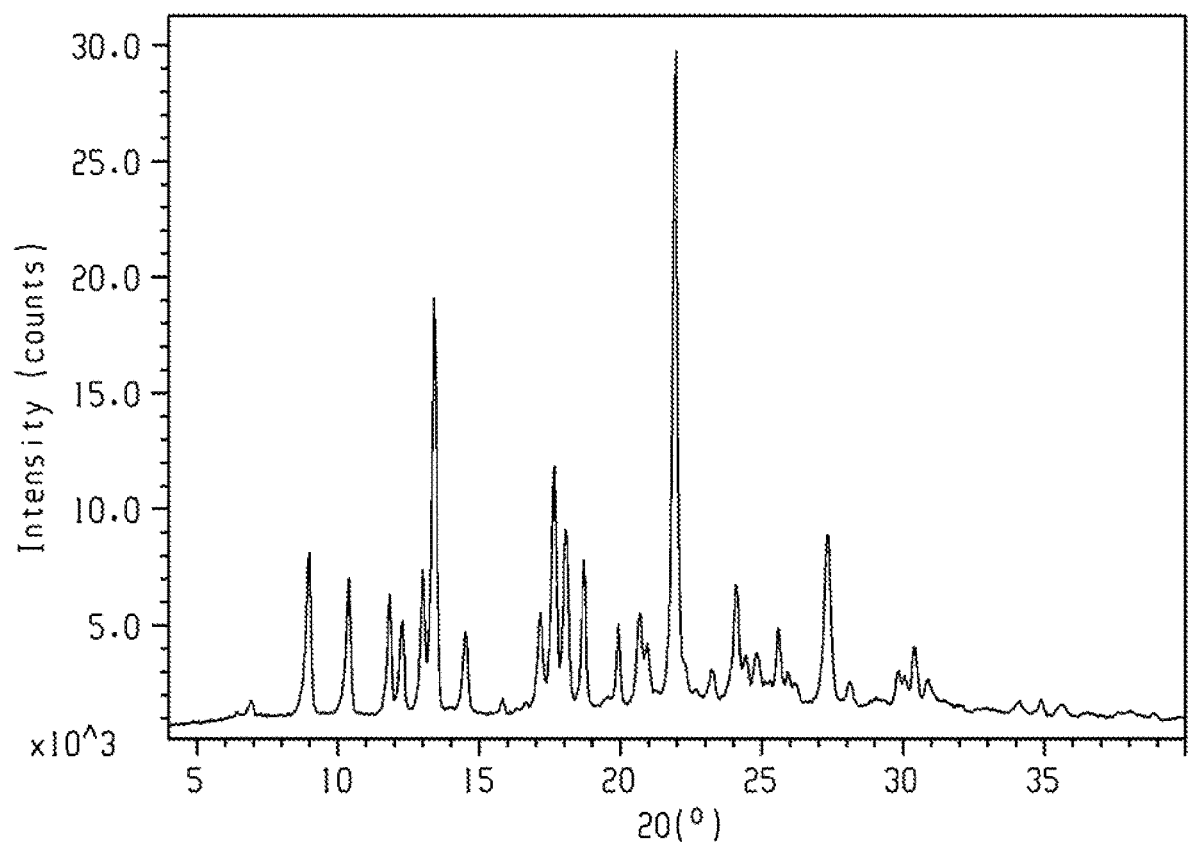
FIG. 1 is the XRPD pattern of crystal form 1 of a compound of formula I of the invention.
Figure 2:
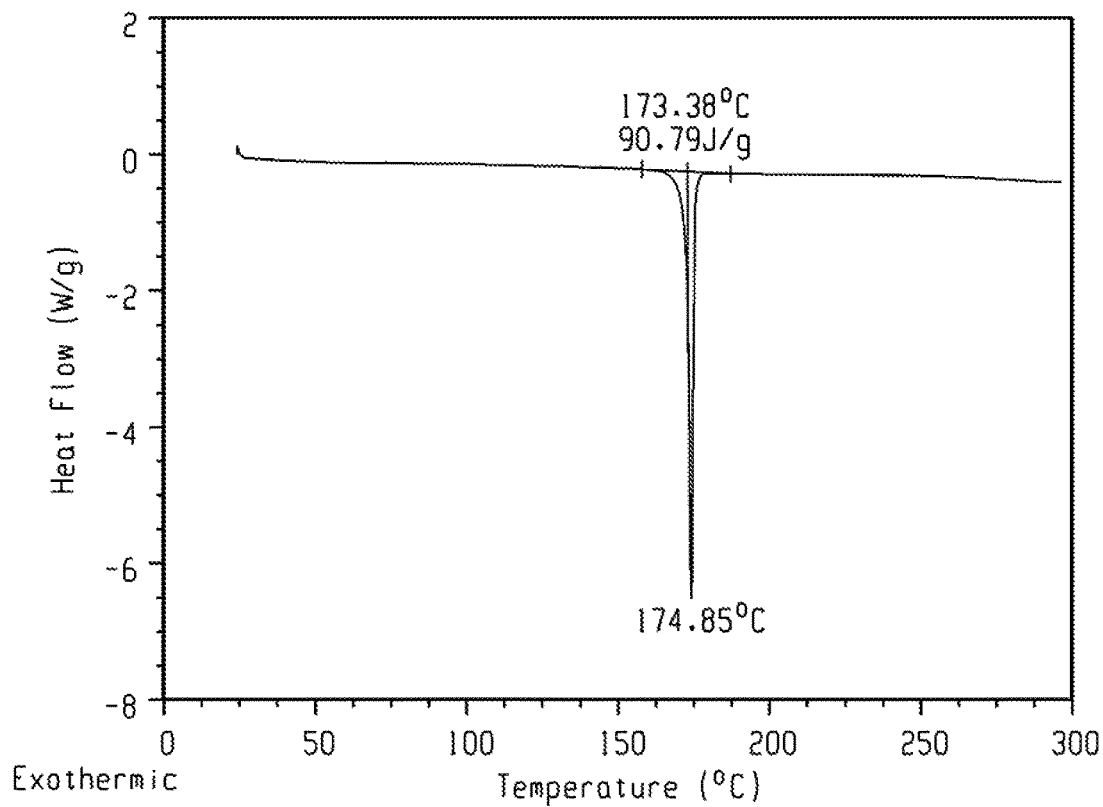
FIG. 2 is the DSC thermogram of crystal form 1 of a compound of formula I of the invention.
Figure 3:
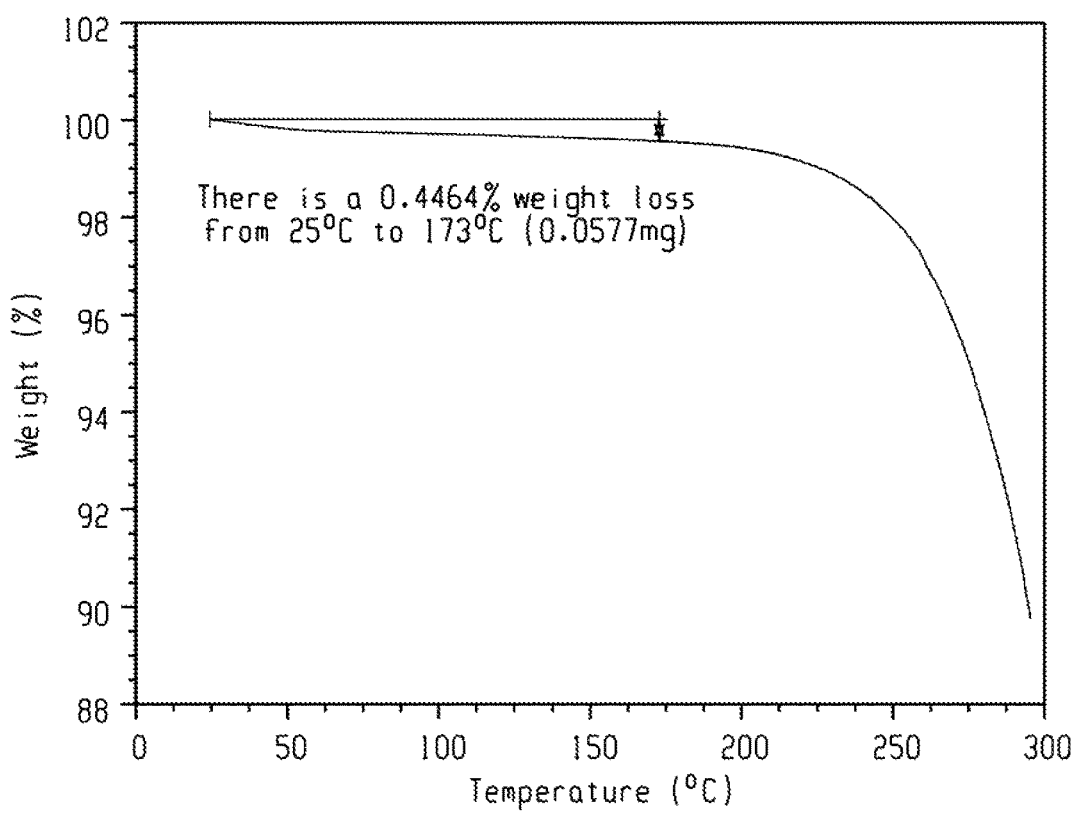
FIG. 3 is the TGA thermogram of crystal form 1 of a compound of formula I of the invention.
Figure 4:
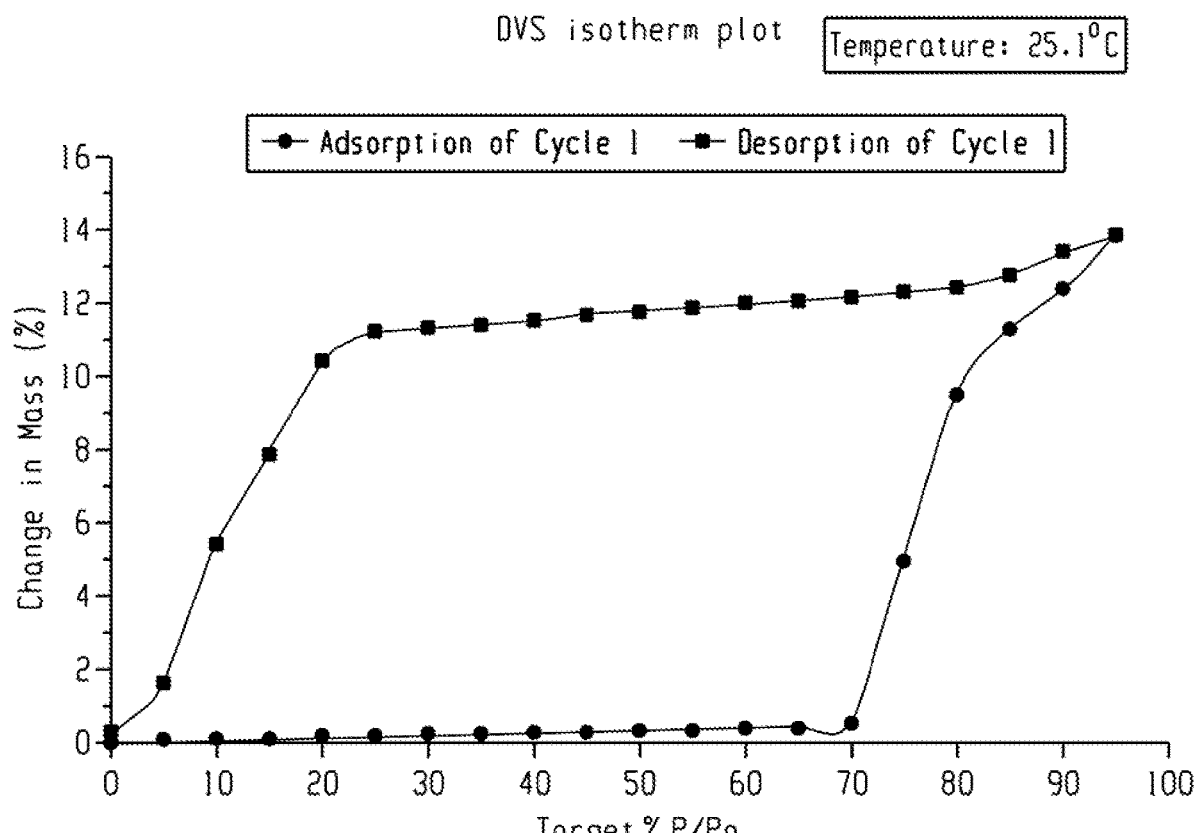
FIG. 4 is the DVS isotherm plot of crystal form 1 of a compound of formula I of the invention.
Figure 5:
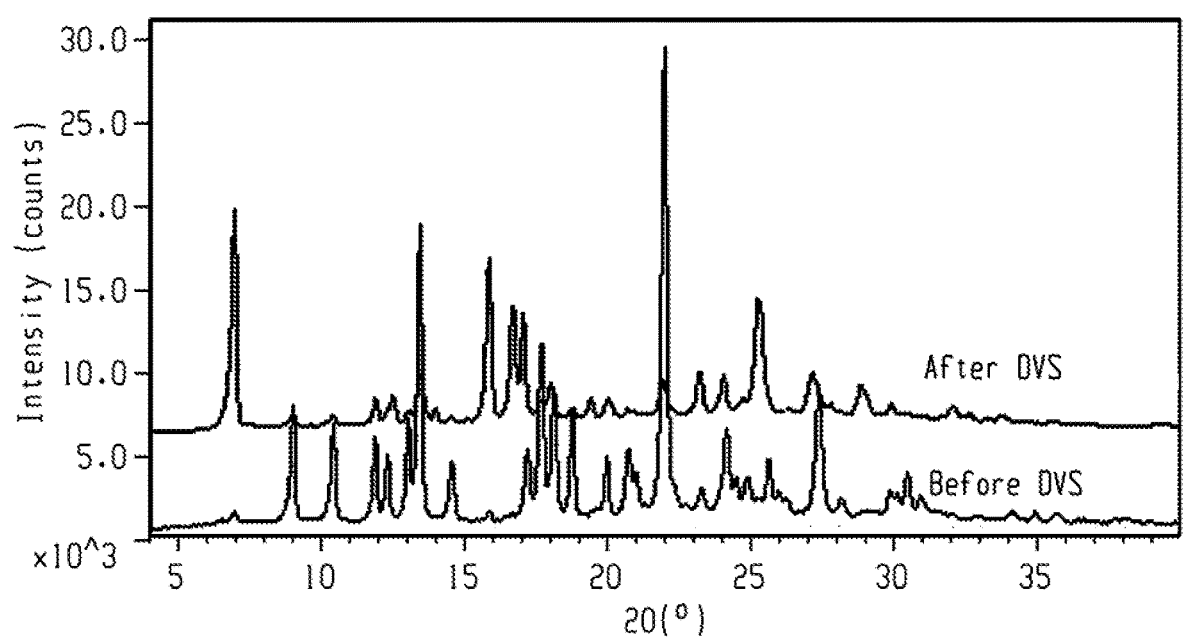
FIG. 5 is the XRPD overlay pattern of crystal form 1 of a compound of formula I of the invention before and after the DVS test.

The following embodiments further explain the invention, but don't constitute a restriction or limitation to the scope of the invention.

| No | Instrument | Model | Manufacturer | Test methods |
|---|---|---|---|---|
| 1 | High performance liquid chromatograph (UPLC) | Agilent 1200, DAD | Agilent | Instrument: Agilent 1200 DAD HPLC System or Similar configuration Chromatographic column: Waters |

| No | Instrument | Model | Manufacturer | Test methods |
|---|---|---|---|---|
| 2 | Liquid chromatography-mass spectrometry (LC-MS) | Agilent 1200 HPLC/6100 SQ System | Agilent | XBridge Shield RP18 4.6 × 150 mm, 3.5 μm<br>Mobile phase: A: 0.05% phosphoric acid aqueous solution;<br>B: Acetonitrile<br>Instrument: Agilent 1200 HPLC/6100 SQ System<br>Chromatographic column: Agilent XDB-C18, 4.6 mm × 50 mm, 1.8 μm<br>Mobile phase: A: 0.05% TFA in water;<br>B: 0.05% TFA in acetonitrile |
| 3 | Nuclear magnetic resonance spectroscopy $^1$HNMR | AVANCE III 400 MHz | BRUKER | Ultrashield-Plus Digital NMR Spectroscopy<br>Experiment: N PROTON 1H experiment (default parameters) |
| 4 | X-ray powder diffractometer (XRPD) | D8 Advance | BRUKER | Light source is CuK. X-ray intensity is 40 KV/40 mA. Scanning mode is Theta-theta. Scanning angle range is 4-40°. Step length is 0.05°. Scanning speed is 0.5 seconds/step. |
| 5 | Differential scanning calorimeter (DSC) | Q1000 | TA | Weighing 2-4 mg of sample and placing the sample into a unsealed aluminum pan, allowing the sample to reach the equilibrium in nitrogen flow (50 mL/min) at 25° C., and raising the temperature from 25° C. to 300° C. at 10° C./min. |
| 6 | Thermo gravimetric analyzer (TGA) | Q500 | TA | Weighing 10-20 mg of sample and placing the sample into a platinum sample pan, allowing the sample in nitrogen flow (60 mL/min) and the balance in nitrogen flow (40 mL/min) to reach equilibrium at 25° C., and raising the temperature from 25° C. to 300° C. at 10° C./min. |
| 7 | Dynamic vapor sorption analyzer (DVS) | Advantage 1 | Surface Measurement System | Weighing about 10 mg of the sample, setting the temperature as 25° C., drying for 60 minutes at a humidity of 0% RH, and determining the moisture absorption characteristics of the samples when the humidity changes from 0% RH to 95% RH, and the dehumidification characteristics of the samples when the humidity changes from 95% RH to 0% RH. The humidity change step is 5% RH. When the mass change rate dm/dt is less than 0.002%, it is considered as the scale balance. The mass change rate less than 0.01%/min within 5 minutes is the balance criterion in the test and the maximum equilibration time is 2 hours. |
| 8 | Ion chromatography | ICS-2000 + AS40 Automated sampler | DIONEX | Chromatographic column: IonPac ® AS11-HC 4*250 mm;<br>Column temperature: 30° C.;<br>Eluent: 10 mM KOH aqueous solution<br>Flow rate: 1.00 mL/min<br>Suppressor: Dionex AERS 500 4 mm<br>Electric current of suppressor: 25 mA<br>Runtime: 15 min |

Information on raw materials and reagents used in the invention is as follows:

| Material | Purity/grade | Lot No. | Manufacturer |
|---|---|---|---|
| Compound of formula V | ≥98.0% | KM1009-1804001 | ZINNOVA |
| Compound of formula IV | ≥98.0% | KM1008-1804001 | ZINNOVA |
| N,N-Diisopropylethylamine (DIPEA) | AR | KM261A-1801002 | Shanghai Qiao Chemical Science Co., Ltd. |
| Ethanol | / | 160321047B | Nanjing Chemical Reagent Co., Ltd. |
| Methanol | AR | P1176856 | GENERAL-REAGENT |
| Tetrahydrofuran (THF) | AR | P1167158 | GENERAL-REAGENT |

-continued

| Material | Purity/grade | Lot No. | Manufacturer |
|---|---|---|---|
| Dichloromethane (DCM) | AR | P1216848 | GENERAL-REAGENT |
| Ethyl acetate (EA) | AR | P1080359 | GENERAL-REAGENT |
| Acetone | AR | P1160778 | GENERAL-REAGENT |
| Acetonitrile | HPLC | 6308IX20 | Anhui Fulltime Specialized Solvent & Reagent Co., Ltd. |
| N-hexane | AR | P1196621 | GENERAL-REAGENT |
| Purified water | Milli-Q | Prepared on the same day | Milli-Q |
| Methyl tert-butyl ether (MTBE) | AR | P1135054 | GENERAL-REAGENT |
| Isopropanol | HPLC | 6553IU13 | Anhui Fulltime Specialized Solvent & Reagent Co., Ltd. |
| Palladium on carbon (Pd/C) | AR | KM416A-1603001 | Shaanxi Rock New Materials Co., Ltd. |
| Trimethyl orthoacetate | 98%+ | KM1013-1805001 | Shanghai Titan Scientific Co., Ltd. |
| Pyridine hydrochloride | 98%+ | KM616-1703001 | Jiangsu Heng An Chemical Industry Co., Ltd. |
| Hydrobromic acid | 45% | P1337848 | Adamas-beta |
| Tartaric acid (L) | 99%+ | P1311486 | Adamas-beta |
| Benzenesulfonic acid monohydrate | 98%+ | P1257168 | Adamas-beta |
| Hydrochloric acid | 36-38% | P1246465 | GENERAL-REAGENT |
| Sulfuric acid | 95-98% | 20140301 | Wuxi Jiani Chemistry Co., Ltd. |
| Methanesulfonic acid | >98.0% | P1133997 | GENERAL-REAGENT |
| Fumaric acid | 99% | LU80M51 | J&KCHEMICAL |
| Citric acid | Pharmaceutical-grade | 160105001C | Nanjing Chemical Reagent Co., Ltd. |
| P-toluenesulfonic acid | >99.5% | 20101208 | Shanghai Lingfeng Chemical Reagent Co., Ltd. |
| Phosphoric acid | 85% | H2160 | Honeywell |
| Silicon based metal eliminator (Thiol silica gel) | Sulphur content ≥3.2% | — | Shanghai Chiral Chemistry Co., Ltd. |
| Methanolic potassium hydroxide VS | AR | 0.1 mol/L | — |
| Potassium hydrogen phthalate | AR | ≥99.5% | — |

EXAMPLES

Preparation of a Compound of Formula III

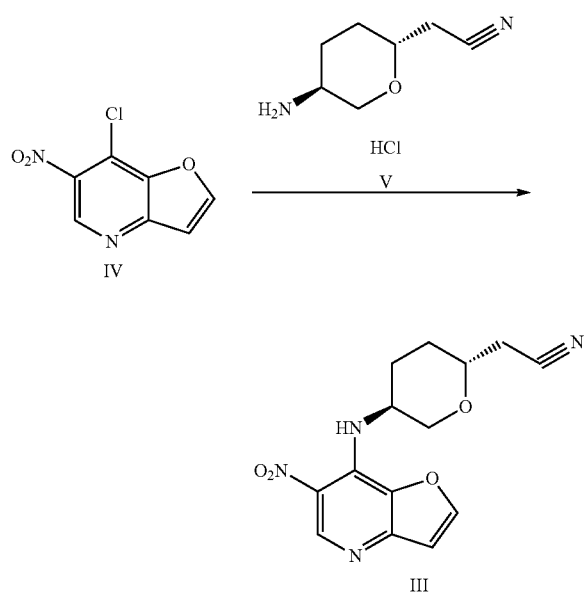

Example 1

Preparation of a Compound of Formula III

Ethanol (4 mL), a compound of formula IV (0.20 g, 1.0 eq), a compound of formula V (0.18 g, 1.0 eq), and DIPEA (0.39 g, 3.0 eq) were added to a 25 mL three-necked flask, and were stirred; under nitrogen protection, the system was heated to reflux (70-80° C.), stirred overnight at the reflux temperature; the system was cooled to room temperature (15-20° C.), solids were precipitated during cooling; water (4 mL) was added to the system dropwise, the system was stirred for 2 hours at room temperature (15-20° C.); filterred, the filter cake was washed with ethanol aqueous solution (2 mL, V/V, 1:1), the filter cake was dried under vacuum at 45-50° C. for 16 hours; about 0.21 g of yellow solids were obtaind, with a LC-MS purity of 96.4% (214 nm) and a yield of 69%.

MS-ESI: $[M+1]^+$: 303.1

$^1$H NMR(400 MHz, CDCl$_3$): 9.238 (s, 1H), 8.400 (d, 1H), 7.968 (d, 1H), 6.987 (d, 1H), 4.537-4.613 (m, 1H), 4.305-4.350 (m, 1H), 3.661-3.722 (m, 1H), 3.313-3.366 (m, 1H), 2.590-2.699 (m, 2H), 2.407-2.454 (m, 1H), 1.815-2.035 (m, 1H), 1.688-1.806 (m, 2H).

Example 2

Preparation of a Compound of Formula III

Ethanol (120 mL, 20V), a compound of formula IV (6.0 g, 1.0 eq), a compound of formula V (5.4 g, 1.01 eq), and DIPEA (11.7 g, 3.0 eq) were added to a 250 mL three-necked flask, and were stirred; under nitrogen protection, the system was heated to 70-80° C. (internal temperature) and stirred with the temperature maintained for 8 hours; the system was cooled to room temperature (15-20° C.), solids were precipitated during cooling; water (120 mL, 20V) was added to the system dropwise, the system was stirred for 2 hours at room temperature (10-15° C.); filterred, the filter cake was washed with ethanol aqueous solution (30 mL, 1:1), the filter cake was dried under vacuum at 50° C. for 16 hours; about 7.7 g of yellow solids were obtain in total, with an HPLC purity of 95.5% and a yield of 84.3%.

The MS-ESI and $^1$H NMR data are consistent with example 1.

Example 3

Preparation of a Compound of Formula III

Ethanol (5 mL, 10V), a compound of formula IV (0.50 g, 1.0 eq), a compound of formula V (0.45 g, 1.01 eq), and DIPEA (0.98 g, 3.0 eq) were added to a 25 mL three-necked flask, and were stirred; under nitrogen protection, the system was heated to 70-80° C., and was allowed to reflux and was stirred for 5 hours; the system was cooled to room temperature (15-20° C.), solids were precipitated during cooling; water (5 mL, 10V) was added to the system dropwise, the system was stirred for 2 hours at room temperature (10-15° C.); filterred, the filter cake was washed with ethanol aqueous solution (1:1) (1.5 mL, 3V), the filter cake was dried under vacuum at 50° C. for 16 hours; about 0.54 g of brown solids were obtain in total, with an HPLC purity of 95.4% and a yield of 71%.

The MS-ESI and $^1$H NMR data are consistent with example 1.

Example 4

Preparation of a Compound of Formula III

Ethanol (5 mL, 10V), a compound of formula IV (0.50 g, 1.0 eq), a compound of formula V (0.45 g, 1.01 eq), and DIPEA (0.72 g, 2.2 eq) were added to a 25 mL three-necked flask, and were stirred; under nitrogen protection, the system was heated to 70-80° C., and was allowed to reflux and was stirred for 5 hours; the system was cooled to room temperature (15-20° C.), solids were precipitated during cooling; water (7.5 mL, 15V) was added to the system dropwise, the system was stirred for 1 hour at room temperature (10-15° C.); the system was cooled to 5-10° C. and was stirred for 2 hours; filterred, the filter cake was washed with ethanol aqueous solution (1:1) (1.5 mL, 3V), the filter cake was dried under vacuum at 50° C. for 16 hours; about 0.57 g of brown solids were obtain in total, with an HPLC purity of 91.4% and a yield of 75%.

The MS-ESI and $^1$H NMR data are consistent with example 1.

Example 5

Preparation of a Compound of Formula III

Ethanol (50 mL, 10V), a compound of formula IV (5.0, 1.0 eq), a compound of formula V (4.5 g, 1.01 eq), and DIPEA (7.2 g, 2.2 eq) were added to a 250 mL three-necked flask, and were stirred; under nitrogen protection, the system was heated to 70-80° C., and was allowed to reflux and was stirred for 5 hours; the system was cooled to room temperature (15-20° C.), solids were precipitated during cooling; water (75 mL, 15V) was added to the system dropwise, the system was stirred for 1 hour at room temperature (10-15° C.); the system was cooled to 5-10° C. and was stirred for 2 hours; filterred, the filter cake was washed with ethanol aqueous solution (1:1, 15 mL), the filter cake was dried under vacuum at 50° C. for 16 hours; about 6.6 g of yellow solids were obtain in total, with an HPLC purity of 94.2% and a yield of 86.7%.

The MS-ESI and $^1$H NMR data are consistent with example 1.

Example 6

Preparation of a Compound of Formula III

Ethanol (180 mL, 10V), a compound of formula IV (17.8 g, 1.0 eq), a compound of formula V (16.0 g, 1.01 eq), and DIPEA (25.7 g, 2.2 eq) were added to a 500 mL three-necked flask, and were stirred; under nitrogen protection, the system was heated to 70-80° C., and was allowed to reflux and was stirred for 5 hours; the system was cooled to room temperature (15-20° C.), solids were precipitated during cooling; water (270 mL, 15V) was added to the system dropwise, the system was stirred for 1 hour at room temperature (10-15° C.); the system was cooled to 5-10° C. and was stirred for 2 hours; filterred, the filter cake was washed with ethanol aqueous solution (ethanol:water=1:1.5, v/v, 40 mL), the filter cake was dried under vacuum at 50° C. for 16 hours; about 23.0 g of brown solids were obtain in total, with an HPLC purity of 95.3% and a yield of 85.2%.

The MS-ESI and $^1$H NMR data are consistent with example 1.

Example 7

Preparation of a Compound of Formula III

Ethanol (1000 mL, 10V), a compound of formula IV (100 g, 1.0 eq), a compound of formula V (89.9 g, 1.01 eq), and DIPEA (143.2 g, 2.2 eq) were added to a 3000 mL three-necked flask, and were stirred; under nitrogen protection, the system was heated to 85-90° C. (internal temperature: about 75° C.), and was allowed to reflux and was stirred for 10 hours; the system was cooled to room temperature (15-20° C.), solids were precipitated during cooling; water (1500 mL, 15V) was added to the system dropwise, the system was stirred for 1 hour at room temperature (10-15° C.); the system was cooled to 5-10° C. and was stirred for 2 hours; filterred, the filter cake was washed with ethanol aqueous solution (1:1.5, v/v, 200 mL), the filter cake was dried under vacuum at 50° C. for 16 hours; about 130 g of reddish brown solids were obtain in total, with an HPLC purity of 94.2% and a yield of 85.5%.

The MS-ESI and $^1$H NMR data are consistent with example 1.

Example 8

Preparation of a Compound of Formula III

Ethanol (2000 mL, 10V), a compound of formula IV (200 g, 1.0 eq), a compound of formula V (179.7 g, 1.01 eq), and DIPEA (286.4 g, 2.2 eq) were added to a 5000 mL three-necked flask, and were stirred; under nitrogen protection, the system was heated to 70-80° C. (internal temperature: about 65-70° C.), and was allowed to reflux and was stirred for 16 hours; the system was cooled to room temperature (15-20° C.), solids were precipitated during cooling; water (3000 mL, 15V) was added to the system dropwise, the system was stirred for 1 hour at room temperature (10-15° C.); the system was cooled to 5-10° C. and was stirred for 2 hours; filterred, the filter cake was washed with ethanol aqueous solution (1:1.5, v/v, 400 mL), the filter cake was dried with an air blower at 50° C. for 16 hours; about 251 g of reddish brown solids were obtaind in total, with an HPLC purity of 93.4%, a content of 94.7% and a content yield of 78.1%.

The MS-ESI and $^1$H NMR data are consistent with example 1.

Example 9

Preparation of a Compound of Formula III

Ethanol (5000 mL, 10V), a compound of formula IV (500 g, 1.0 eq), a compound of formula V (450 g, 1.01 eq), and DIPEA (723 g, 2.2 eq) were added to a 20000 mL three-necked flask, and were stirred; under nitrogen protection, the system was heated to 80-90° C. (internal temperature: about 70-80° C.), and was allowed to reflux and was stirred for 16 hours; the system was cooled to room temperature (25-30° C.), solids were precipitated during cooling; water (7500 mL, 15V) was added to the system dropwise, the system was stirred for 1 hour at room temperature (25-30° C.); the system was cooled to 10-15° C. and was stirred for 2 hours; filterred, the filter cake was washed with ethanol aqueous solution (1:1.5, v/v, 1000 mL), the filter cake was dried in an oven under vacuum at 50-55° C. for 24 hours; about 623 g of products were obtaind in total, with an HPLC purity of 93.7%, ethanol residue of 0.5%, a content of 93.1%, and a content yield of 76.2%.

The MS-ESI and $^1$H NMR data are consistent with example 1.

Example 10

Preparation of a Compound of Formula III

Ethanol (100 mL, 10V), a compound of formula IV (10.0 g, 1.0 eq), a compound of formula V (9.0 g, 1.01 eq), and DIPEA (14.3 g, 2.2 eq) were added to a 500 mL three-necked flask, and were stirred; the system was heated to 70-80° C., and was allowed to reflux and was stirred for 16 hours; the system was cooled to room temperature (20-30° C.), solids were precipitated during cooling; water (150 mL, 15V) was added to the system, the system was stirred for 2 hours at room temperature (20-30° C.); the system was cooled to 5-10° C. and was stirred for 2 hours; filterred, the filter cake was washed with ethanol aqueous solution (1:1.5, v/v, 25 mL), the filter cake was dried in an oven under vacuum at 50-55° C. for 16 hours; about 13.7 g of products were obtaind in total, with an HPLC purity of 93.7%, and a yield of 90%.

The MS-ESI and $^1$H NMR data are consistent with example 1.

Example 11

Preparation of a Compound of Formula III

Ethanol (17 Kg, 10V), a compound of formula IV (2.2 Kg, 1.0 eq), a compound of formula V (1.98 Kg, 1.01 eq), and DIPEA (3.19 Kg, 2.2 eq) were added to a R0462 reactor, and were stirred; under nitrogen protection, the system was heated to 75-80° C. (internal temperature, about 70-80° C.), and was stirred for 16 hours; the system was cooled to room temperature (15-25° C.), solids were precipitated during cooling; water (33 Kg, 15V) was added to the system dropwise, the system was stirred for 2 hours at room temperature (10-15° C.); the system was cooled to 5-10° C. and was stirred for 4 hours; filterred, the filter cake was washed with ethanol aqueous solution (ethanol:water=1:2, v/v, 6.2 Kg), the filtemr cake was dried at a jacket temperature between 45-55° C. and under vacuum≤−0.08 MPa for 16 hours; about 2.64 g of brown solides were obtaind in total, with an HPLC purity of 94.0%, a content of 93.4% and a content yield of 79.04%.

The MS-ESI and $^1$H NMR data are consistent with example 1.

Preparation of a Compound of Formula II

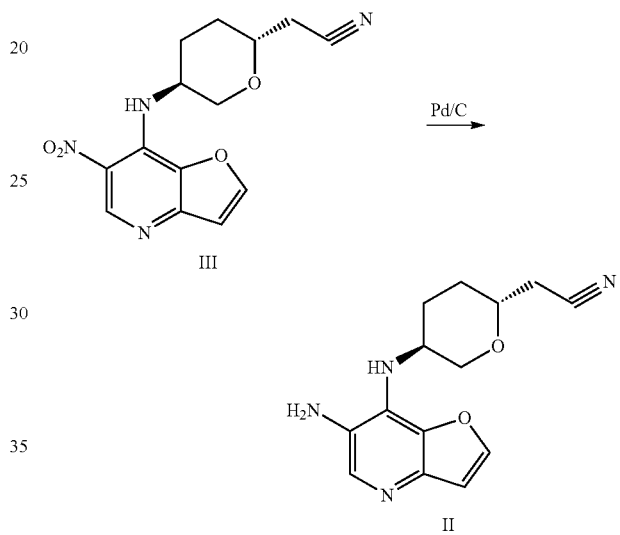

Example 12

Preparation of a Compound of Formula II

A compound of formula III (5.0 g), THF (50 mL, 10 V) and palladium on carbon (0.75 g, 10% Pd/C, 50% wet) were added to a 100 mL stainless steel autoclave seuquentially; the system was purged with nitrogen 5 times, then with hydrogen 5 times; the pressure of the system was increased to 0.50 MPa with hydrogen, then the system was heated to 25-35° C. and stirred 24 hours with the temperature maintained; the reaction liquid was filtered with diatomite, the filter cake was washed with THF (20 mL), and the filtrate was concentrated to dryness to obtain 4.2 g of brown solids, with an HPLC purity of 94.9% and a yield of 93.3%.

MS-ESI: [M+1]$^+$: 273.1

$^1$H NMR (400 MHz, CDCl$_3$): 7.988 (s, 1H), 7.688 (d, 1H), 6.805 (d, 1H), 4.190-4.338 (m, 3H), 3.584-3.648 (m, 1H), 3.147-3.206 (t, 1H), 2.594-2.651 (d, 2H), 2.318-2.364 (m,1H), 1.917-1.974 (m, 1H), 1.633-1.738 (m, 1H), 1.456-1.525 (m, 1H).

Example 13

Preparation of a Compound of Formula II

A compound of formula III (120.0 g), THF (2400 mL, 20 V) and palladium on carbon (18 g, 10% Pd/C, 50% wet)

were added to a 5000 mL stainless steel autoclave seuquentially; the system was purged with nitrogen 5 times, then with hydrogen 5 times; the pressure of the system was increased to 0.50 MPa with hydrogen, then the system was heated to 25-35° C. and stirred 24 hours with the temperature maintained; the reaction liquid was filtered with diatomite, the filter cake was washed with THF (600 mL) (until TLC almost did not show fluorescence), and the filtrate was concentrated to obtain 130 g of black semi-oily solids, with an HPLC purity of 91.7% and a yield of 120.26%.

The MS-ESI and $^1$H NMR data are consistent with example 12.

Example 14

Preparation of a Compound of Formula II

A compound of formula III (100.0 g), THF (2000 mL, 20 V) and palladium on carbon (15.0 g, 10% Pd/C, 50% wet) were added to a 5 L stainless steel autoclave seuquentially; the system was purged with nitrogen 5 times, then with hydrogen 5 times; the pressure of the system was increased to 0.5-1.0 MPa with hydrogen, the temperature of the jacket was set to 30° C., the system was stirred for 16 hours with the temperature maintained, the reaction liquid was filtered with diatomite, the filter cake was washed with THF (1000 mL), 3877 g of a compound of formula II in THF was obtained in total.

Post-treatment 1: the above filtrate (1820 g, about 40 g of a compound of formula II calculated according to a 100% yield) was concentrated to (2-3 V, 80-120 mL) with a rotary evaporator, the system was exchanged with ethanol (150 mL×2) to (2-3 V, 80-120 mL); 78 g of a compound of formula II in ethanol was obtained, with a content of 47.25%, and a content yield of 92.14%.

Post-treatment 2: the above filtrate (450 g, about 10 g of a compound of formula II calculated according to a 100% yield) was concentrated to dryness with a rotary evaporator; 10.5 g of brownish red solids were obtained.

Post-treatment 3: the above filtrate (450 g, about 10 g of a compound of formula II after calculation) was added to a flask, concentrated to about 30-40 mL (3-4 V) with a rotary evaporator; the concentrated residue was exchanged with ethanol (50 mL×2) to about 30-40 mL (3-4 V); black oily concentrated residues were obtained, the concentrated residues were directly fed to the next step of reaction.

The MS-ESI and $^1$H NMR data are consistent with example 12.

Example 15

Preparation of a Compound of Formula II

THF (240 mL, 20 V), a compound of formula III (12.0 g), and palladium on carbon (1.8 g, 5% Pd/C, 50% wet) were added to a 5000 mL three-necked flask seuquentially; the system was purged with nitrogen 5 times, then with hydrogen 5 times; the system was stirred for 48 hours with the temperature maintained at room temperature (25-30° C.) and under hydrogen pressure (about 0.1 MPa); the filter liquid was filtered, the filter cake was washed wtih THF (60 mL); the combined filtrate was concentrated with a rotary evapaoratore to 20-30 mL, the system was exchanged with ethanol (60 mL×2) to 20-30 mL; 24 g of a compound of formula II in ethanol was obtained, which is directly used for the next step of reaction.

The MS-ESI and $^1$H NMR data are consistent with example 12.

Example 16

Preparation of a Compound of Formula II

THF (1500 mL, 15 V), a compound of formula III (100 g), and palladium on carbon (15 g, 5% Pd/C, 50% wet) were added to a 5000 mL three-necked flask seuquentially; the system was purged with nitrogen 5 times, then with hydrogen 5 times; the system was stirred for 48 hours with the temperature maintained at room temperature (20-25° C.) and under hydrogen pressure (about 0.1 MPa); the filter liquid was filtered, the filter cake was washed with THF (200 mL); the combined filtrate was concentrated with a rotary evapaoratore to 200-300 mL, 185.6g of a compound of formula II in THF was obtained, with an HPLC purity of 94.2%, a content of 43.2% and a content yield of 94.0%.

The MS-ESI and $^1$H NMR data are consistent with example 12.

Example 17

Preparation of a Compound of Formula II

THF (12400 mL, 20 V), a compound of formula III (620 g), and palladium on carbon (93 g, 5% Pd/C, 50% wet) were added to a 20000 mL three-necked flask seuquentially; the system was purged with nitrogen 5 times, then with hydrogen 5 times; the system was stirred for 48 hours with the temperature maintained at room temperature (30-35° C.) and under hydrogen pressure (about 0.1 MPa); the filter liquid was filtered with diatomite (200 g), the filter cake was washed with THF (1200 mL); the combined filtrate was concentrated with a rotary evapaoratore to 1200-1800 mL, 1664 g of a compound of formula II in THF was obtained, with an HPLC purity of 93.8%, a content of 34.57% and a content yield of 110.6%.

The MS-ESI and $^1$H NMR data are consistent with example 12.

Example 18

Preparation of a Compound of Formula II

THF (140 mL, 70 V), a compound of formula III (2.0 g), and palladium on carbon (0.3 g, 5% Pd/C, 50% wet) were added to a 250 mL autoclave; the autoclave was covered with a cap and the nut was tightened; the system was purged with nitrogen 3 times, then with hydrogen 3 times; the autoclave was charged with hydrogen to about a pressure of 0.50±0.05 MPa, the inlet valve was closed; the stirring apparatus was started at a rotating speed of 500 r/min; the hydrogen pressure of the autoclave was maintained at 0.5±0.05 MPa between 25-35° C., the system was stirred for reacting for 96 hours, the reaction liquid was filtered with diatomite (10 g), the filter cake was washed with THF (60 mL); the combined filtrate was concentrated with a rotary evapaoratore to dryness to obtain 1.8 g of semi-oily solids with an HPLC purity of 91.2%, and a yield of 99.9%.

The MS-ESI and $^1$H NMR data are consistent with example 12.

Example 19

Preparation of a Compound of Formula II

THF (167 Kg, 70 V), a compound of formula III (2.64 g), and palladium on carbon (0.4 Kg, 5% Pd/C, 50% wet) were added to a 500 L autoclave; the system was purged with nitrogen 5 times, then with hydrogen 5 times; the autoclave was charged with hydrogen to about a pressure of 0.50±0.05 MPa, the inlet valve was closed; the stirring apparatus was started; the hydrogen pressure of the autoclave was maintained at 0.5±0.05 MPa between 25-35° C., the system was stirred for reacting for 120 hours, the system was filtered under a pressure, the filter cake was washed with THF (13 Kg); the combined filtrate was distilled under reduced pressure (to 2 V-3 V) to obtain 11Kg of a compound of formula II in THF, with an HPLC purity of 90.7%, a content of 18.5% and a content yield of 91.9%.

The MS-ESI and $^1$H NMR data are consistent with example 12.

Example 20

Preparation of a Compound of Formula II

THF (60 mL, 12 V), a compound of formula III (5.0 g), and palladium on carbon (0.75 g, 5% Pd/C, 50% wet) were added to a 100 mL stainless steel autoclave; the system was purged with nitrogen 5 times, then with hydrogen 5 times; the pressure of the system was increased to 0.5-1.0 MPa with hydrogen, the temperature of the jacket was set to 30° C., the system was stirred for 42 hours with the temperature maintained; after the reaction was completed, the reaction liquid was filtered with diatomite, the filter cake was washed with THF (100 mL); 197.8 g of a compound of formula II in THF was obtained in total; the solution was concentrated with a rotary evaporator to (2-3 V, 10-15 mL); the system was exchanged with ethanol (25 mL×2) to (2-3 V, 10-15 mL); the obtained compound of formula II in ethanol was directly used for the next step of reaction.

The MS-ESI and $^1$H NMR data are consistent with example 12.

Preparation of a Compound of Formula I

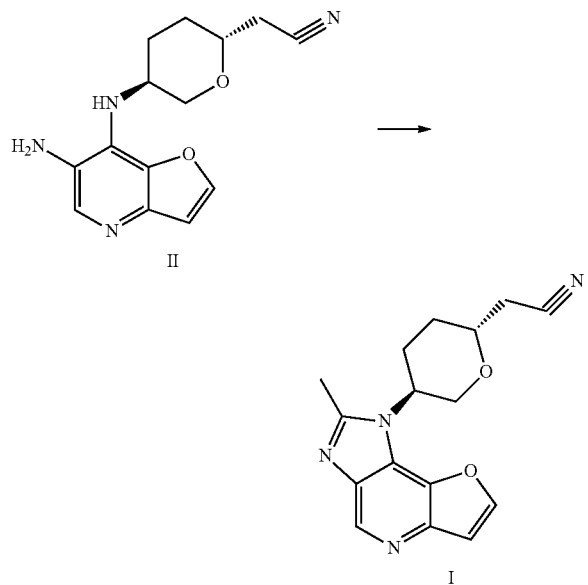

Preparation of a Compound of Formula I

Example 21

Preparation of a Compound of Formula I

A compound of formula II (5 g, 1.0 eq), trimethyl orthoacetate (6.6 g, 3.0 eq) and THF (125 mL) were added to a 250 mL three-necked flask; under nitrogen protection, the system was heated to reflux; pyridine hydrochloride (210 mg, 0.1 eq) was added to the three-necked flask; under nitrogen protection, the system was heated to 75±5° C. (internal temperature 60-63° C.) and reacted for 8 hours. HPLC monitoring showed the compound of formula II was completely transformed. The purity of the compound of formula I in the residual reaction liquid is 93.1%.

The system was cooled to room temperature, the reaction liquid in the system was concentrated with a rotary evaporator until there was basically no fraction flowing out; water (50 mL) was added to the system, the pH value of the system was adjusted to 9-10 with a 4M sodium hydroxide solution; the system was extracted with ethyl acetate (50 mL), filterred, the filter cake was washed with ethyl acetate (10 mL) to obtain 3.5 g of a compound of formula I filter cake wet product. LC-MS test showed the purity of the compound of formula I was 99.22%; the filtrate obtained by filtration and washing was separated, the aqueous phase was extracted with ethyl acetate (50 mL), the organic phases were combined, and concentrated to dryness to obtain 2.8 g of a compound of formula I crude product. LC-MS test showed the purity of the compound of formula I was 95.08%.

MS-ESI: [M+1]$^+$: 297.0

$^1$H NMR(400 MHz, DMSO): 8.78 (s, 1H), 8.32 (d, 1H), 7.25 (d, 1H), 4.60 (m, 1H), 4.10-4.13 (t, 2H), 3.91 (m, 1H), 2.93-2.98 (m, 1H), 2.80-2.86 (m, 1H), 2.84 (s, 3H), 2.50 (m, 1H), 2.16-2.19 (m, 1H), 1.99-2.02 (m, 1H), 1.69-1.77 (m, 1H).

Example 22

Preparation of a Compound of Formula I

A compound of formula II (54 g, 1.0 eq), trimethyl orthoacetate (71.5 g, 3.0 eq) and THF (1.35 L) were added to a 3 L three-necked flask; under nitrogen protection, the system was heated to reflux; pyridine hydrochloride (2.27 g, 0.1 eq) was added to the three-necked flask; under nitrogen protection, the system was heated to 75±5° C. (internal temperature 60-63° C.) and reacted for 8 hours. HPLC monitoring showed 1.5% of the compound of formula II was left in the system; the system was cooled to room temperature, and trimethyl orthoacetate (11.9 g, 0.5 eq) and pyridine hydrochloride (1.14 g, 0.05 eq) was supplemented to the system; under nitrogen protection, the system was heated to 75±5° C. (internal temperature 60-63° C.) and reacted for 4 hours. HPLC monitoring showed 0.4% of the compounf of formula II was left in the system, the purity of the compound of formula II in the reaction liquid of the system was 91.6%.

The system was cooled to room temperature, the reaction liquid in the system was concentrated with a rotary evaporator until there was basically no fraction flowing out; water (540 mL, 10V) was added to the system, the pH value of the system was adjusted to 9-10 with a 4M sodium hydroxide solution; the system was filtered, the filter cake was washed with water (270 mL) and then MTBE (270 mL), the obtained filter cake was dried under vacuum at 50° C. for 16 hours to obain 56 g of a compound of formula II crude product, with an HPLC purity of 96.32%; the obtained crude product was dissolved in 600 mL of methanol until the solution was clear, a silicon based metal eliminator (43 g) and an activate carbon (5.4 g) were added to the system, the mixture was heated to reflux and the temperature was maintained for 1 hour (internal temperature 50° C.); the system was cooled to room temperature, filterred with diatomite, washed with methanol (15 mL) until the filtrate does not show fluorescence; the methanol solution was concentrated to dryness and the dropping speed of the distillate became slower, MTBE (540 mL) was added to the obtained solids, the system was heated to 50° C. and allowed for reflux and was then stirred for 1 hour until the solids were completely dissoved; the system was cooled to 10-15° C. and was stirred for 1 hour, filterred, the filter cake was washed with cold MTBE (100 mL); the obtained filter cake was dried under vacuum at 50° C. for 16 hour to obtain 28.0 g of a compound of formula I with an HPLC purity of 98.8%.

The compound of formula I was recovered from the mother liquid;

The filtrate obtained in the previous step was concentrated to dryness to obtain about 23 g of light yellow solids; MTBE (230 mL) was added thereto, the temperature was raised to 50° C., and the system was allowed to reflux for 10 minutes; methanol was added to the system in divided doses, until the total amount of the methanol added was about 30 mL and the material was basically dissolved and the solution was clear; the system was cooled to 10-15° C. and was stirred for 1 hour; filterred, the filter cake was washesd with cold MTBE (50 mL); the filter cake was dried under vacuum at 50° C. for 16 hours to obtain 8.7 g of off-white solids of a compound of formula I, with an HPLC purity of 97.8%.

Further Purification:

The compound of formula I (11.7 g) with a purity of 97.8% obtained in the previous step and MTBE (60 mL) were added to a reaction flask, the system was triturated at room temperature for 4 hours, filtered, the filter cake was washed with MTBE (20 mL), and the filter cake was dried under vacuum at 50° C. for 16 hours to obtain 10.8 g of off-white compound of formula I, with an HPLC purity of 98.1%.

The MS-ESI and $^1$H NMR data of the above compound of formula I product are consistent with example 21.

Example 23

Preparation of a Compound of Formula I

A compound of formula II in THF (45 g, including about 1 g of the compound of formula II, 1 eq) that was not subjected to a post-treatment and was prepared in example 14 was added to a flask, and the solution was concentrated by a rotary evaporator to 3 mL. Toluene (5 mL) was added to the flask, was then subjected to rotary evaporation to 3 mL, the step was repeated twice to obtain black oily concentrated residues.

1.0 g of black oily concentrated residues obtained in the previous step trimethyl orthoacetate (1.32 g, 3.0 eq) and THF (25 mL) were added to a 100 mL three-necked flask; under nitrogen protection, the system was heated to reflux; pyridine hydrochloride (0.08 g, 0.2 eq) was added to the three-necked flask; under nitrogen protection, the system was heated to 65-70° C. (internal temperature) and reacted for 5 hours; sampled and tested. HPLC monitoring showed 0.48% of the compound of formula II in the reaction liquid was left, and the purity of the compound of formula I was 90.10%; allowed the system to reflux and reacted for 5 hours, sampled and tested. HPLC showed the compound of formula II in the reaction liquid was completely transformed, and the purity of the compound of formula I was 91.79%.

Example 24

Preparation of a Compound of Formula I

The compound of formula II in THF (450 g, including about 10.0 g of the compound of formula II, 1 eq) not subjected to a post-treatment and was prepared in example 14 was added to a flask, the solution was concentrated by a rotary evaporator to 20-30 mL. Toluene (50 mL) was added to the flask, the system was subjected to rotary evaporation to 20-30 mL, the step was repeated twice to obtain black oily concentrated residues, and the residues were dissolved in THF (20 mL, 2 V)I until the solution was clear.

The THF solution obtained in the previous step, trimethyl orthoacetate (13.2 g, 3.0 eq) and THF (230 mL) were added to a 500 mL three-necked flask; under nitrogen protection, the system was heated to reflux; pyridine hydrochloride (0.8 g, 0.2 eq) was added to the three-necked flask; under nitrogen protection, the system was heated to 65-70° C. (internal temperature) and reacted for 10 hours; sampled and tested. HPLC monitoring showed 0.7% of the compound of formula II in the reaction liquid was left, and the purity of the compound of formula I was 90.1%.

The system was cooled to room temperature, water (20 mL, 2 V) was added; the system was concentrated by a rotary evaporator until there was basically no fraction flowing out; water (100 mL, 10 V) was supplemented to the system; the pH value of the system was adjusted to 9 with saturated potassium carbonate solution; the system was filterred, the filter cake was washed with water (50 mL, 5 V) and MTBE (50 mL, 5 V) sequentially; the washed filter cake was dried under vacuum at 50° C. for 16 hours to obtain 9.2 g of earthy yellow compound of formula I crude product, with an HPLC purity of 89.7% and a crude product yield of 84.5%.

Purification of a Compound of Formula I:

The compound of formula I crude product (5.0 g) with a purity of 89.7% obtained in the previous step and ethanol (50 mL) were added to a flask, the system was stirred at room temperature for 20 minutes, until the materials were basically dissolved and the solution was clear; silica gel (5.0 g, 1×) was added to the system, the system was concentrated by a rotary evaporator to dryness for later use; the solid crude product obtained by the rotary evaporation was allowed to pass through a silica gel column (40 g, 8×), and the column was eluted with a mixed wolution of ethyl acetate and petroleum ether ($V_{EA}$:$V_{PE}$=2:1); through a TLC test, the fractions containing the compound of formula I were collected and concentrated to dryness to obtain 0.5 g of the compound of formula I with a purity of 96.5% and 3.2 g of light yellow compound of formula I with an HPLC purity of 99.3%.

The compound of formula I with an HPLC purity of 99.3% and MTBE (30 mL) were added to a flask, the system was heated to reflux, and allowed the system to reflux for 1 hour; the system was cooled to 5-10° C., the temperature was maintained and the system was stirred for 1 hour, filterred, the filter cake was washed with MTBE (5 mL), and the filter cake was dried under vacuum at 50° C. for 16 hours to obtain 2.8 g of light yellow to off-white solids of the compound of formula I, with an HPLC purity of 99.8%, without impurities with the content that was >0.1%. The total yield of the second and third steps was 47.3%.

Example 25

Preparation of a Compound of Formula I

The compound of formula II in THF (130 g, including about 56 g of the compound of formula II, 1 eq) not subjected to a post-treatment and was prepared in example 14 was added to a flask, the solution was exchanged by toluene (280 mL×2) and was concentrated to 120-130 mL, then was exchanged with THF (280 mL) and was concentrated to 120-180 mL, THF (500 mL) was added until the solid was dissolved and the solution was clear, the obtained sotluion was transferred to a 2 L three-necked flask, THF (700 mL) and trimethyl orthoacetate (74.0 g, 3.0 eq) were adde to the system; under nitrogen protection, the system was heated to 70-75° C. (internal temperature) and reacted for 10 hours; sampled and tested. HPLC monitoring showed 0.1% of the compound of formula II in the reaction liquid was left, and the purity of the compound of formula I was 93.2%.

The above reaction liquid was cooled to room temperature, some of the reaction liquid (corresponding to the amount that containing 55 g of the compound of formula II before the reaction) was taken, water (110 mL, 2 V) was added; the system was concentrated by a rotary evaporator to 110-160 mL (2-3 V); water (400 mL, 7 V) was added to the concentrated residue slowly; the system was stirred for 30 minutes at room temperature, water (440 mL, 8V) was then added, the system was stirred for 30 minutes at room temperature (25-30° C.); the pH of the system was adjusted to 8-9 with 50% potassium carbonate solution (1.5 g (the mas of all the solution)); the system was stirred for 30 minutes at room temperature (25-30° C.); the temperature of the system was cooled to 10-15° C., and the system was stirred for 2 hours under 10-15° C., and was subjected to suction filtration, the filter cake was dried at 50° C. for 24 hours to obtain 55 g earthy yellow compound of formula I with a purity of 96.6%, a content of 87.53%, and a content yield of a crude product of 80.4%.

Purification of a Compound of Formula I:

The compound of formula I crude product (55 g) with an HPLC purity of 96.6% obtained in the previous step, silica gel (110 g, 2×) and ethanol (500 mL) were added to a flask; the system was heated to 50° C., and was stirred for 30 minutes at 50° C.; the system was concentrated by a rotary evaporator until there was basically no fraction flowing out, then was exchanged with n-heptane (200 mL) to dryness, silica gel was mixed with the system, the system was eluted by a column packed with silica gel (550 g, 10×); the eluent was a mixed solution of ethyl acetate and n-heptane ($V_{EA}$: $V_{n-heptane}$=1:1 to pure EA); through a TLC test, compound of formula I component A and cross component B were collected.

The component A was concentrated by a rotary evaporator to about 100 mL, the concentrated residue was exchanged with about 200 mL of methanol twice, then was exchanged with MTBE (about 200 mL) twice, then about 300 mL of MTBE was added thereto; the system was heated to reflux and allowed the system to reflux for 1 hour, then the system was cooled to room temperature (25-30° C.), and was stirred at room temperature (1 hour); the system was cooled to 5-10° C., stirred between 5-10° C. for 2 hours, filterred, the filter cake was washed with MTBE (30 mL); the filter cake was dried under vacuum at 50° C. for 16 hours to obtain 37.6 g of light yellow solids of compound of formula I, with an HPLC purity of 99.85%, without impurities with a content that was >0.1%.

The component B was concentrated by a rotary evaporator to dryness, triturated with MTBE (50 mL) for 1 hour, the system was cooled to 5-10° C., stirred between 5-10° C. for 2 hours, filterred, the washed filter cakewas dried under vacuum at 50° C. for 16 hours to obtain 6 g of light yellow solids of the compound of formula I, with an HPLC purity of 99.35%, and with 2 impurities with a content that was >0.1%.

The above compound of formula I (4.8 g) with a purity of 99.35%, MTBE (50 mL) and ethanol (5 mL) were added to a flask, the system was heated to 55-60° C., after allowing the system to reflux for 0.5 hours, the system was cooled to room temperature (25-30° C.), stirred at room temperature for 1 hour; the system was cooled to 5-10° C., stirred between 5-10° C. for 2 hours, filterred, the filter cake was washed with MTBE (10 mL); the washed filter cake was dried under vacuum at 50-55° C. for 16 hours to obtain 4.0 g of the compound of formula I, with a purity of 99.75%, without impurities with a content that was >0.1%.

Example 26

Preparation of a Compound of Formula I

The compound of formula II in THF (14.5 g, containing about 5.0 g of the compound of formula II, 1 eq) not subject to post-treatment and was prepared in example 14 was added to a flask, the solution was exchanged with toluene (25 mL×2) and concentrated to about 10-15 mL, then was exchanged with THF (25 mL) and concentrated to about 10-15 mL, then THF (115 mL) was added until the solid was dissolved and the solution was clear, the obtained solution was trasnferred to a 500 L three-necked flask; trimethyl orthoacetate (6.6 g, 3.0 eq) was added to the system; under nitrogen protection, the system was heated until reflux; pyridine hydrochloride (0.42 g, 0.2 eq) was added to a three-necked flask; under nitrogen protection, the system was heated to 70-75° C. (internal temperature) and reacted for 15 hours; sampled and tested. HPLC showed 4.0% of the compound of formula II in the reaction liquid was left; trimethyl orthoacetate (0.5 g) and pyridine hydrochloride (0.1 g) were supplemented to the system, allowed the system to reflux between 70-75° C. (internal temperature) for 5 hours; sampled and tested. HPLC showed 0.05% of the compound of formula II in the reaction liquid was left and the purity of the compound of formula I was 92.80%.

Example 27

Preparation of a Compound of Formula I

The compound of formula II in THF (817 g, containing about 282.6 g of the compound of formula II, 1 eq) not subject to post-treatment and was prepared in example 14 was added to a flask, the solution was exchanged with toluene (about 1400 mL×2) and concentrated to about 550-850 mL, then was exchanged with THF (about 1400 mL×2) and concentrated to about 550-850 mL, THF (about 6500 mL) was added until the solid was dissolved and the solution was clear, the solution was transferred to a 10 L three-necked flask; trimethyl orthoacetate (374.0 g, 3.0 eq) was added to the system; under nitrogen protection, the system was heated to reflux; pyridine hydrochloride (24.0 g, 0.2 eq) was added to a three-necked flask; under nitrogen protection, the system was heated to 70-75° C. (internal temperature) and reacted for 12 hours; sampled and tested. HPLC showed 4.1% of the compound of formula II in the reaction liquid was left; the purity of the compound of formula I was 85.5%; trimethyl orthoacetate (22 g) and pyridine hydrochloride (1.4 g) were added to the reaction system; under nitrogen protection, the system was heated to 70-75° C. (internal temperature) and reacted for 5 hours; sampled and tested. HPLC showed 0.7% of the compound of formula II in the reaction liquid was left and the purity of the compound of formula I was 91.4%.

The reaction liquid obtained in the previous step was cooled to room temperature, 570 g of water was added thereto, the system was concentrated by a rotary evaporator to 600-900 mL (2-3 V), the concentrated residue was transferred to a 10 L flask, 2000 g of water (about 7V) was added thereto slowly, the system was stirred at room temperature for 1 hour, 2300 g of water (about 8 V) was then added, the system was stirred at room temperature (25-30° C.) for 1 houtr, the pH value of the system was adjusted to 8-9 with 50% potassium carbonate solution (8.5 g); the system was stirred at room temperature (25-30° C.) for 1 hour, the system was cooled to 10-15° C., and was stirred beetween 10-15° C. for 2 hours, filterred, the filter cake was washed with water (500 g); the washed filter cake was dried at 50° C. for 72 hours, sampled and the water content was tested. The water content tested with Karl Fischer method was 3.2%. 252 g of earthy yellow compound of formula I crude product was obtained, with an HPLC purity of 97.5%, a content of 89.8%, and a content yield of the crude product was 72.3%.

Purification of a Compound of Formula I:

252 g of the compound of formula I crude product obtained in the previous step and ethanol (1004 g, ~1000 mL) were added to a flask; the system was heated to 50-60° C., stirred between 50-60° C. for 30 minutes, until the material was basically dissolved and the solution was clear; the system was divided into two equal proportions, silica gel (252 g) was added to each proportion, each proportion was concentrated by a rotary evaporator until there was basically no fraction flowing out; each proportion was exchanged with n-heptane (272 g, ~400 mL) until there was basically no fraction flowing out for later use; a silica gel column was compacted and filled with silica gel (3000 g, 200-300 meshes) and n-heptane (5.4 kg, ~8 L), the crude product obtained in the previous step was separated by column chromatography, and eluted with a mixture of n-heptane and ethyl acetate (1:1 V/V, 15.5 kg, ~20 L; 1:2 V/V, 28.5 kg, ~35 L; 1:5 V/V, 25.5 kg, ~25 L) and pure ethyl acetate (62 kg, 70 L); through TLC test, compound of formula I component A and cross component B were collected.

The component A was concentrated by a rotary evaporator until there was basically no fraction flowing out; the concentrated residue was transferred to a 2000 mL flask, exchanged with MTBE (370 g, 500 mL) until there was basically no fraction flowing out; MTBE (1330 g, 1800 mL) was added to the concentrated residue; the system was heated to reflux and allowed the system to reflux for 1 hour; the system was cooled to room temperature (25-30° C.), stirred at room temperature (1 hour); cooled to 5-10° C., stirred between 5-10° C. for 2 hours; filterred, the filter cake was washed with MTBE (75 g, ~100 mL); the HPLC purity of the washed filter cake was 99.9%; the filter cake was dried under vacuum at 50° C. for 16 hours to obtain 190 g of the compound of formula I, with an HPLC purity of 99.9%, and a water content by a KF test of 0.07%.

The component B was concentrated by a rotary evaporator to dryness; the obtained solid was transferred to a 500 mL single-necked flask; the system was exchanged with MTBE (85 g, ~120 mL) until there was basically no fraction flowing out; MTBE (200 g, ~300 mL) and methanol (23 g, ~30 mL) were added to the concentrated residue; the system was heated to reflux and allowed the system to reflux for 1 hour; the system was cooled to room temperature (25-30° C.), stirred at room temperature (1 hour); cooled to 5-10° C., stirred between 5-10° C. for 1 hour; filterred, the filter cake was washed with MTBE (22 g, ~30 mL); the washed filter cake was tried under vacuum at 50° C. for 16 hours to obtain 20 g of light yellow solid of the compound of formula I, with an HPLC purity of 99.6%.

Example 28

Preparation of a Compound of Formula I

The compound of formula II in THF (27.0 g, containing about 5.0 g of the compound of formula II, 1 eq) prepared in example 19 was added to a flask, the solution was exchanged with toluene (25 mL×2) and was concentrated to about 10-15 mL; then was exchanged with THF (25 mL) and was concentrated to about 10-15 mL; THF (115 mL) was added until the solid was dissolved and the solution was clear, and the solution was transferred to a 500 mL three-necked flask; trimethyl orthoacetate (6.6 g, 3.0 eq) was added to the system; under nitrogen protection, the system was heated to reflux; pyridine hydrochloride (0.42 g, 0.2 eq) was added to a three-necked flask; under nitrogen protection, the system was heated to 70-75° C. (internal temperature) and reacted for 12 hours; sampled and tested. HPLC showed 0.19% of the compound of formula II in the reaction liquid was left, and the purity of the compound of formula I was 93.3%.

Example 29

Preparation of a Compound of Formula I

The compound of formula II in THF (5.40 g, containing about 1.0 g of the compound of formula II, 1 eq) prepared in example 19 was transferred to a flask, the solution was exchanged with toluene (4.3 kg×2) and concentrated to about 2 L, then was exchanged with THF (4.3 kg) and concentrated to about 2 L, after THF (19 kg) was added, the system was transferred into a 50 L reactor; trimethyl orthoacetate (1.32 kg, 3.0 eq) was added to the system; under nitrogen protection, the system was heated to reflux; pyridine hydrochloride (85.0 g, 0.2 eq) was added to a three-necked flask; under nitrogen protection, the system was heated to 70-75° C. (internal temperature) and reacted for 12 hours; sampled and tested. HPLC showed 4.22% of the compound of formula II in the reaction liquid was left; the purity of the compound of formula I was 80.30%, trimethyl orthoacetate (80 g) and pyridine hydrochloride (5 g) were supplemented to the reaction system, under nitrogen protection, the system was heated to 70-75° C. (internal temperature) and reacted for 5 hours; sampled and tested. HPLC showed 0.56% of the compound of formula II in the reaction liquid was left and the purity of the compound of formula I was 92.48%.

The reaction liquid of the previous step was cooled to 25° C., 2.0 kg of water was added; a distillation under reduced pressure was conducted at 45±5° C. to 2 L volume, 2 L of water was added to the rotary evaporation flask, tteh material liquid in the flask was transferred to a reactor, 5 kg of water was added slowly, stirred at 25° C. for 1 hour; 5 kg of water was added to the reactor, stirred at 25° C. for 1 hour; 32 g of 50% potassium carbonate solution was added to the reactor dropwise, the pH of the system was adjusted to 8-9, the system was stirred at 25° C. for 1 hour; the material liquid in the reactor was cooled to 10-15° C., stirred for 2 hours; the system was filterred, the filter cake was washed with 2 kg of water, and was then dried under vacuum at 45-55° C. for 48 hours to obtain 0.91 kg of the compound of formula I, with a water content of 0.2% tested with a KF method, an HPLC purity of 95.71%, a content of 85.39% and a content yield of 71.4%.

Purification of a Compound of Formula I:

The compound of formula I (0.91 kg) with an HPLC purity of 95.71% obtained in the previous step and ethanol (3.6 kg) were added to a 20 L rotary evaporation flask; the system was heated to 50-60° C., stirred between 50-60° C. for 30 minutes, the material was dissolved and the solution was basically clear; silica gel (1.82 kg) was added to the above rotary evaporation flask, the system wasconcentrated under reduced pressure between 50-60° C. to dry powder; n-heptane (1.82 kg) was added to the above rotary evaporation flask, the system wasconcentrated and exchanged between 40-50° C. to dry powder; an appropriate cleaned column was prepare, silica gel (11 kg, 200-300 meshes) was added to the column, the column was compacted with nitrogen; n-heptane (27 kg) was added to the column and the column was compacted with nitrogen; the silica gel-like compound of formula I concentrated to dryness in the previous step was added to the column, the column was eluted with n-heptane (18 kg), a mixture of n-heptane/ethyl acetate (1:1 V/V, 72 kg; 1:2 V/V, 158 kg; 1:5 V/V, 142 kg), a mixture of n-heptane/ethyl acetate (1:5 V/V, 70 kg), a mixture of n-heptane/ethyl acetate (1:5 V/V, 175 kg), and ethyl acetate (205 kg) sequentially, a TLC test was conducted, and a compound of formula I component A and cross component B were collected.

The component A was added to a 50 L reactor, the system was concentrated under vacuum at 40-50° C. to the minimum stirring volume (~6 L); MTBE (5.0 kg×5) was added to the reactor, the system was concentrated and exchanged 5 times; MTBE (1.2 kg) was added to the reactor, the system was heated to reflux (50-60° C.), and allowed the system to reflux for 1 hour with the temperature maintained; the system was cooled to 20-30° C., and was stirred (1 hour) with the temperature maintained; the system was cooled to 5-10° C., stirred between 5-10° C. for 2 hours; filterred, the filter cake was washed with MTBE (0.25 kg); 0.62 kg of athe compound of formula I was obtained, with an HPLC purity of 100.0%; the filter cake was dried at 50° C. for 16 hours to obtain 0.55 kg of the compound of formula I, with a water content of 0.04% tested by a KF method and a Pd residue<2 ppm.

The component B was added to the reaction flask, the system was concentrated under vacuum in a 45-50° C. water bath to the minimum stirring volume (about 1 L); MTBE (1.5 kg×2) was added to the reaction flask, the system was heated in a 45-50° C. water bath, distilled under vacuum to the minimum stirring volume, exchanged twice; MTBE (1.5 kg) and absolute ethanol (0.14 kg) were added to the reaction flask, the system was heated to 50-60° C., stirred for 1 hour; the material liquid in the reaction flask was cooled to 20-25° C., the system was stirred for 1 hour with the temperature maintained ; cooled, the temperature of the material liquid in the reaction flask was lowered to 6-10° C., the temperature was maintained and the system was stirred for 2 hours; filterred, the filter cake was washed with MTBE (0.24 kg); the filter cake, MTBE (1.5 kg)/absolute ethanol (0.14 kg) were added to the reaction flask; the system was stirred, heated to raise the temperature to 50-60° C., stirred for 1 hour with the temperature maintained; cooled, the temperature of the material liquid in the reaction flask was lowered to 20-25° C., the temperature was maintained and the system was stirred for 1 hour; cooled, the temperature of the material liquid in the reaction flask was lowerred to 6-10° C., the temperature was maintained, and the system was stirred for 2 hours; filterred, the filter cake was washed with MTBE (0.24 kg); 115 g of wet products were obtained, with an HPLC purity of 99.8%, and a maximum individual impurity content of 0.09%; the wet products were dried betweeen 45-55° C., under a vacuum degree≤–0.080 MPa for 16 hours; 0.10 kg of the compound of formula I was obtained, with a water content of 0.08% tested with a KF method, an HPLC purity of 99.8%, a maximum individual impurity content of 0.09%, and a Pd residue≤2 ppm.

Unless otherwise specified, the compound of formula I finally purified and prepared in example 27 is taken as the starting material in the following examples.

Preparation of Crystal Form 1 of a Compound of Formula I

Example 30

The wet product and the crude product of the filter cake of the compound of formula I obtained in example 21 were combined, dissolved with methanol (40 mL); a silicon based metal eliminator (4.0 g) and an activated carbon (1.0 g) were added to the methanol solution, the system was heated to 50° C. and stirred for 1 hour; the system was cooled to 10±5° C. and was stirred at the temperature for 0.5 hour; filtered, the filter cake was washed with MTBE (15 mL); the filter cake was dried under vacuum at 50° C. for 16 hours to obtain 2.5 g of off-white solid of the compound of formula I, with an HPLC purity of 98.4%. Upon testing, the solid was crystal form 1 of a compound of formula I. See FIGS. 1-4 for the XRPD pattern, the DSC thermogram, the TGA thermogram and the DVS isotherm plot.

Preparation of Crystal Form A of a Hydrochloride of a Compound of Formula I

Example 31

Figure 6:
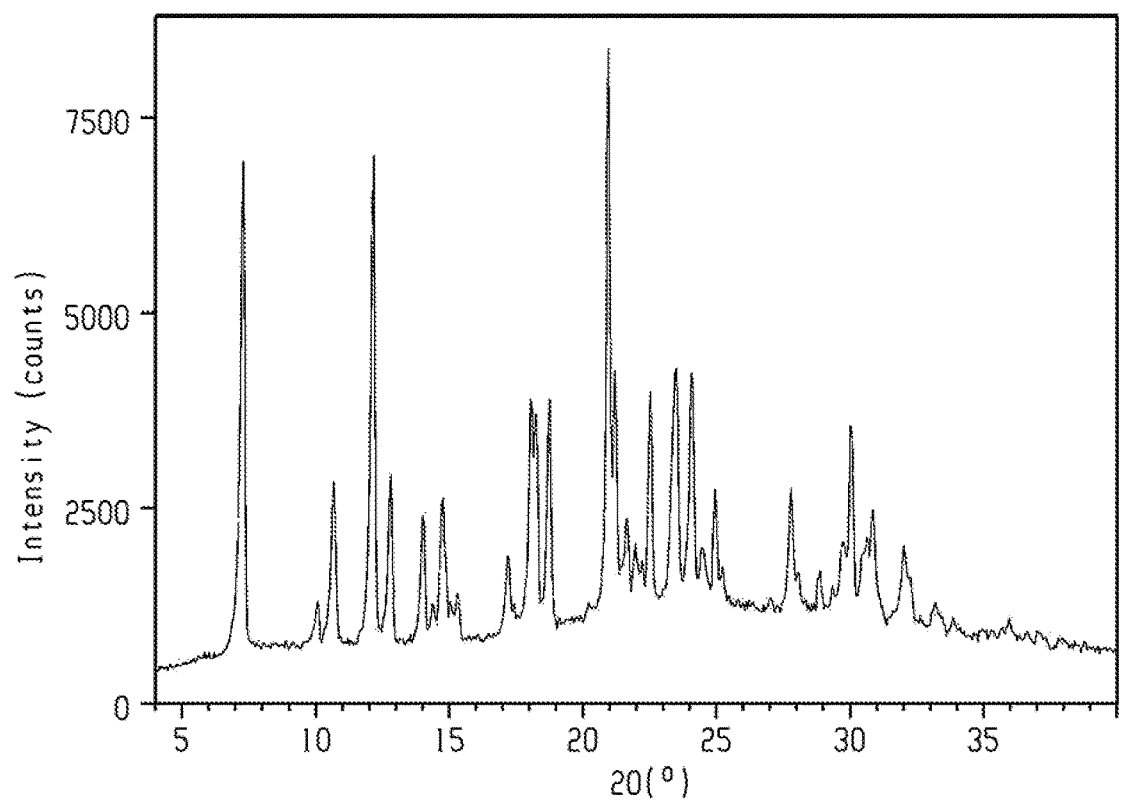
FIG. 6 is the XRPD pattern of crystal form A of a hydrochloride of a compound of formula I of the invention.
Figure 7:
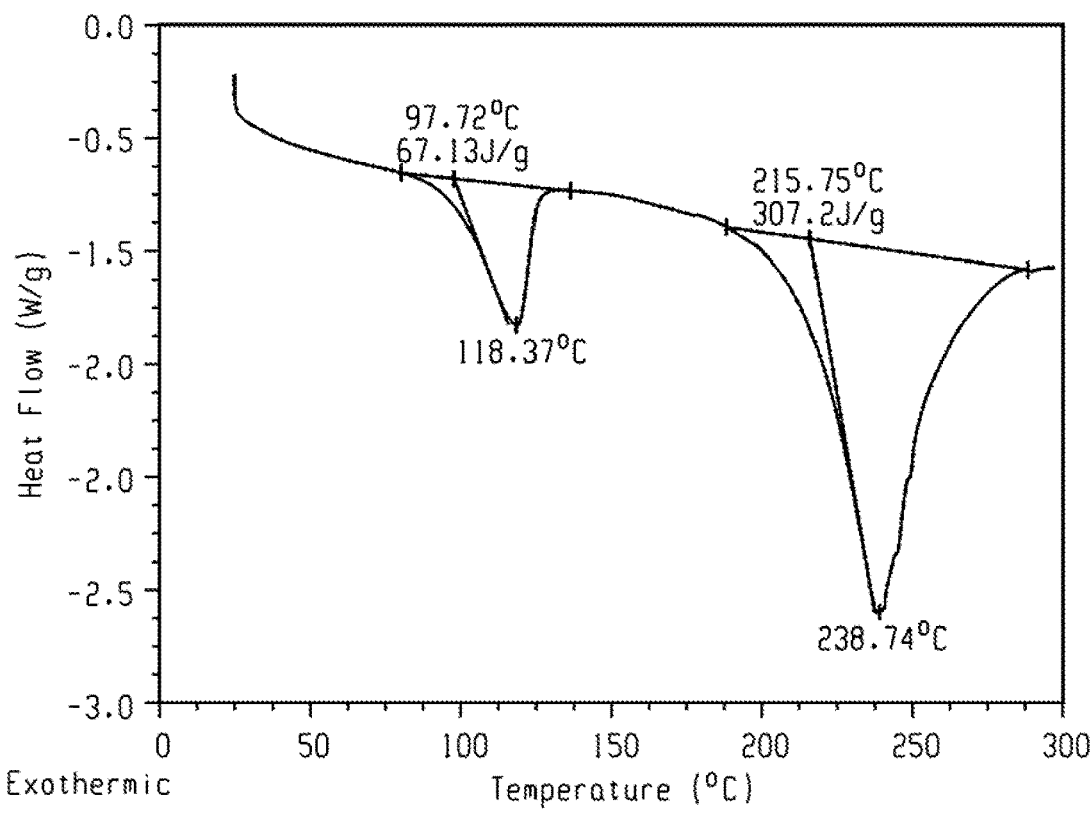
FIG. 7 is the DSC thermogram of crystal form A of a hydrochloride of a compound of formula I of the invention.

About 50 mg of a compound of formula I was weighed and placed into a small bottle, 2.5 mL of acetone was added, the system was subjected to ultrasonicationg and heating until the compound was completely dissolved, to prepare 20 mg/mL a compound of formula I in acetone. The sample bottle was placed on a magnetic stirring plate, magnetic stirring was conducted and 0.73 mL of hydrochloric acid in acetone (the concentration of the hydrochloric acid in acetone was 25 mg/mL) was slowly added dropwise, white precipitates were produced, bottle cap was covered tightly at room temperatureand the system was stirred for 1 day, the suspension was then cnetrifuged, and the collected solid was dried under vacuum at 40° C. overnight to obtain compound of formula I hydrochloride solid. Upon testing, the solid was crystal form A of a hydrochloride of a compound of formula I. See FIGS. 6 and 7 for the XRPD pattern and the DSC thermogram.

Preparation of Crystal Form B of a Hydrochloride of a Compound of Formula I

Example 32

Figure 8:
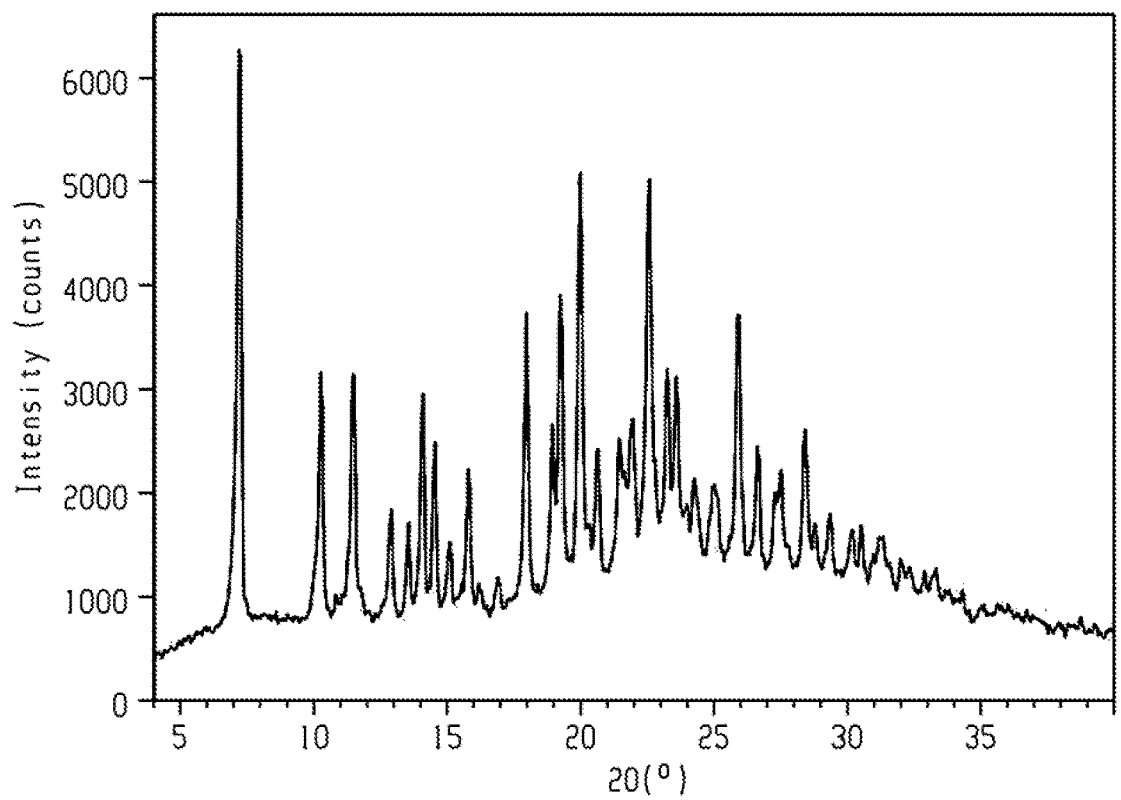
FIG. 8 is the XRPD pattern of crystal form B of a hydrochloride of a compound of formula I of the invention.
Figure 9:
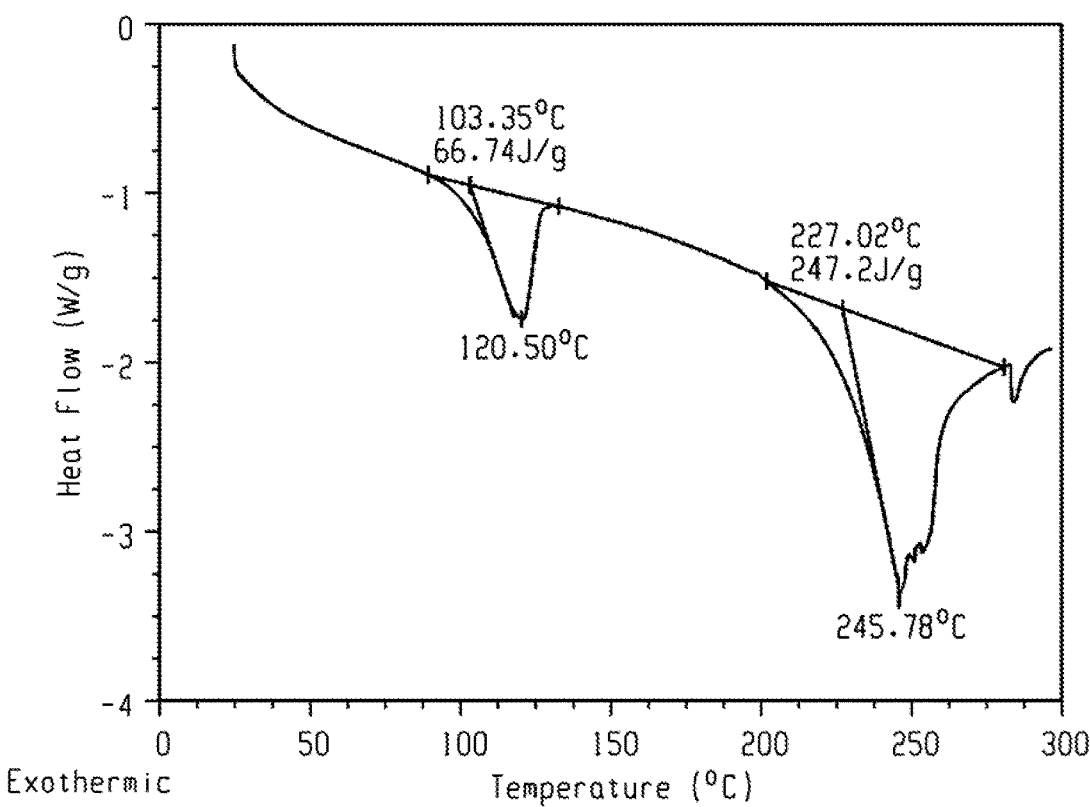
FIG. 9 is DSC thermogram of crystal form B of a hydrochloride of a compound of formula I of the invention.

About 50 mg of a compound of formula I was weighed and palced into a small bottle, 2.5 mL of ethyl acetate was added, the system was subjected to ultrasonication and heating until the compound was completely dissolved, to prepare 20 mg/mL a compound of formula I in ethyl acetate. The sample bottle was placed on a magnetic stirring plate, magnetic stirring was conducted and 0.73 mL of hydrochloric acid in ethyl acetate (the concentration of the hydrochloric acid in ethyl acetate was 25 mg/mL) was slowly added dropwise, white precipitates were produced, the bottle cap was covered tightly at room temperature, the system was stirred for 1 day, the suspension was then centrifuged, and the collected solid was dried under vacuum at 40° C. overnight to obtain acompound of formula I hydrochloride solid. Upon testing, the solid wascrystal form B of a hydrochloride of a compound of formula I. See FIGS. 8 and 9 for the XRPD pattern and the DSC thermogram.

Preparation of a Compound of Formula I Hydrochloride Crystal Form C

Example 33

Figure 10:
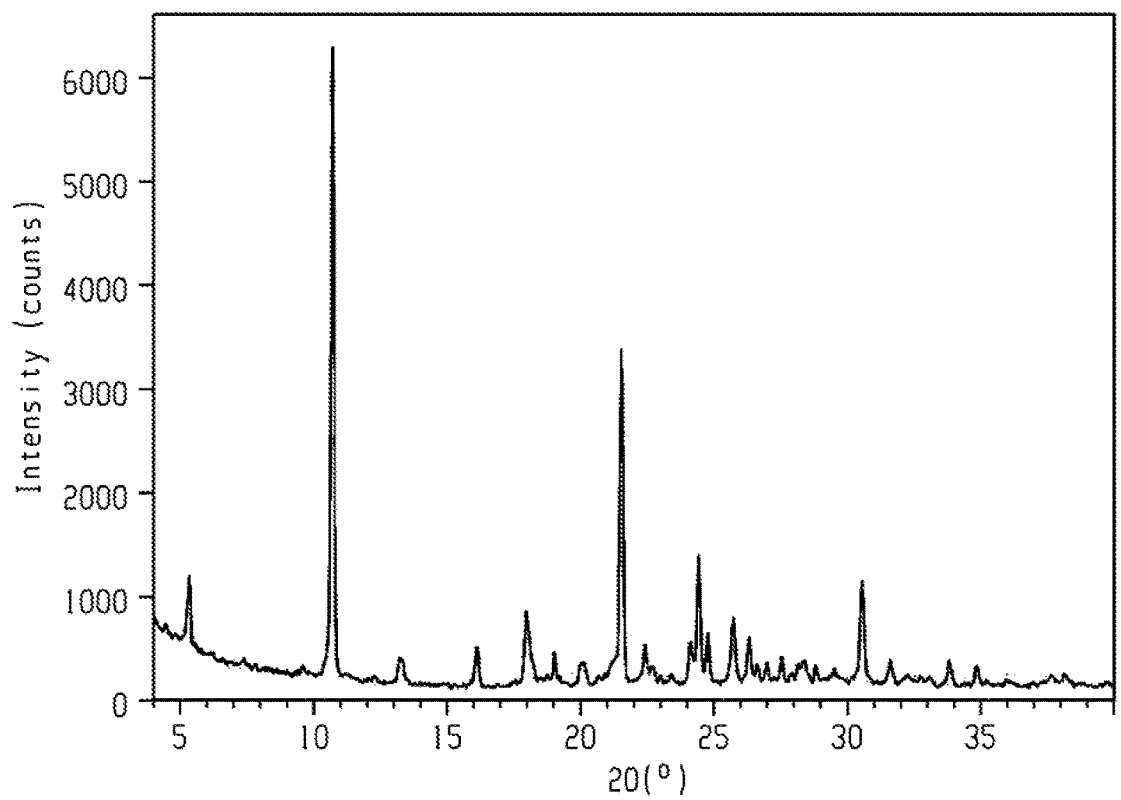
FIG. 10 is the XRPD pattern of crystal form C of a hydrochloride of a compound of formula I of the invention.
Figure 11:
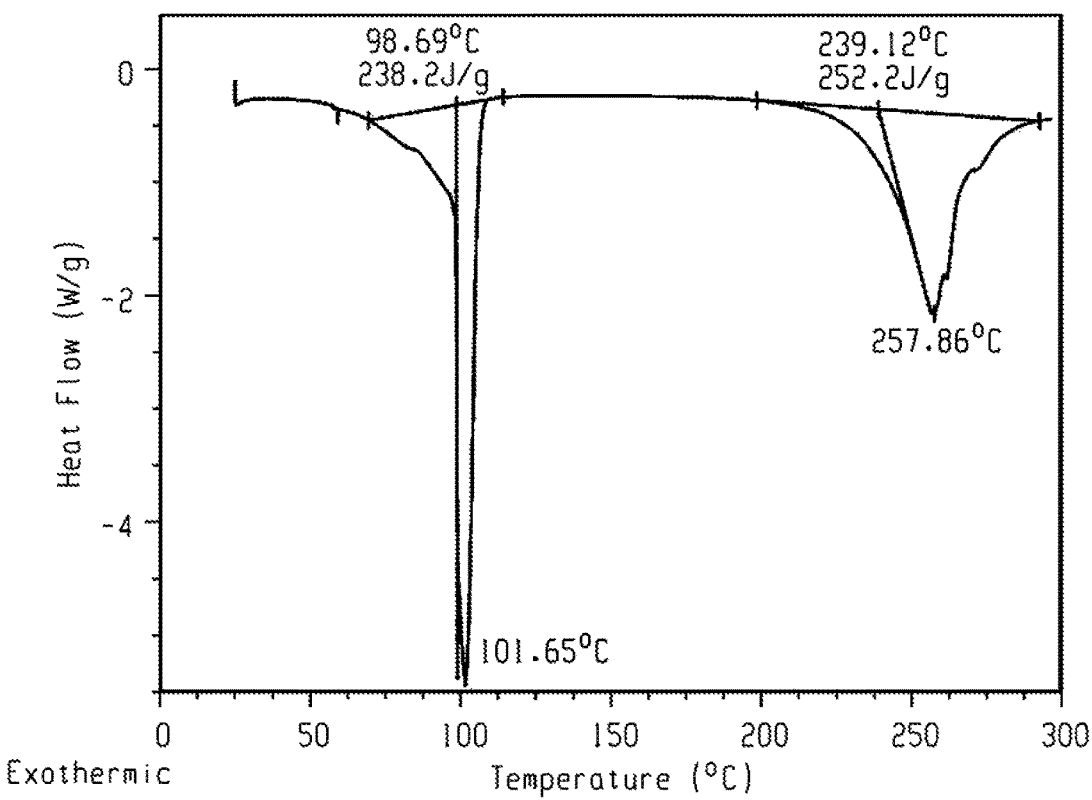
FIG. 11 is the DSC thermogram of crystal form C of a hydrochloride of a compound of formula I of the invention.

5 mg of crystal form A of a hydrochloride of a compound of formula I prepared in example 31 was weighed and placed into a small bottle, a suitable amount of methanol was added, magnetic stirring of the sample suspension obtained was conducted at room temperature overnight, the system was centrifuged to separate the solid and liquid, the solid was collected, and dried under vacuum overnight at 40° C. to obtain a compound of formula I hydrochloride solid. Upon testing, the solid was crystla form C of a hydrochloride of a compound of formula I. See FIGS. 10 and 11 for the XRPD pattern and the DSC thermogram.

Examples 34-36

The crystallization method that was the same as that in example 33 was adopted. The solvent was changed to acetonitrile, n-heptane and methyl ethyl ketone to prepare crystal form C of a hydrochloride of a compound of formula I. Upon testing, the XRPD pattern of the solid compounds prepared in examples 34-36 are consistent with FIG. 10.

Preparation of Crystal Form D of a Sulfate of a Compound of Formula I

Example 37

Figure 12:
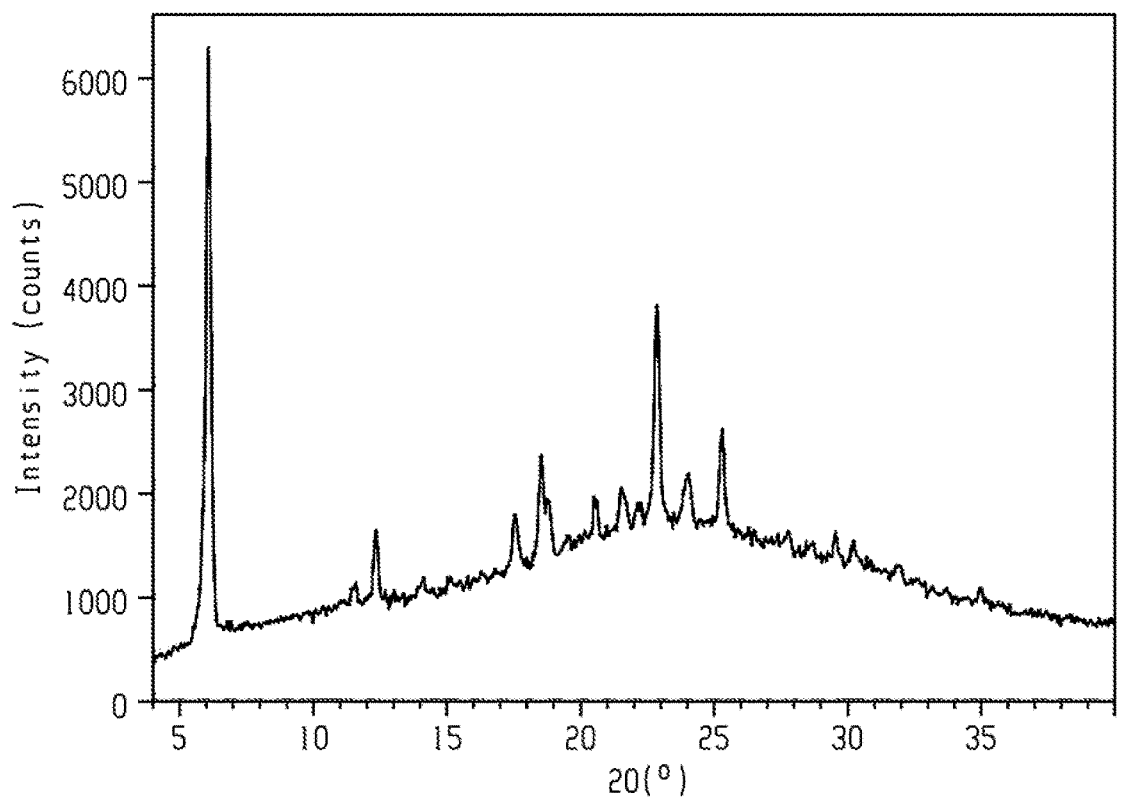
FIG. 12 is the XRPD pattern of crystal form D of a sulfate of a compound of formula I of the invention.
Figure 13:
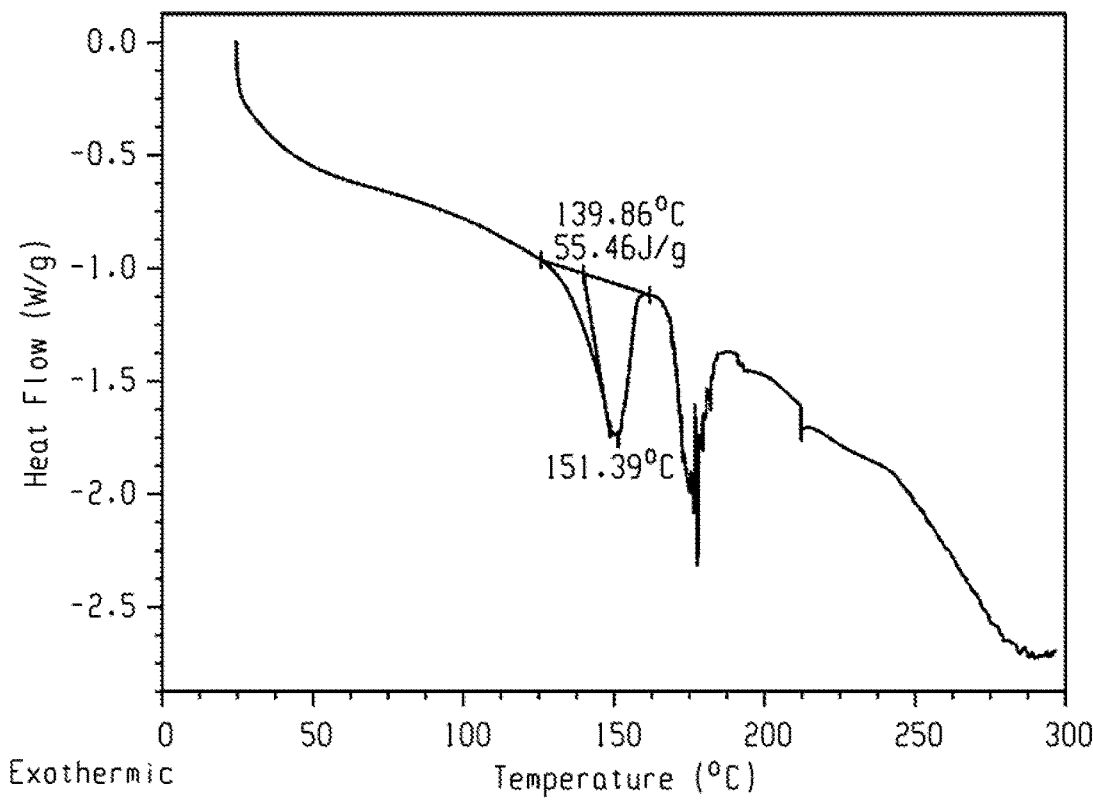
FIG. 13 is the DSC thermogram of crystal form D of a sulfate of a compound of formula I of the invention.

About 50 mg of a compound of formula I was weighed and placed into a small bottle, 2.5 mL of acetone was added, the system was subjected to ultrasonication and heating until the compound was completely dissolved, to prepare 20 mg/mL a compound of formula I in acetone. The sample bottle was placed on a magnetic stirring plate, magnetic stirring was conducted and 0.77 mL of sulfuric acid in acetone (the concentration of the sulfuric acid in acetone was 25 mg/mL), white precipitates were produced, the bottle cap was covered tightly at room temperature, the system was stirred for 1 day, the suspension was then centrifuged, the collected solid was dried under vacuum at 40° C. overnight to obtain compound of formula I sulfate solid. Upon testing, the solid was crystal form D of a sulfate of a compound of formula I. See FIGS. 12 and 13 for the XRPD pattern and the DSC thermogram.

Preparation of Crystal Form E of a Phosphate of a Compound of Formula I

Example 38

Figure 14:
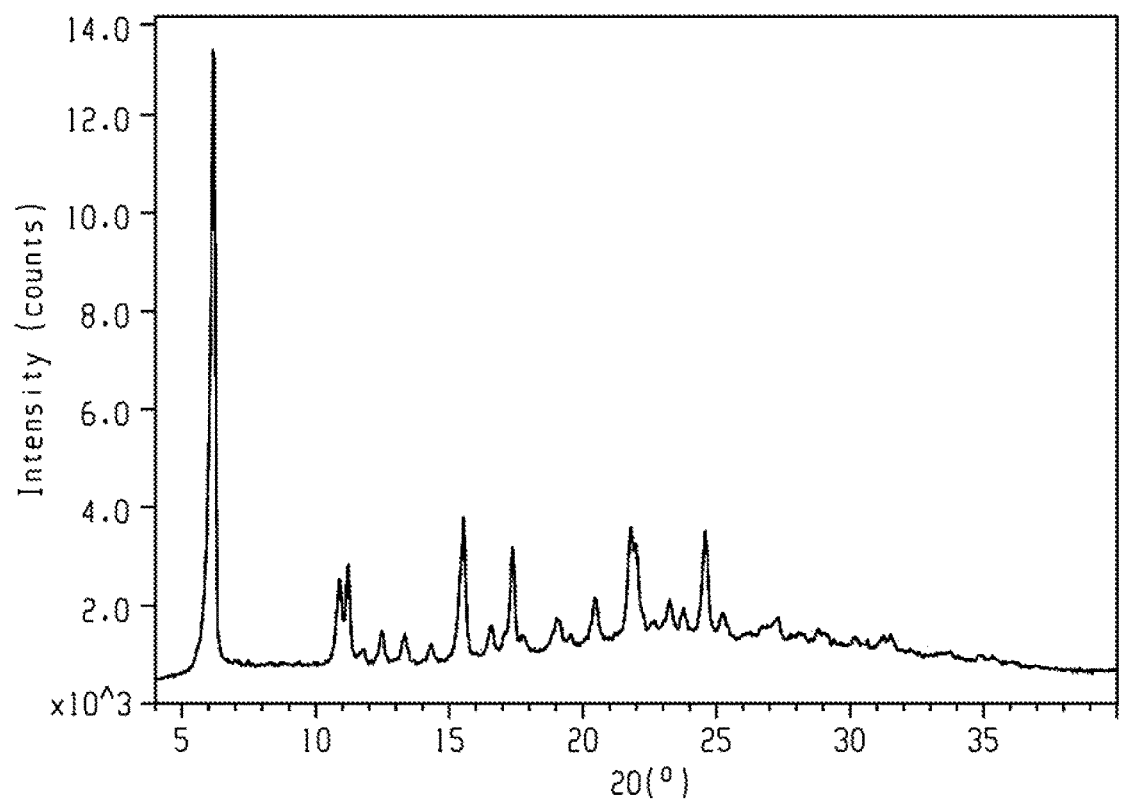
FIG. 14 is the XRPD pattern of crystal form E of a phosphate of a compound of formula I of the invention.
Figure 15:
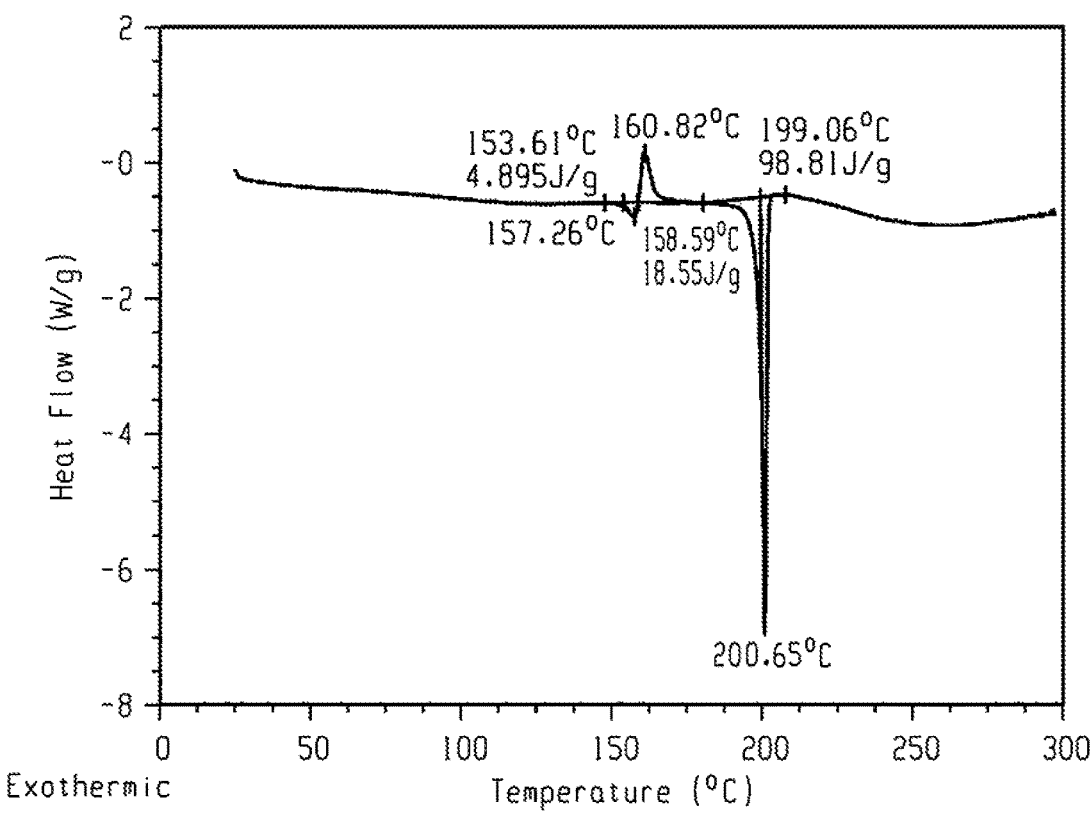
FIG. 15 is the DSC thermogram of crystal form E of a phosphate of a compound of formula I of the invention.
Figure 16:
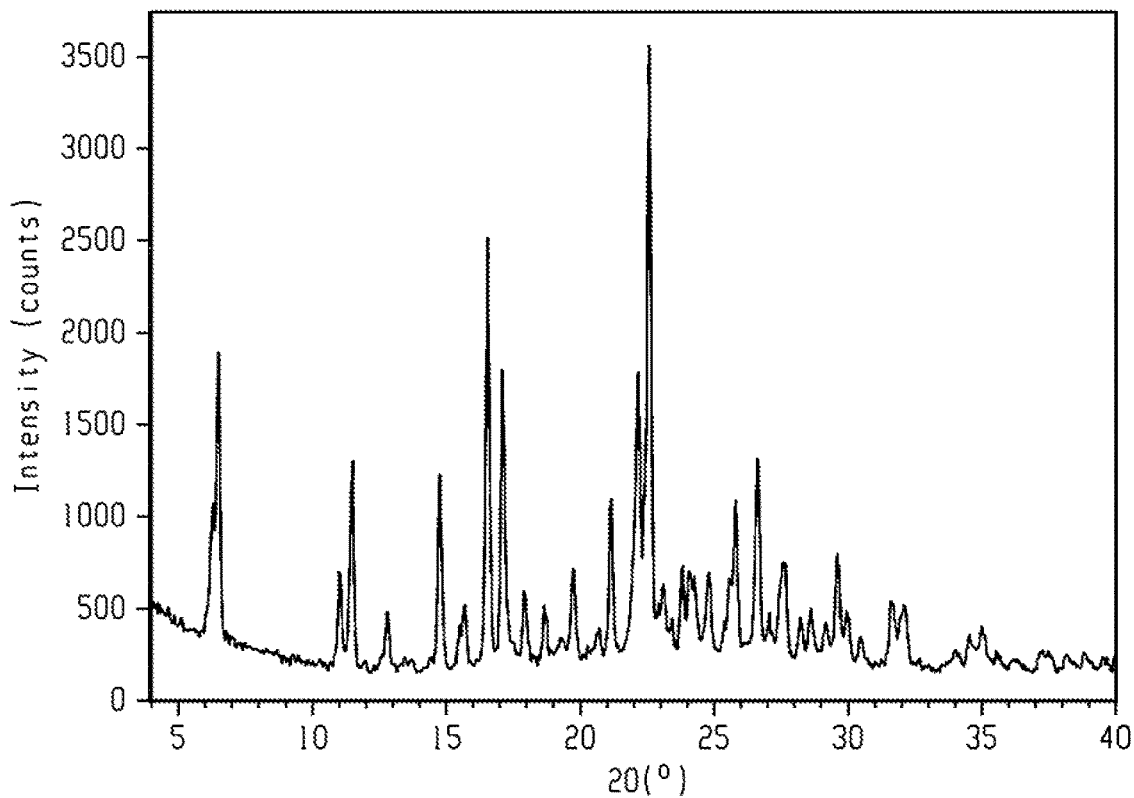
FIG. 16 is the XRPD pattern of crystal form F of a phosphate of a compound of formula I of the invention.
Figure 17:
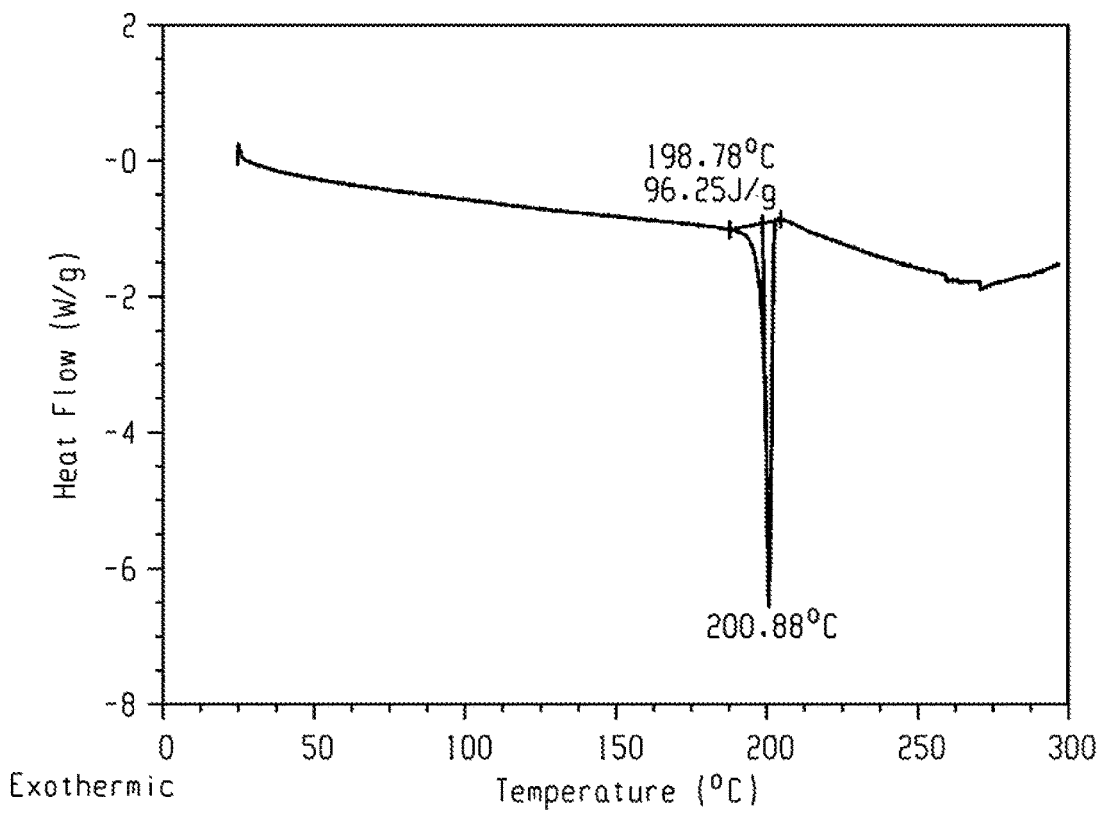
FIG. 17 is the DSC thermogram of crystal form F of a phosphate of a compound of formula I of the invention.
Figure 18:
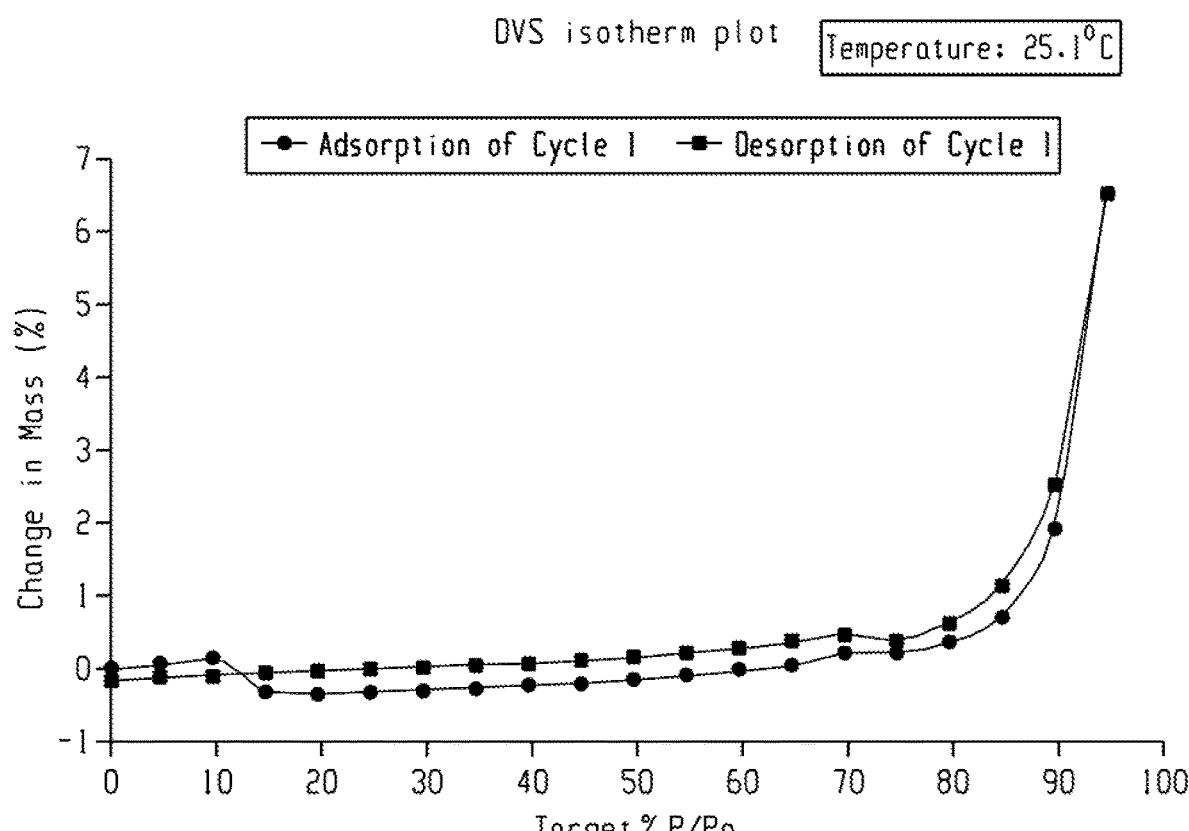
FIG. 18 is the DVS isotherm plot of crystal form F of a phosphate of a compound of formula I of the invention.
Figure 19:
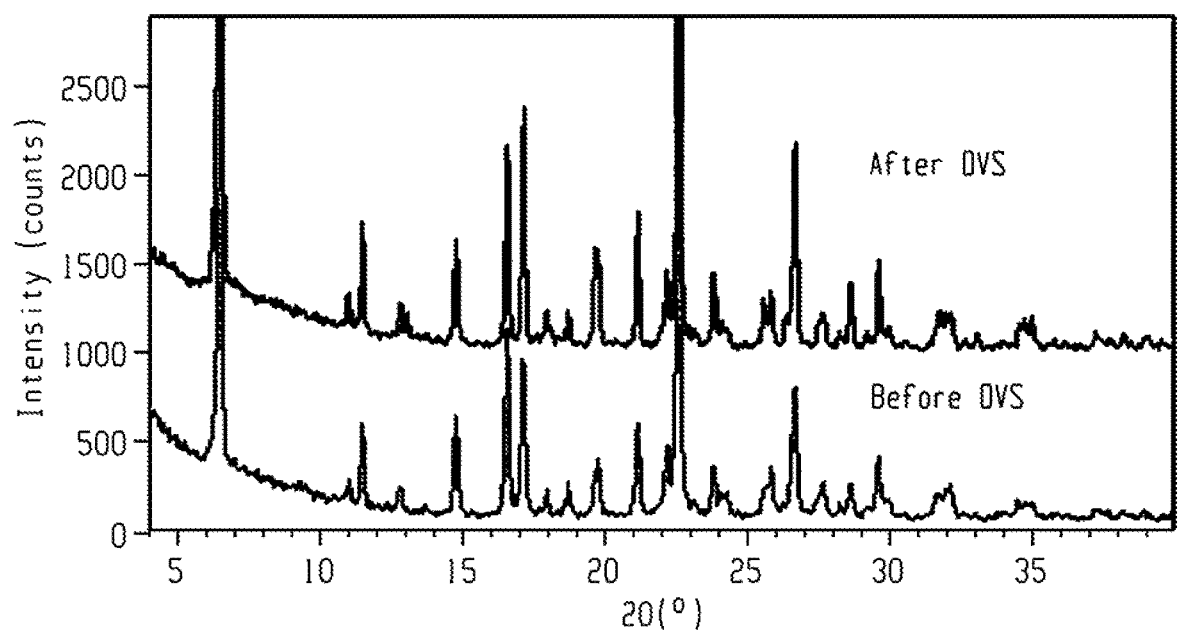
FIG. 19 is the XRPD overlay pattern of crystal form F of a phosphate of a compound of formula I of the invention before and after the DVS test.

About 50 mg of a compound of formula I was weighed and palced into a small bottle, 2.5 mL of acetone was added, the system was subjected to ultrasonication and heating until the compound was completely dissolved, to prepare 20 mg/mL a compound of formula I in acetone. The sample bottle was placed on a magnetic stirring plate, magnetic stirring was conducted and 0.86 mL of phosphoric acid in acetone (the concentration of the phosphoric acid in acetone was 25 mg/mL) was slowly added dropwise, white precipitates were produced, the bottle cap was covered tightly at room temperature, the system was stirred for 1 day, the suspension was then centrifuged, and the collected solid was dried under vacuum at 40° C. overnight to obtain compound of formula I phosphate solid. Upon testing, the solid wascrystal form E of a phosphate of a compound of formula I. See FIGS. 14 and 15 for the XRPD pattern and the DSC thermogram.

The salt-forming percentage test of crystal form E of a phosphate of a compound of formula I was conducted with ion chromatography:

About 0.5 g of crystal form E of a phosphate of a compound of formula I was weighed and placed into a liquid phase small bottle, completely dissolved with 1 mL of water, then was used as a sample solution. The bulk (1000 ppm) of phosphoric acid standard solution was diluted at 10 and 20 folds with water, to obtain 100 ppm and 50 ppm standard sample solution respectively.

Ion chromatography tests were conducted on the the sample solution and the standard solution, respectively, see Table 16 for the test method. A standard curve was plotted with the peak area of the countra-ion on the ion chromatogram corresponding to the concentration of the countra-ion in the standard sample solution, the concentration of the countra-ion in each sample was calculated using an external standard method, the content of the countra-ion in crystal form E of a phosphate of a compound of formula I was calculated, to determine the salt-forming percentage of a compound of formula I and the corresponding countra-ion in crystal form E of a phosphate of a compound of formula I.

TABLE 16

| Ion chromatography determination method | |
|---|---|
| Instrument model | ICS-2000 + AS40 Automated sampler |
| Chromatographic column | IonPac ®ASl 1-HC 4 × 250 mm |
| Column temperature | 30° C. |
| Eluent | 10 Mm KOH solution |
| Flow rate | 1.00 mL/min |
| Suppressor | Dionex AERS 500 4 mm |
| Electric current of suppressor | 25 mA |
| Run time | 15 min |

See Table 17 for the countra-ion content in crystal form E of a phosphate of a compound of formula I. In the 0.5 g of crystal form E of a phosphate of a compound of formula I, the compound of formula I and phosphoric acid were fed at a molar ratio of 1:1.1 and reacted. The actually measured content of phosphate anion in the obtained phosphate was 25.6%, which was basically consistent with the theoretical content of 24.9%. The salt-forming molar ratio was 1:1.04 (the compound of formula I:phosphoric acid).

TABLE 17

Countra-ion content determination results in crystal
form E of a phosphate of a compound of formula I

| Sample name | Countra-ion at different salt-forming percentage Theoretical content % | Measured countra-ion content % |
|---|---|---|
| Crystal form E of a phosphate of a ompound of formula I | Free base:phosphoric acid = 24.9% 1:1 salt formation | 25.6% |

Example 39

5 mg of crystal form E of a phosphate of a compound of formula I prepared in example 38 was weighed and placed into a small bottle, a suitable amount of methanol was added, magnetic stirring of the sample suspension was conducted at room temperature overnight, the system was centrifuged and the solid and liquid were separated, the solids were collected, and dried under vacuum overnight at 40° C. to obtain a compound of formula I phosphate solid. Upon testing, the solid was still crystal form E of a phosphate of a compound of formula I. Its XRPD pattern is consistent with FIG. 14.

Examples 40-42

The method that was the same as that in example 39 was adopted. The solvent was changed to acetonitrile, n-heptane and methyl ethyl ketone to prepare crystal form E of a phosphate of a compound of formula I. Upon testing, the XRPD pattern of the solid compounds prepared in examples 40-42 were consistent with FIG. 14.

Preparation of Crystal Form F of a Phosphate of a Compound of Formula I

Example 43

About 500 mg of a compound of formula I was weighed and palced into a small bottle, 20 mL of acetone was added, the system was subjected to ultrasonication and heating until the sample was completely dissolved to obtain 25 mg/mL a compound of formula I in acetone. The sample bottle was placed on a magnetic heating stirrer, magnetic stirring was conducted and 8.57 mL of phosphoric acid in acetone (the concentration of the phosphoric acid in acetone was 25 mg/mL) was slowly added dropwise overnight. The suspension was subjected to suction filtration, the solids were dried under vacuum at 50° C., and the solid were collected and placed into a 100 mL glass bottle. Methanol was slowly added dropwise, magnetic stirring was conducted at room temperature, until the solution was clear, and then the solution was diluted with anti-solvent acetic acid isopropyl ester at 10 folds. The system was stirred overnight and the suspension was filterred, the solids were vacuum dried at 50° C., and the solids were collected to obtain compound of formula I phosphate solids. Upon testing, the solid was crystal form F of a phosphate of a compound of formula I. See FIGS. 16-19 for the XRPD pattern, the DSC thermogram, and DVS isotherm plot and the XRPD pattern after the DVS test.

Preparation of Crystal Form G of a Mesylate of a Compound of Formula I

Example 44

Figure 20:
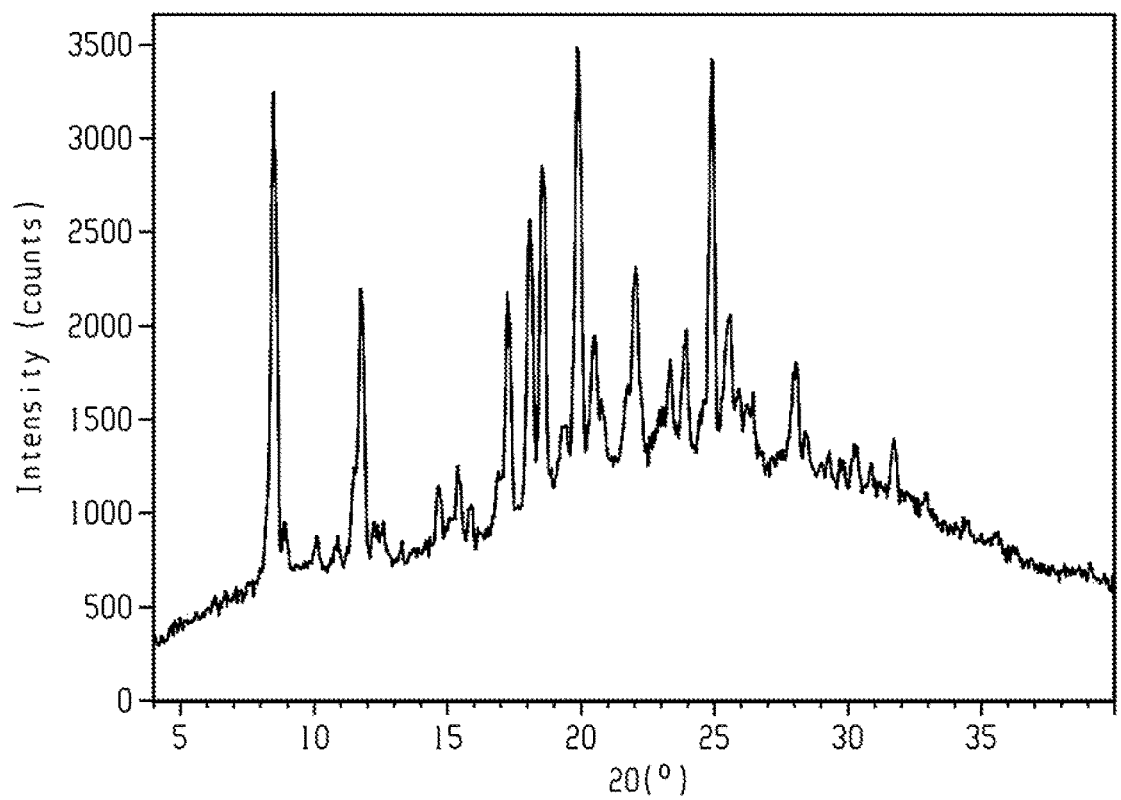
FIG. 20 is the XRPD pattern of crystal form G of a mesylate of a compound of formula I of the invention.
Figure 21:
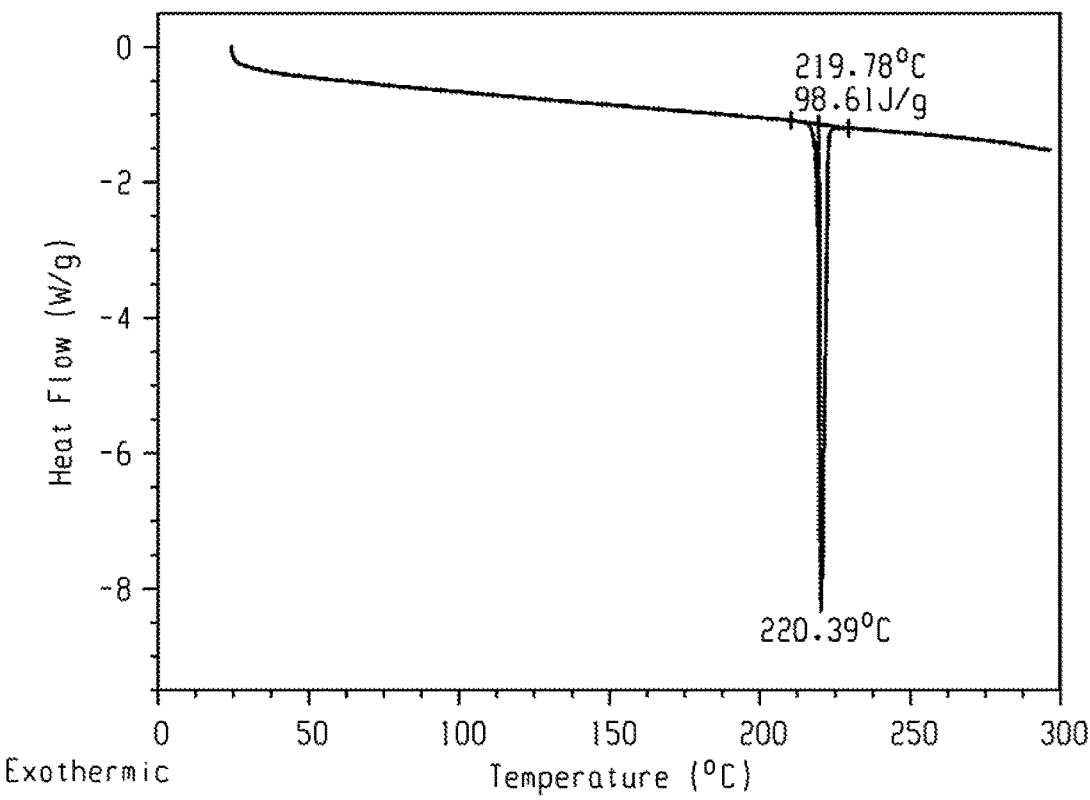
FIG. 21 is the DSC thermogram of crystal form G of a mesylate of a compound of formula I of the invention.
Figure 22:
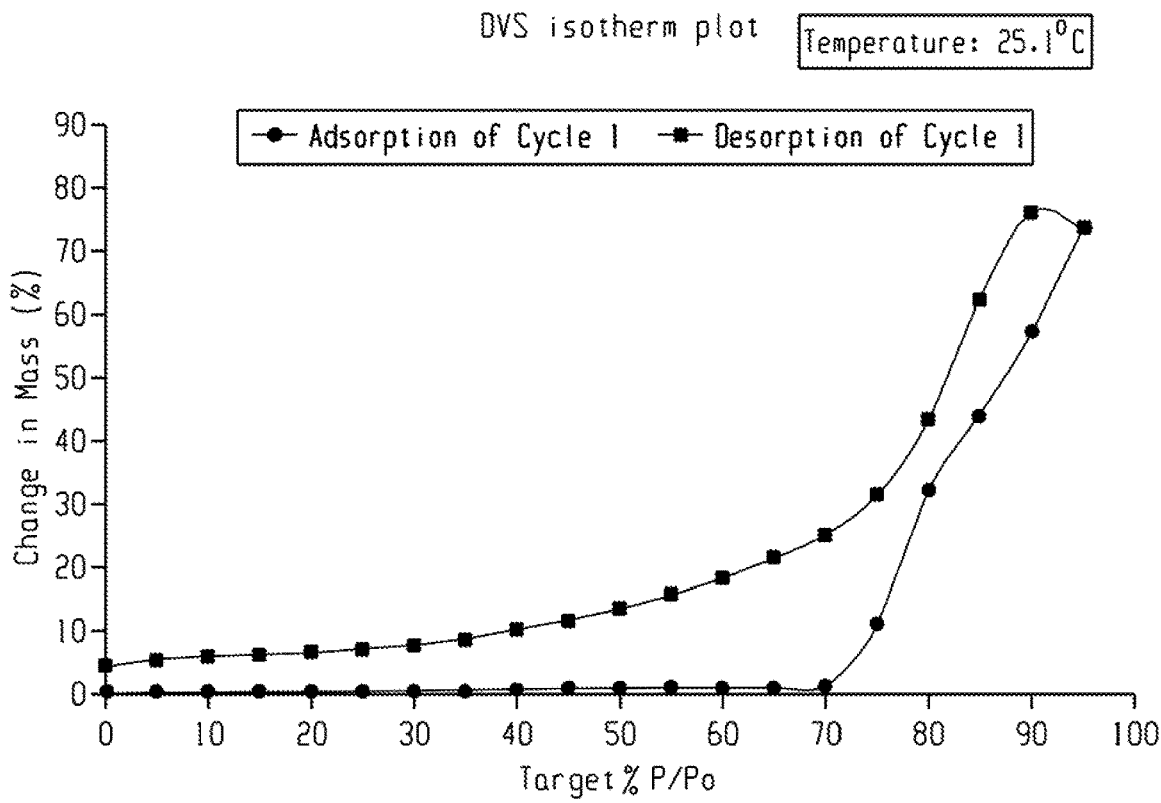
FIG. 22 is the DVS isotherm plot of crystal form G of a mesylate of a compound of formula I of the invention.

About 50 mg of a compound of formula I was weighed and placed into a small bottle, 2.5 mL of acetone was added, the system was subjected to ultrasonication and heating until the compound was completely dissolved, to prepare 20 mg/mL a compound of formula I in acetone. The sample bottle was placed on a magnetic stirring plate, magnetic stirring was conducted and 0.73 mL of methanesulfonic acid in acetone (the concentration of the methanesulfonic acid in acetone was 25 mg/mL) was slowly added dropsie, white precipitates were produced, the bottle cap was covered tightly at room temperature, the system was stirred for 1 day, the suspension was centrifuged, and the collected solid was dried under vacuum at 40° C. overnight to obtain a compound of formula I mesylate solid. Upon testing, the solid was crystal form G of a mesylate of a compound of formula I. See FIGS. 20, 21 and 22 for the XRPD pattern, the DSC thermogram and the DVS isotherm plot.

Preparation of Crystal Form H of a Hydrobromide of a Compound of Formula I

Example 45

Figure 23:
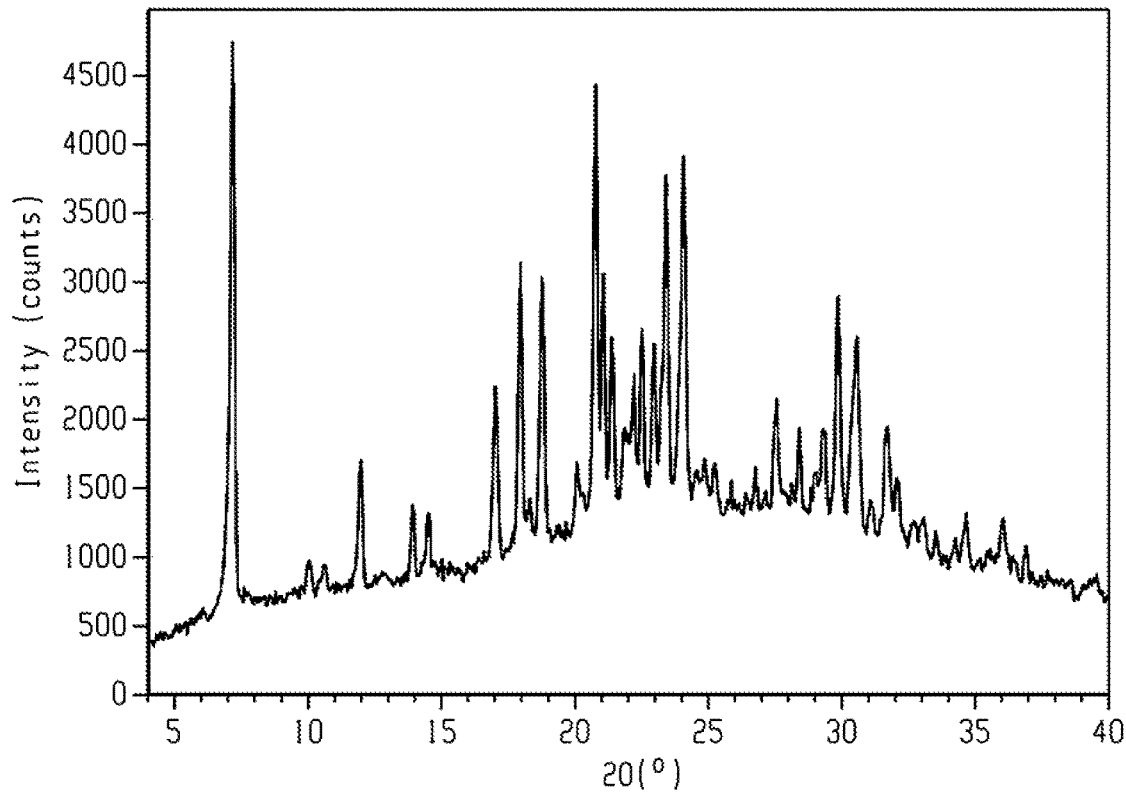
FIG. 23 is the XRPD pattern of crystal form H of a hydrobromide of a compound of formula I of the invention.
Figure 24:
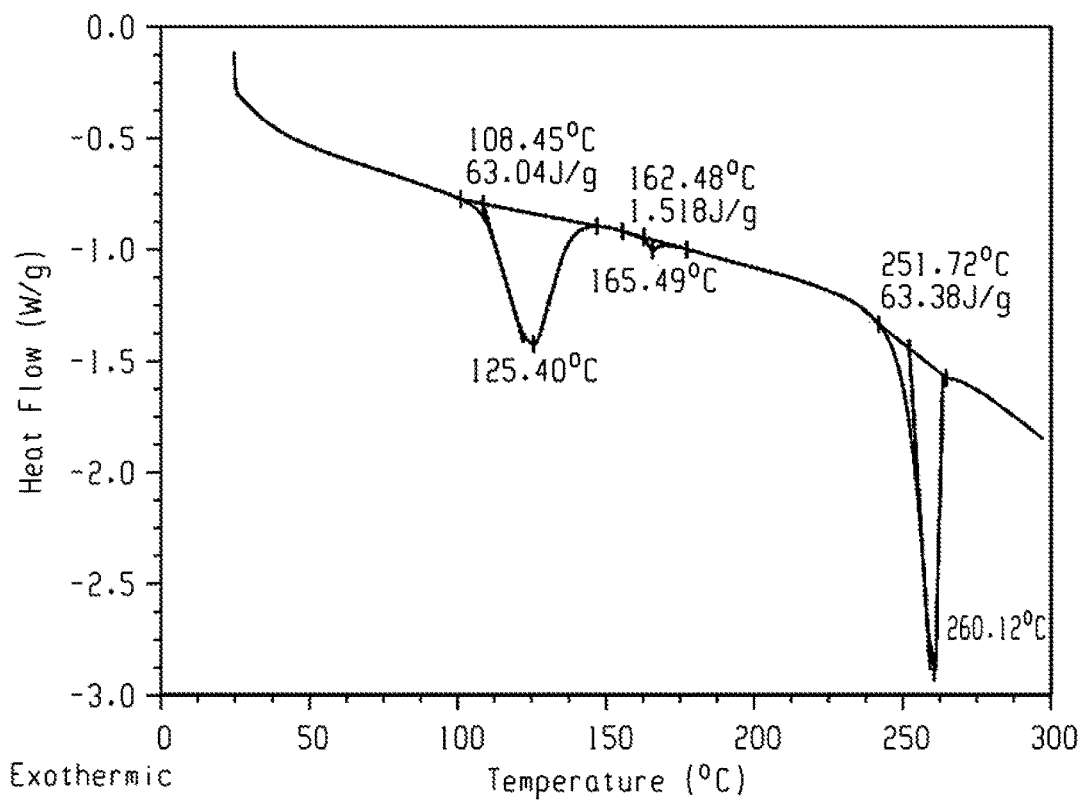
FIG. 24 is the DSC thermogram of crystal form H of a hydrobromide of a compound of formula I of the invention.

About 50 mg of a compound of formula I was weighed and placed into a small bottle, 2.5 mL of acetone was added, the system was subjected to ultrasonication and heating until the compound was completely dissolved, to prepare 20 mg/mL a compound of formula I in acetone. The sample bottle was placed on a magnetic stirring plate, magnetic stirring was conducted and 1.32 mL of hydrobromic acid in acetone (the concentration of the hydrobromic acid in acetone was 25 mg/mL) was slowly added dropwise, white precipitates were produced, the bottle cap was covered tightly at room temperature, the system was stirred for 1 day, the suspension was centrifuged, and the collected solid was dried under vacuum at 40° C. overnight to obtain a compound of formula I hydrobromide solid. Upon testing, the solid was crystal form H of a hydrobromide of a compound of formula I. See FIGS. 23 and 24 for the XRPD pattern and the DSC isotherm plot.

Example 46

5 mg of crystal form H of a hydrobromide of a compound of formula I prepared in example 46 was weighed and placed into a small bottle, a suitable amount of acetonitrile was added, magnetic stirring of the sample suspension was conducted at room temperature overnight, the system was centrifuged and the solid and liquid were separated, the solid was collected, and dried under vacuum overnight at 40° C. to obtain a compound of formula I hydrobromide solid. Upon testing, the solid was still crystal form H of a hydrobromide of a compound of formula I. Its XRPD pattern is consistent with FIG. 23.

Example 47

The method that was the same as that in example 46 was adopted. The solvent was changed to methyl ethyl ketone to prepare crystal form H of a hydrobromide of a compound of formula I. Upon testing, the XRPD pattern of the solid compound prepared in example 47 is consistent with FIG. 23.

Preparation of Crystal Form J of a Hydrobromide of a Compound of Formula I

Example 48

Figure 25:
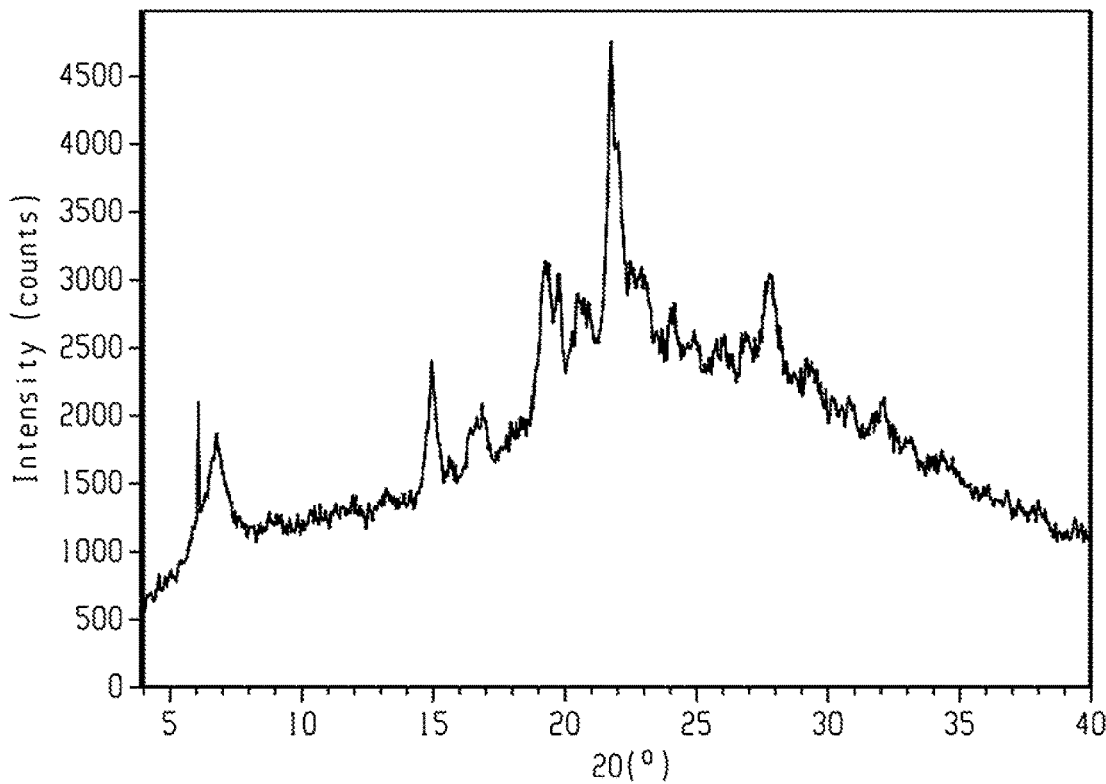
FIG. 25 is the XRPD pattern of crystal form J of a hydrobromide of a compound of formula I of the invention.
Figure 26:
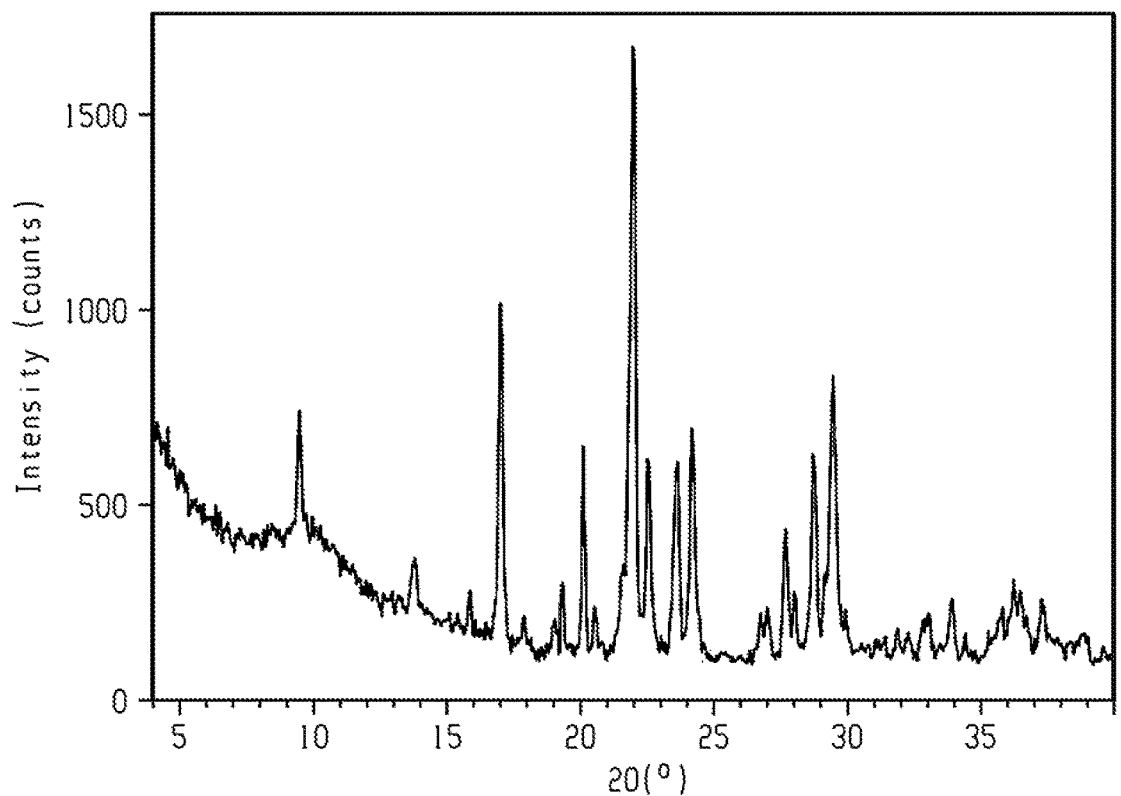
FIG. 26 is the XRPD pattern of crystal form K of a hydrobromide of a compound of formula I of the invention.
Figure 27:
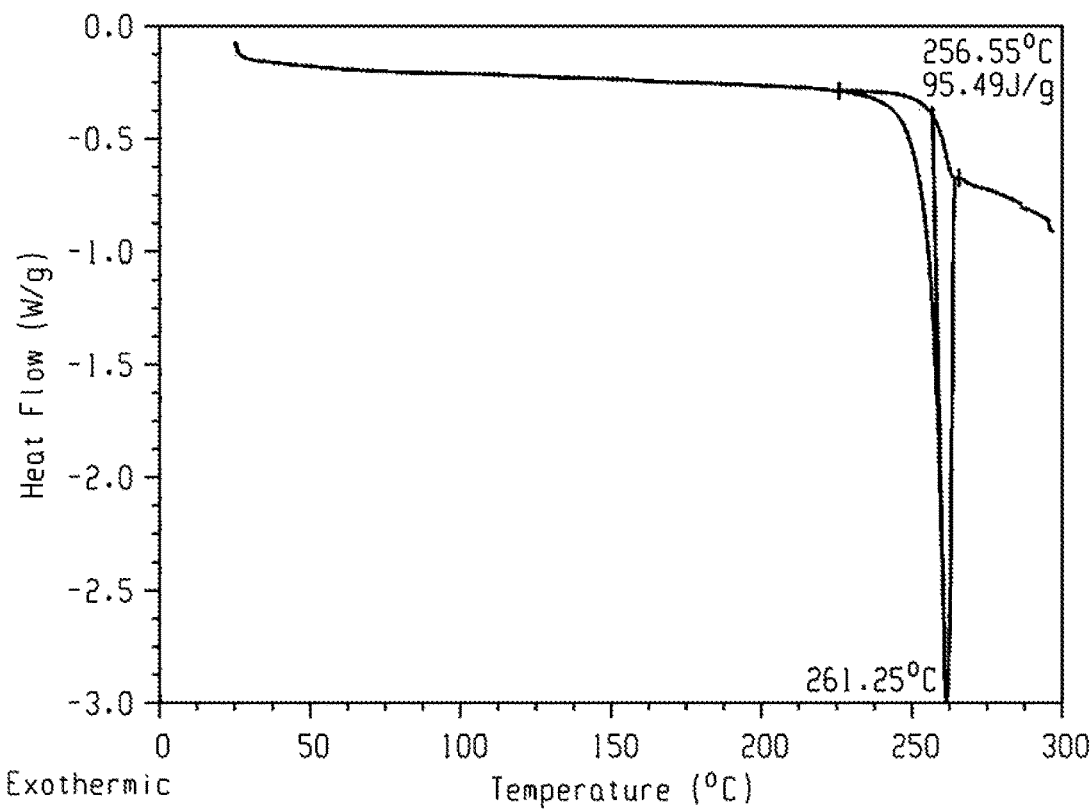
FIG. 27 is the DSC thermogram of crystal form K of a hydrobromide of a compound of formula I of the invention.
Figure 28:
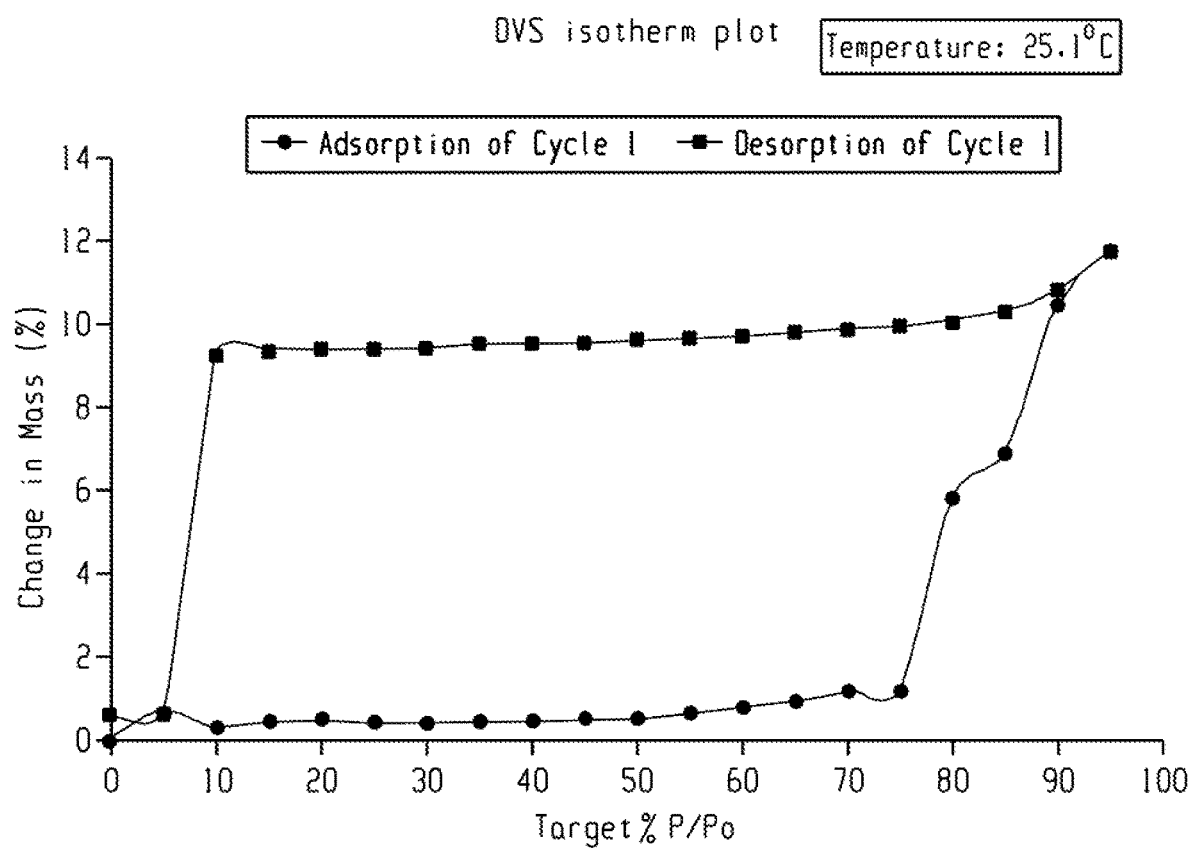
FIG. 28 is the DVS isotherm plot of crystal form K of a hydrobromide of a compound of formula I of the invention.
Figure 29:
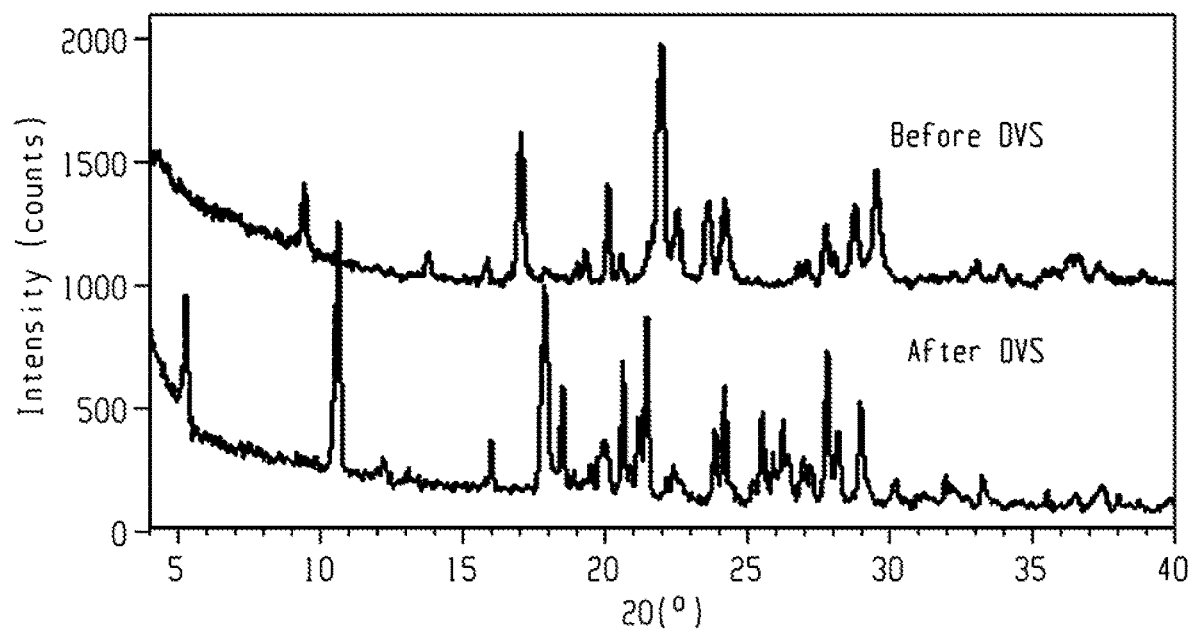
FIG. 29 is the XRPD overlay pattern of crystal form K of a hydrobromide of a compound of formula I of the invention before and after the DVS test.

About 50 mg of a compound of formula I was weighed and placed into a small bottle, 2.5 mL of ethyl acetate was added, the system was subjected to ultrasonication and heating until the compound was completely dissolved, to prepare 20 mg/mL a compound of formula I in ethyl acetate. The sample bottle was placed on a magnetic stirring plate, magnetic stirring was conducted and 1.32 mL of hydrobromic acid in ethyl acetate (the concentration of the hydrobromic acid in ethyl acetate was 25 mg/mL) was slowly added dropwise, white precipitates were produced, the bottle cap was covered tightly at room temperature, the system was stirred for 1 day, the suspension was centrifuged, and the collected solid was dried under vacuum at 40° C. overnight to obtain a compound of formula I hydrobromide solid. Upon testing, the solid was crystal form J of a hydrobromide of a compound of formula I. See FIG. 25 for the XRPD pattern.

Preparation of Crystal Form K of a Hydrobromide of a Compound of Formula I

Example 49

5 mg of crystal form H of a hydrobromide of a compound of formula I prepared in example 46 was weighed and placed into a small bottle, a suitable amount of n-heptane was added, magnetic stirring of the sample suspension was conducted at room temperature overnight, the system was centrifuged and the solid and liquid were separated, the solid was collected, and dried overnight under vacuum at 40° C. to obtain a compound of formula I hydrobromide solid. Upon testing, the solid was crystal form K of a hydrobromide of a compound of formula I. See FIGS. 26-29 for the XRPD pattern, the DSC thermogram, and the DVS isotherm plot and the XRPD pattern after the DVS test.

Preparation of Crystal Form L of a Fumarate of a Compound of Formula I

Example 50

Figure 30:
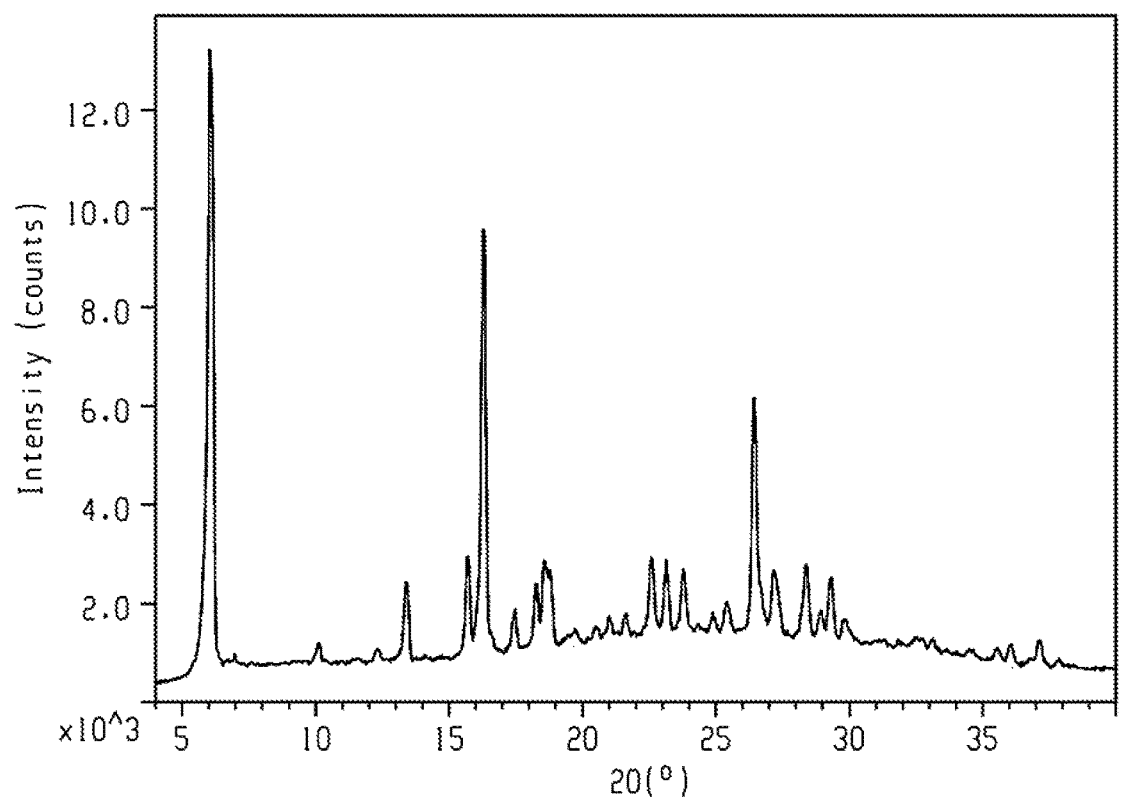
FIG. 30 is the XRPD pattern of crystal form L of a fumarate of a compound of formula I of the invention.
Figure 31:
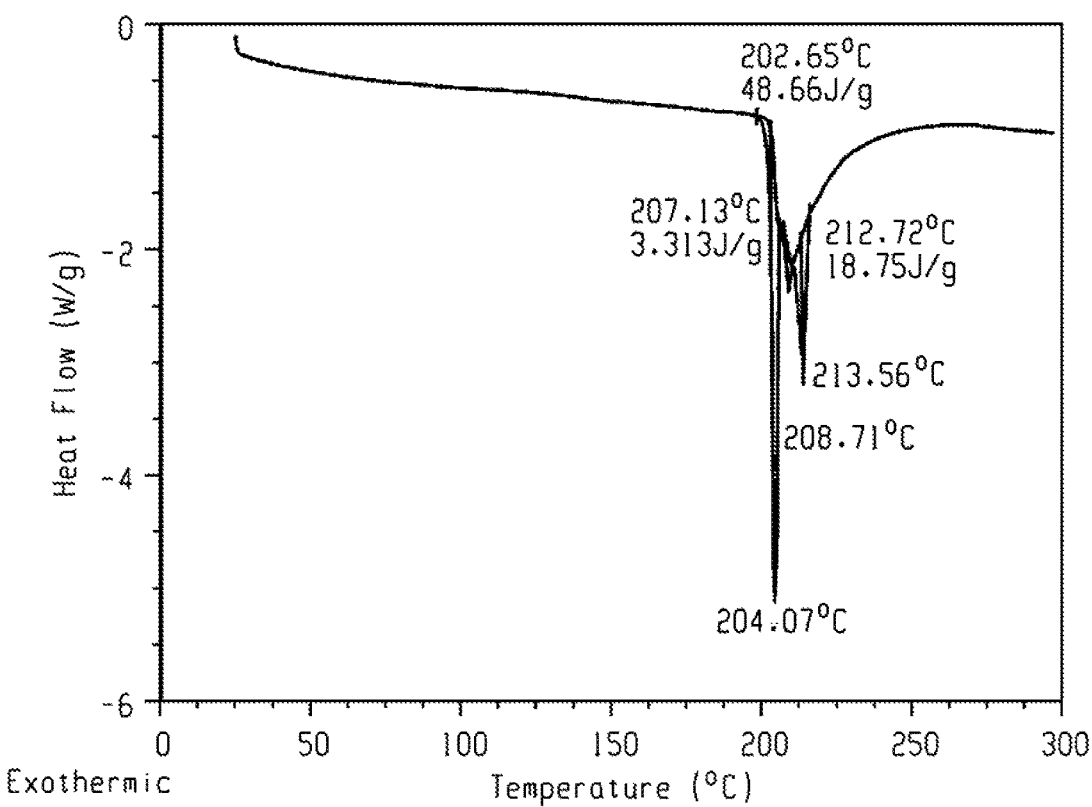
FIG. 31 is the DSC thermogram of crystal form L of a fumarate of a compound of formula I of the invention.
Figure 32:
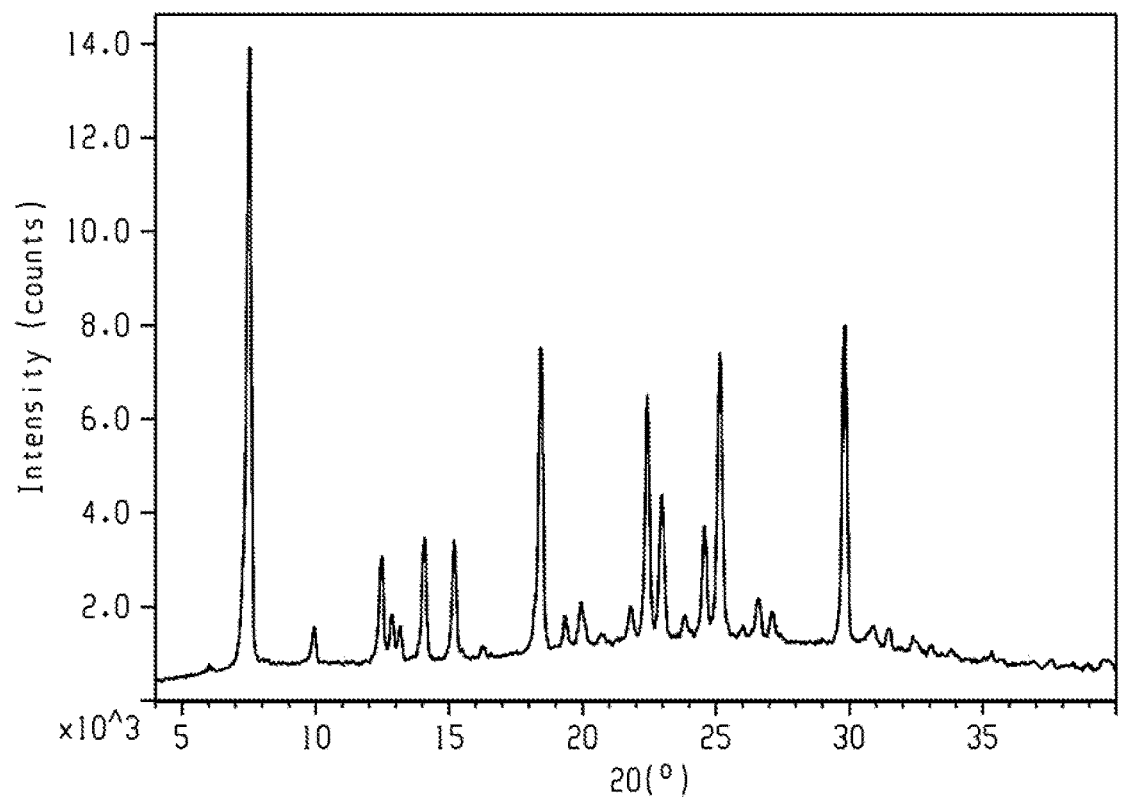
FIG. 32 is the XRPD pattern of crystal form M of a benzene sulfonate of a compound of formula I of the invention.
Figure 33:
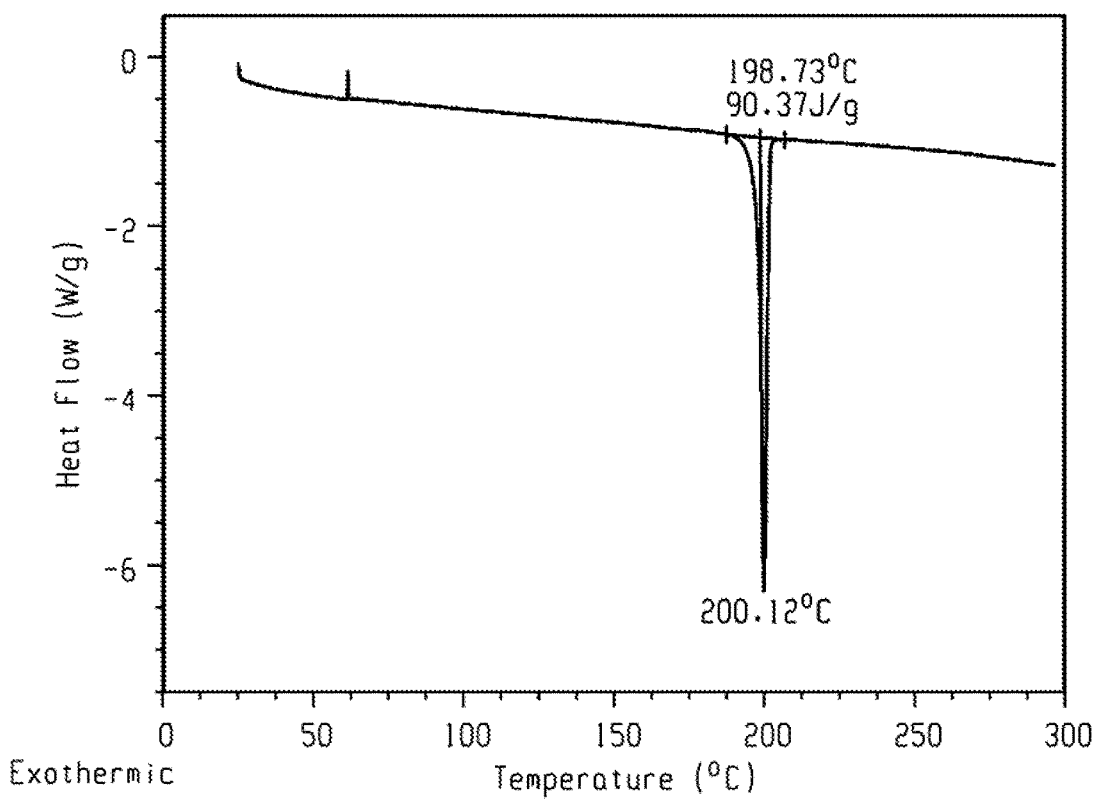
FIG. 33 is the DSC thermogram of crystal form M of a benzene sulfonate of a compound of formula I of the invention.
Figure 34:
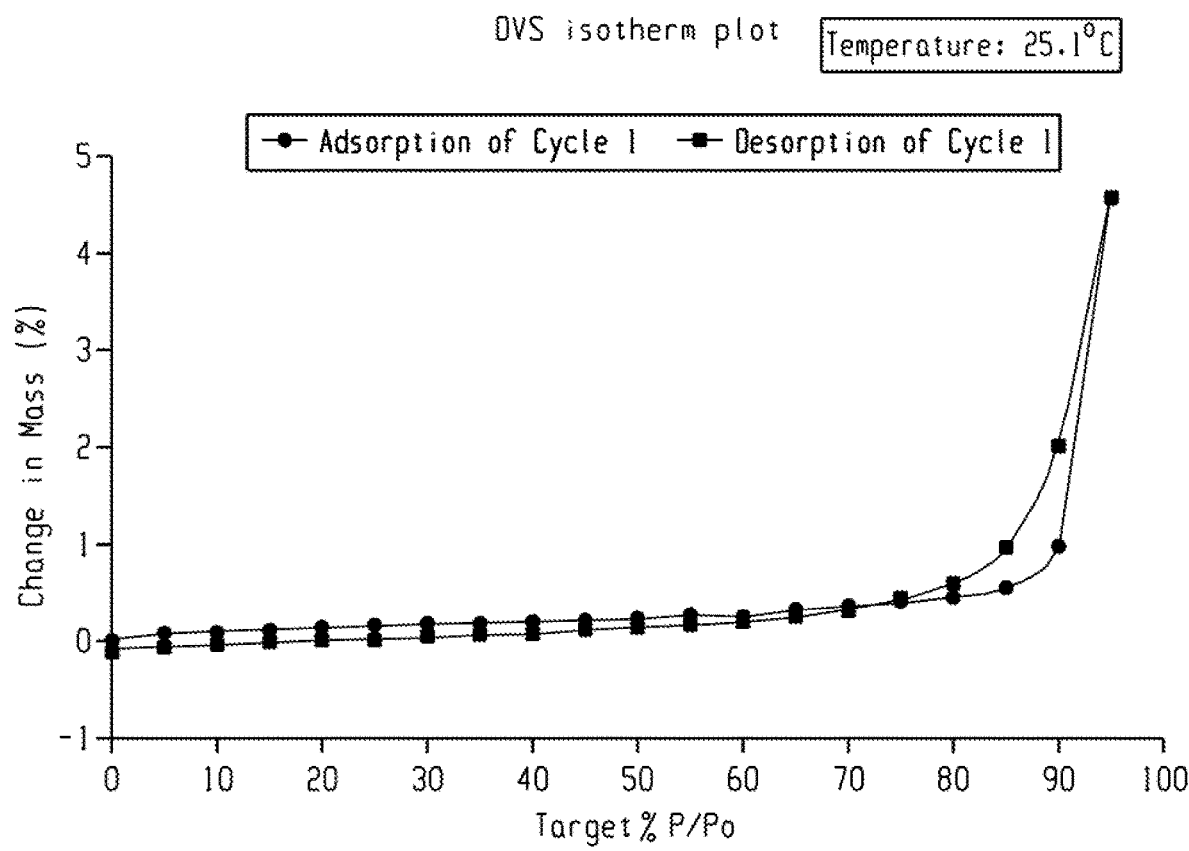
FIG. 34 is the DVS isotherm plot of crystal form M of a benzene sulfonate of a compound of formula I of the invention.
Figure 35:
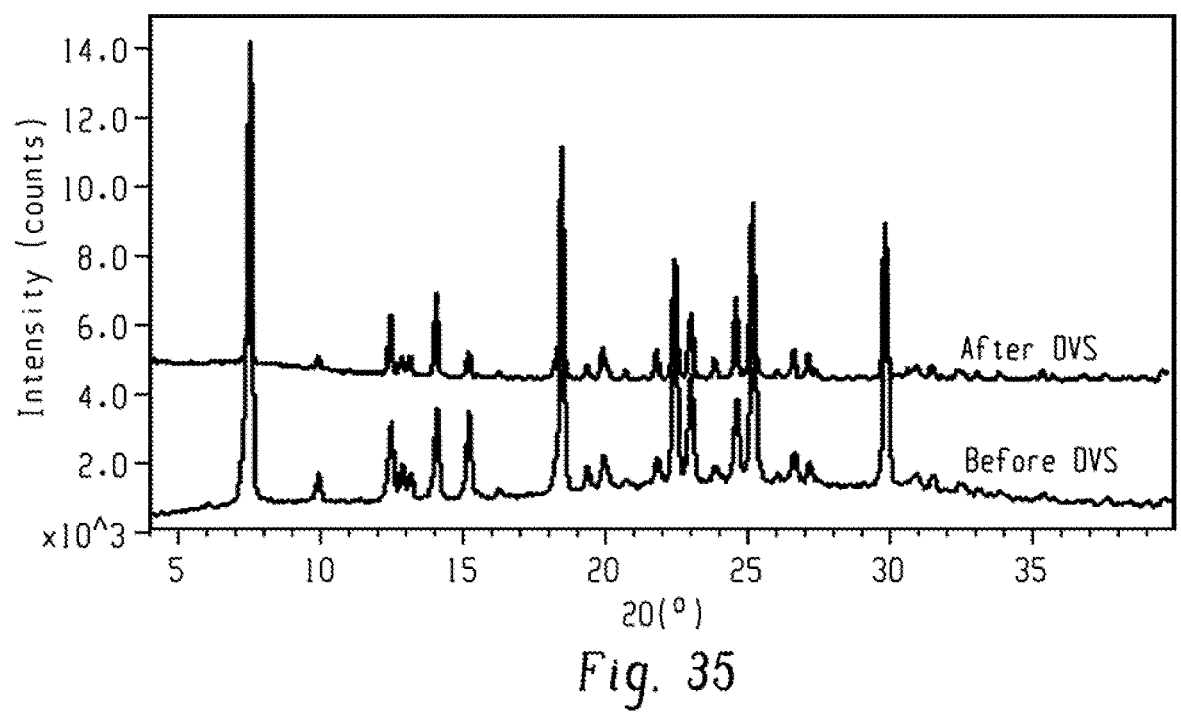
FIG. 35 is the XRPD overlay pattern of crystal form M of a benzene sulfonate of a compound of formula I of the invention before and after the DVS test.

About 50 mg of a compound of formula I was weight and placed into a small bottle, 2.5 mL of ethyl acetate was added, the system was subjected to ultrasonicatiomg and heating until the compound was completely dissolved, to prepare 20 mg/mL a compound of formula I in ethyl acetate. The sample bottle was placed on a magnetic stirring plate, magnetic stirring was conducted and 0.87 mL of fumaric acid in ethanol (the concentration of the fumaric acid in ethanol was 25 mg/mL) was slowly added dropwise, white precipitates were produced, the bottle cap was covered tightly at room temperature, the system was stirred for 1 day, the suspension was centrifuged, and the collected solid was dried under vacuum at 40° C. overnight to obtain a compound of formula I fumarate solid. Upon testing, the solid was crystal form L of a fumarate of a compound of formula I. See FIGS. 30 and 31 for the XRPD pattern and the DSC thermogram.

Example 51

The crystallization method that was the same as that in example 50 was adopted. Ethyl acetate was changed to acetone to prepare crystal form L of a fumarate of a compound of formula I. Upon testing, the XRPD pattern of the solid compound prepared in example 51 is consistent with FIG. 30.

Preparation of Crystal Form M of a Benzene Sulfonate of a Compound of Formula I

Example 52

About 50 mg of a compound of formula I wa weighed and placed into a small bottle, 2.5 mL of acetone was added, the system was subjected to ultrasonication and heating until the compound was completely dissolved, to prepare 20 mg/mL a compound of formula I in acetone. The sample bottle was placed on a magnetic stirring plate, magnetic stirring was conducted and 1.34 mL of benzenesulfonic acid in acetone (the concentration of the benzenesulfonic acid in acetone was 25 mg/mL) was slowly added dropwise, white precipitates were produced, the bottle cap was covered tightly at room temperature, the system was stirred for 1 day, the suspension was centrifuged, and the collected solid was dried under vacuum at 40° C. overnight to obtain a compound of formula I benzene sulfonate solid. Upon testing, the solid was crystal form M of a benzene sulfonate of a compound of formula I. See FIGS. 32-35 for the XRPD pattern, the DSC thermogram, and the DVS isotherm plot and the XRPD pattern after the DVS test.

Preparation of Crystal Form N of a Citrate of a Compound of Formula I

Example 53

Figure 36:
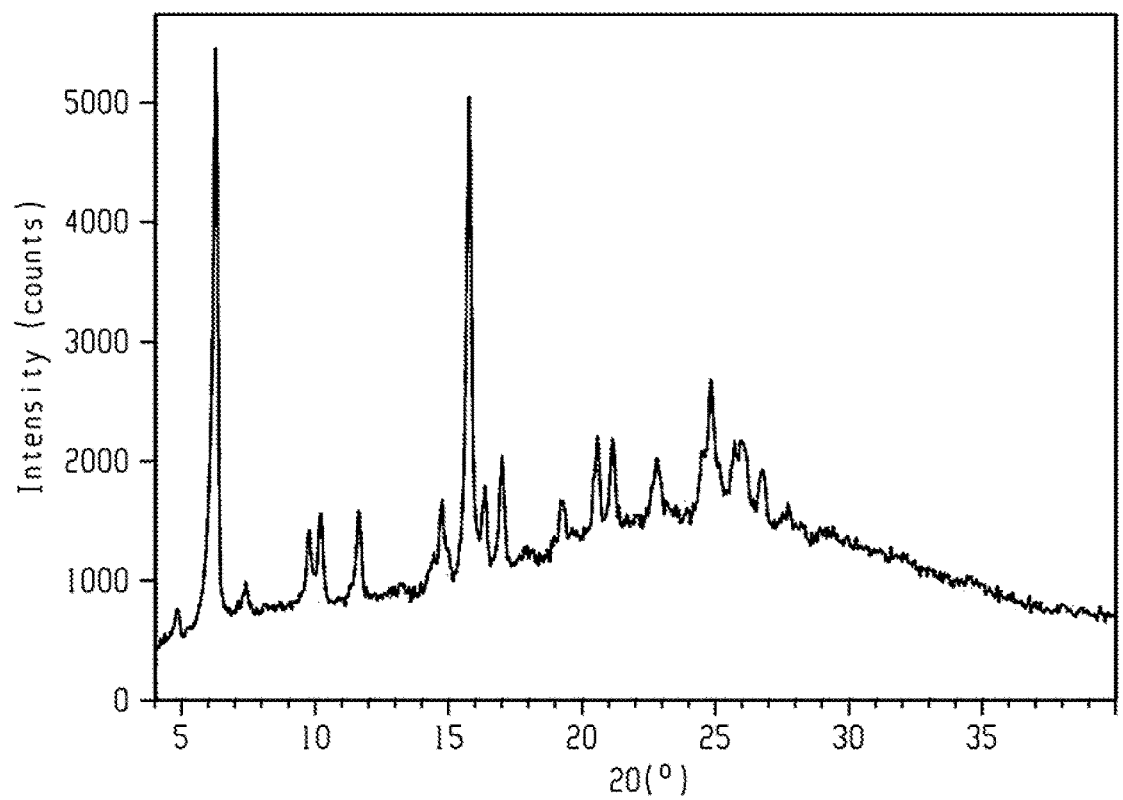
FIG. 36 is the XRPD pattern of crystal form N of a citrate of a compound of formula I of the invention.
Figure 37:
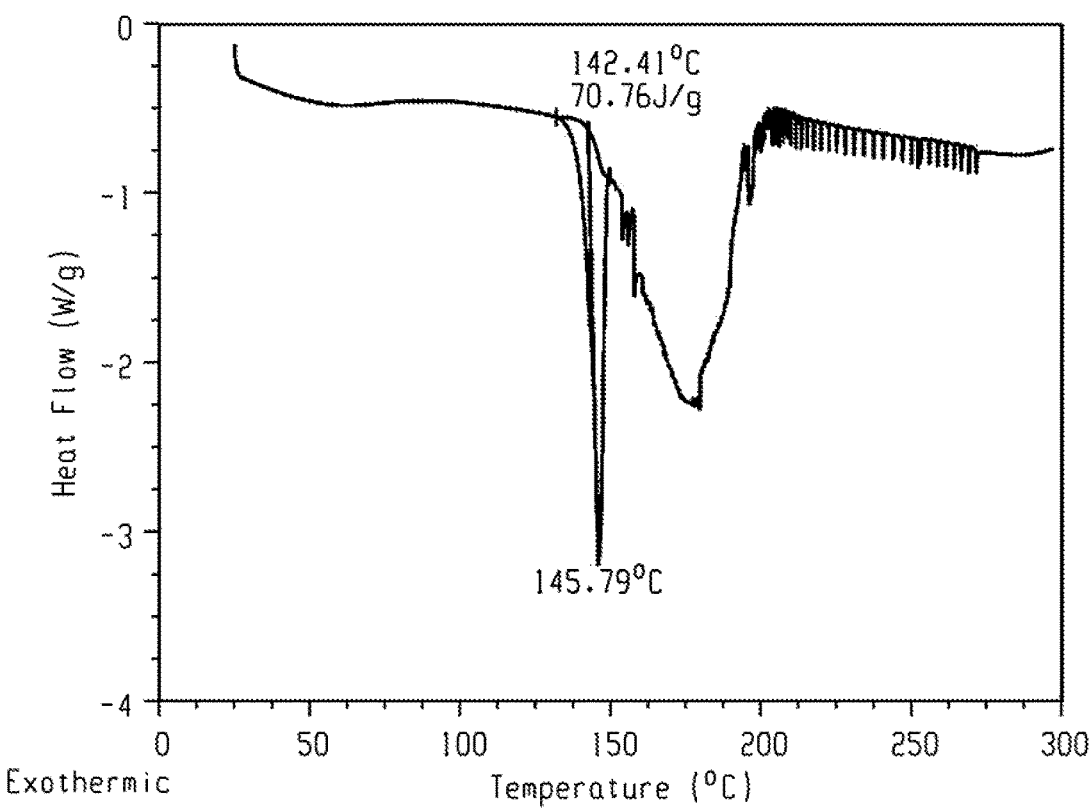
FIG. 37 is the DSC thermogram of crystal form N of a citrate of a compound of formula I of the invention.
Figure 38:
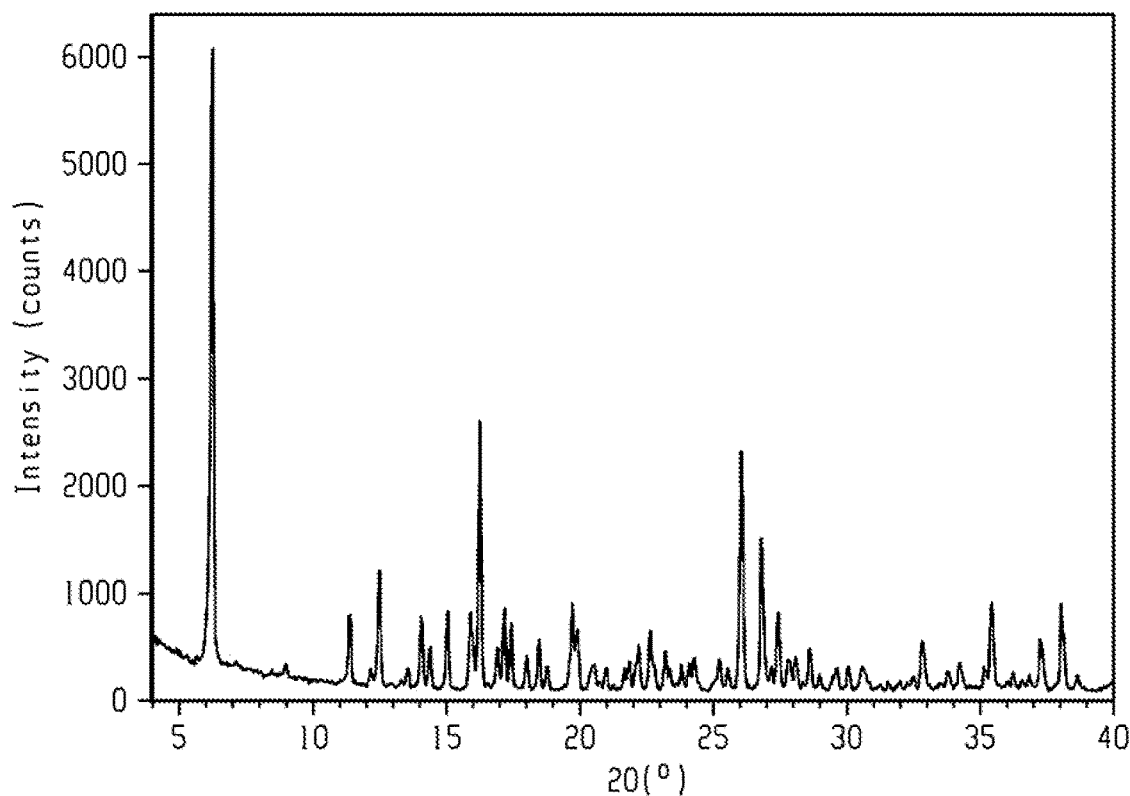
FIG. 38 is the XRPD pattern of crystal form O of a tartrate of a compound of formula I of the invention.
Figure 39:
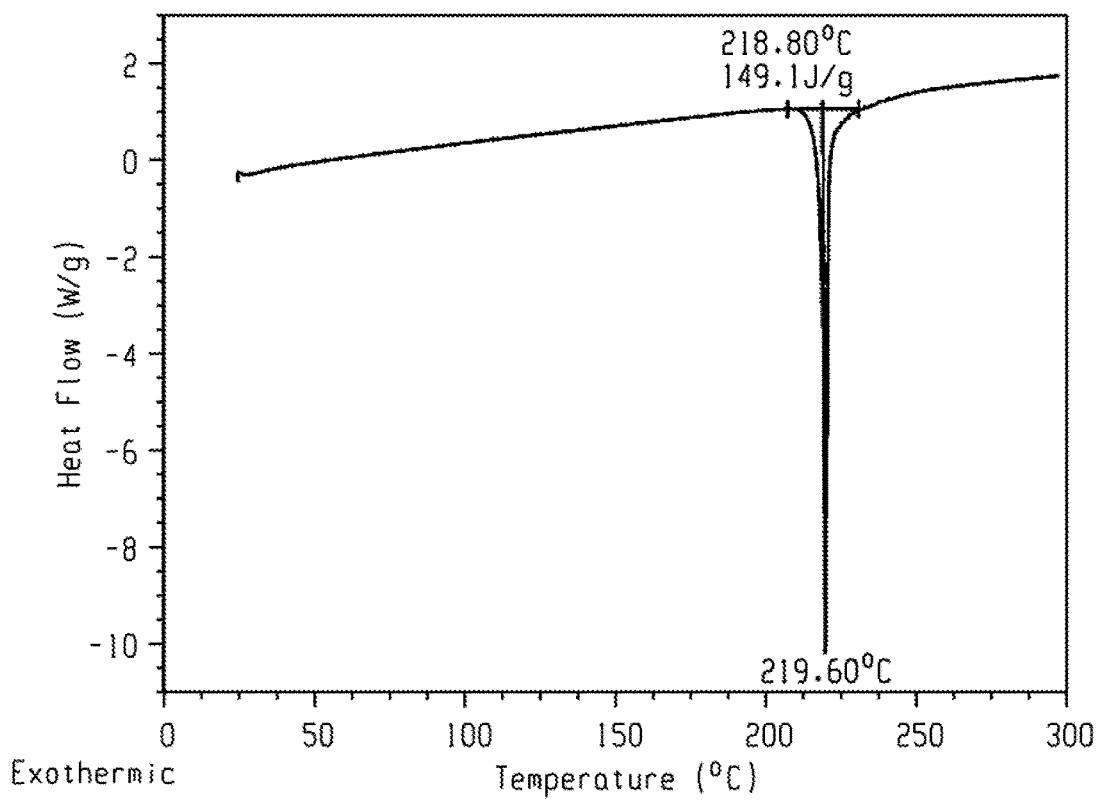
FIG. 39 is the DSC thermogram of crystal form O of a tartrate of a compound of formula I of the invention.
Figure 40:
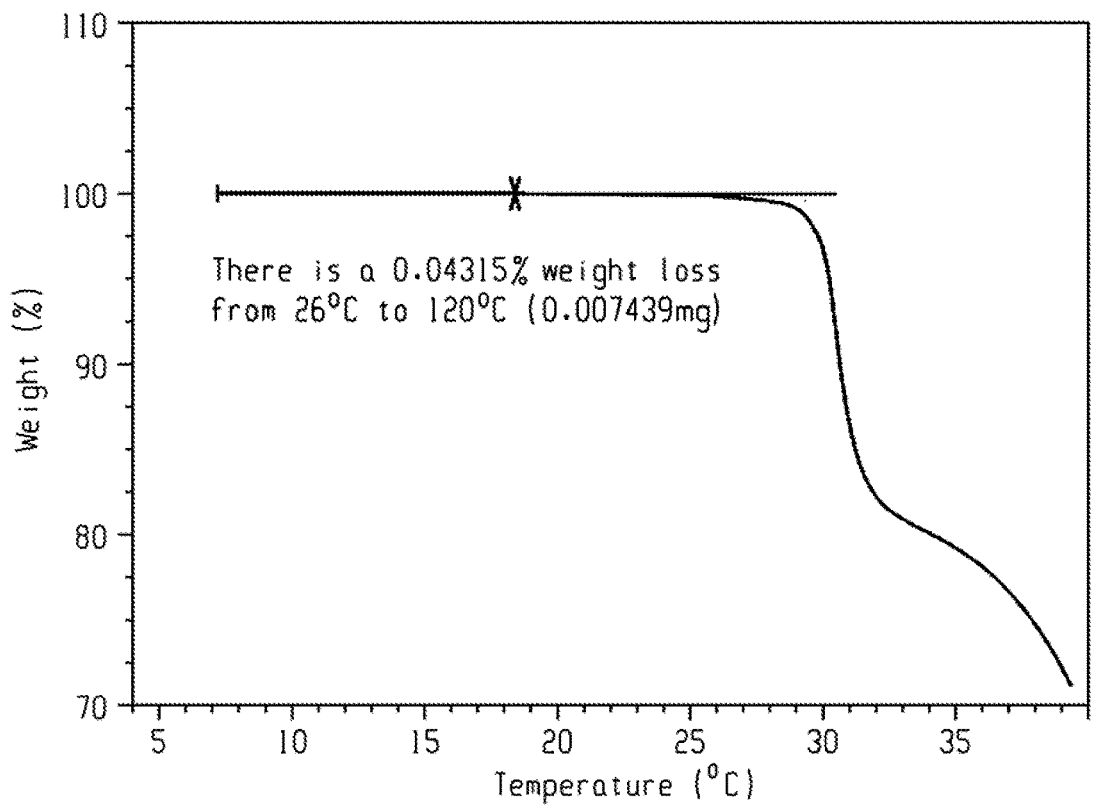
FIG. 40 is the TGA thermogram of crystal form O of a tartrate of a compound of formula I of the invention.
Figure 41:
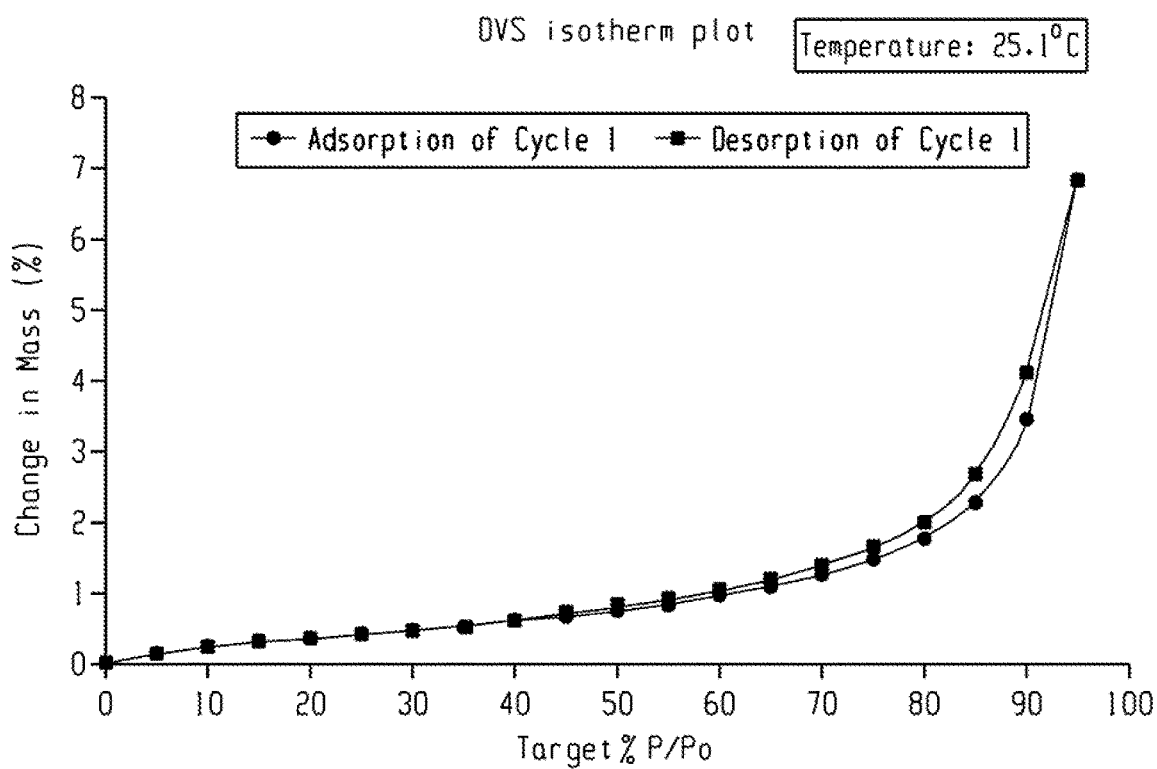
FIG. 41 is the DVS isotherm plot of crystal form O of a tartrate of a compound of formula I of the invention.
Figure 42:
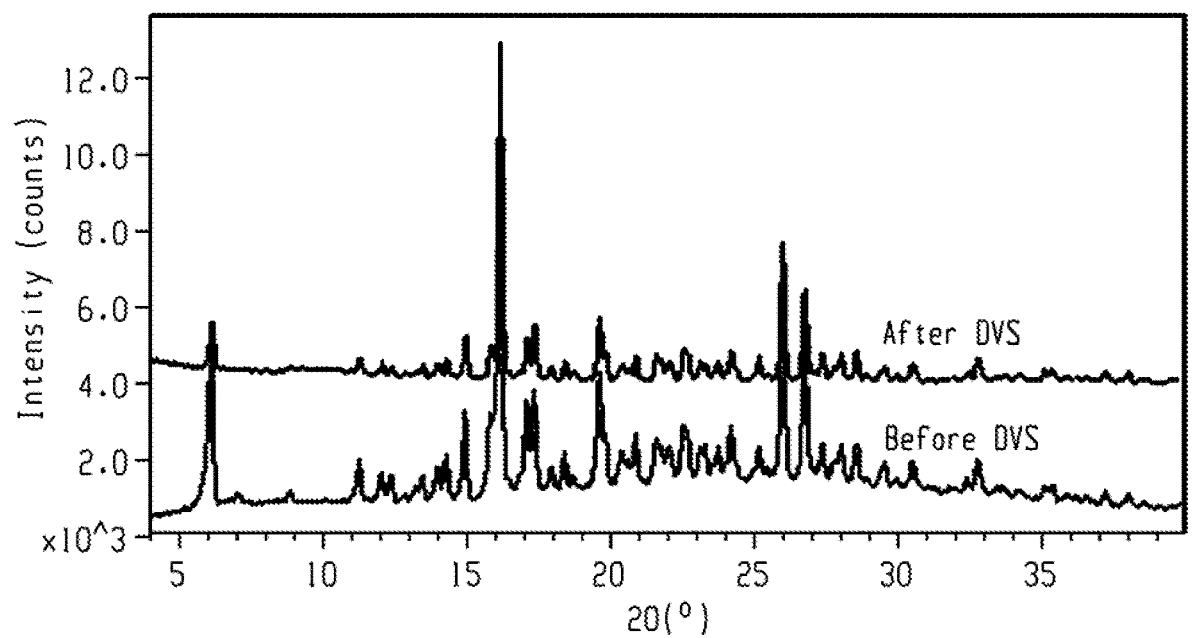
FIG. 42 is the XRPD overlay pattern of crystal form O of a tartrate of a compound of formula I of the invention before and after the DVS test.

About 50 mg of a compound of formula I was weighed and placed into a small bottle, 2.5 mL of ethyl acetate was added, the system was subjected to ultrasonicatiomg and heating until the compound was completely dissolved, to prepare 20 mg/mL a compound of formula I in ethyl acetate. The sample bottle was placed on a magnetic stirring plate, magnetic stirring was conducted and 1.58 mL of citric acid in ethyl acetate (the concentration of the citric acid in ethyl acetate was 25 mg/mL) was slowly added dropwise, white precipitates were produced, the bottle cap was covered tightly at room temperature, the system was stirred for 1 day, the suspension was centrifuged, and the collected solid was dried unhder vacuum at 40° C. overnight to obtain a compound of formula I citrate solid. Upon testing, the solid was crystal form N of a citrate of a compound of formula I. See FIGS. 36 and 37 for the XRPD pattern and the DSC thermogram.

Preparation of Crystal Form O of a Tartrate of a Compound of Formula I

Example 54

About 50 mg of a compound of formula I was weighed and placed into a small bottle, 2.5 mL of ethyl acetate was added, the system was subjected to ultrasonication and heating until the compound was completely dissolved, to prepare 20 mg/mL a compound of formula I in ethyl acetate. The sample bottle was placed on a magnetic stirring plate, magnetic stirring was conducted and 1.12 mL of L-(+)-tartaric acid in ethyl acetate (the concentration of the L-(+)-tartaric acid in ethyl acetate was 25 mg/mL) was slowly added dropwise, white precipitates were produced, the bottle cap was covered tightly at room temperature, the system was stirred for 1 day, the suspension was centrifuge, and the collected solid was dried under vacuum at 40° C. overnight to obtain a compound of formula I L-(+)-tartrate solid. Upon testing, the solid was crystal form O of a tartrate of a compound of formula I. See FIGS. 38-42 for the XRPD pattern, the DSC thermogram, the TGA thermogram and the DVS isotherm plot and the XRPD pattern after the DVS test.

The salt-forming percentage test of crystal form O of a tartrate of a compound of formula I was conducted with a $^1$H NMR method:

About 5 mg of a compound of formula I and crystal form O of a tartrate of a compound of formula I were weighed and placed into a magnetic tube respectively, the samples were dissolved with 0.6 mL of DMSO d6 until each solution was clear, and each the sample solution was scanned with Bruker AVANCE 400 MHz nuclear magnetic resonance spectrometer using the general method to collect the $^1$H-NMR data of the samples.

Figure 43:
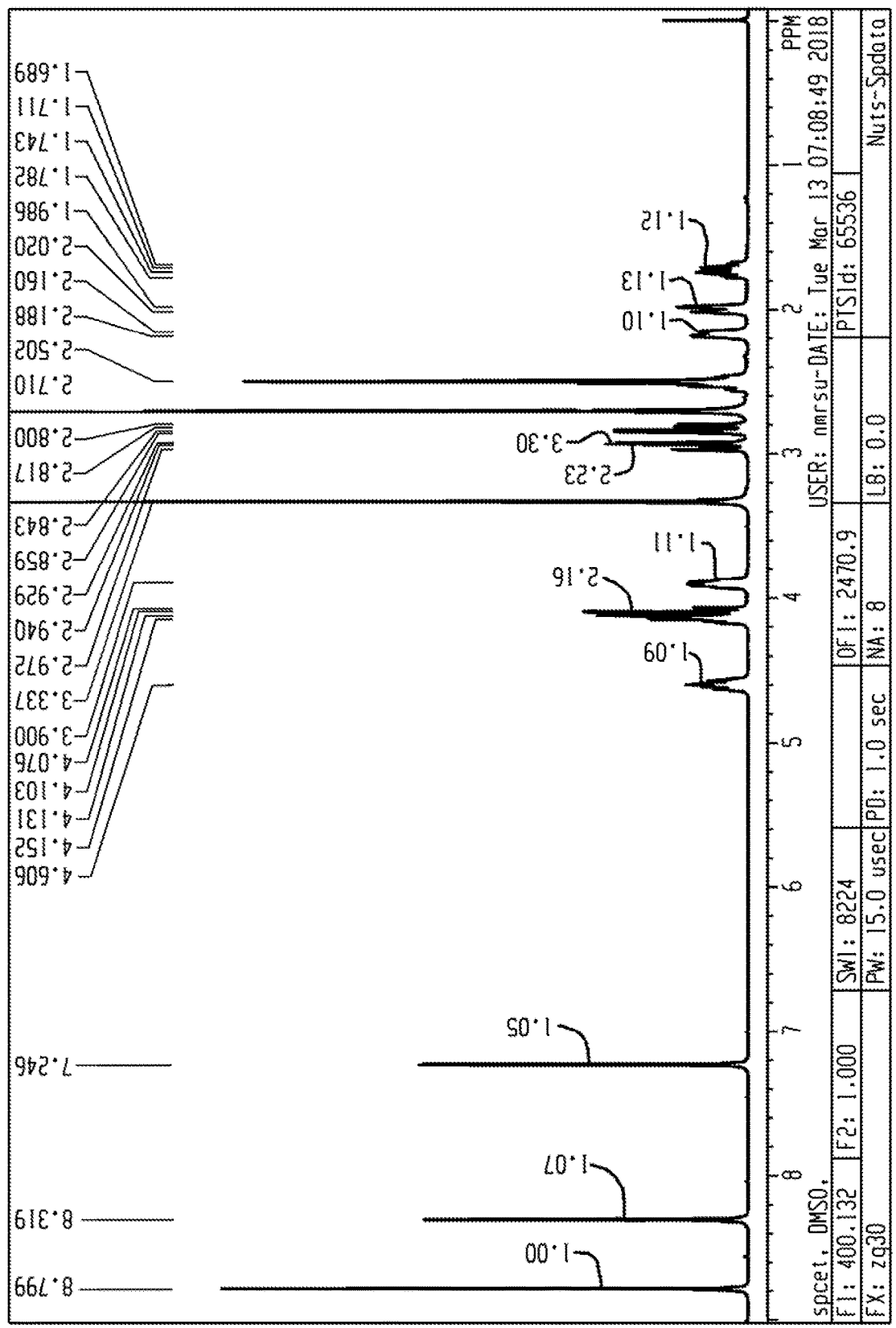
FIG. 43 is the $^1$H NMR spectrum of crystal form 1 of a compound of formula I of the invention.
Figure 44:
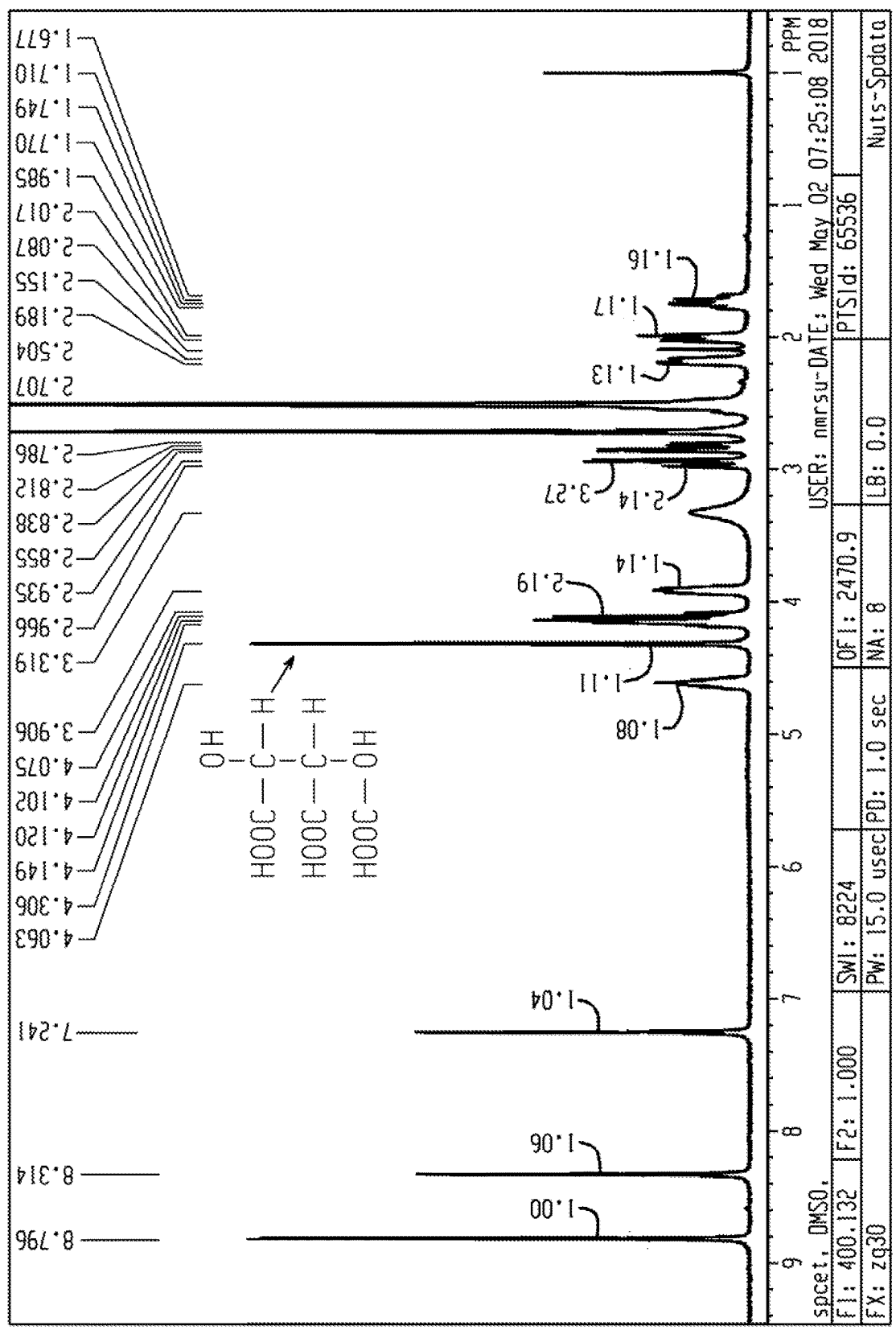
FIG. 44 is the $^1$H NMR spectrum of crystal form O of a tartrate of a compound of formula I of the invention.
Figure 45:
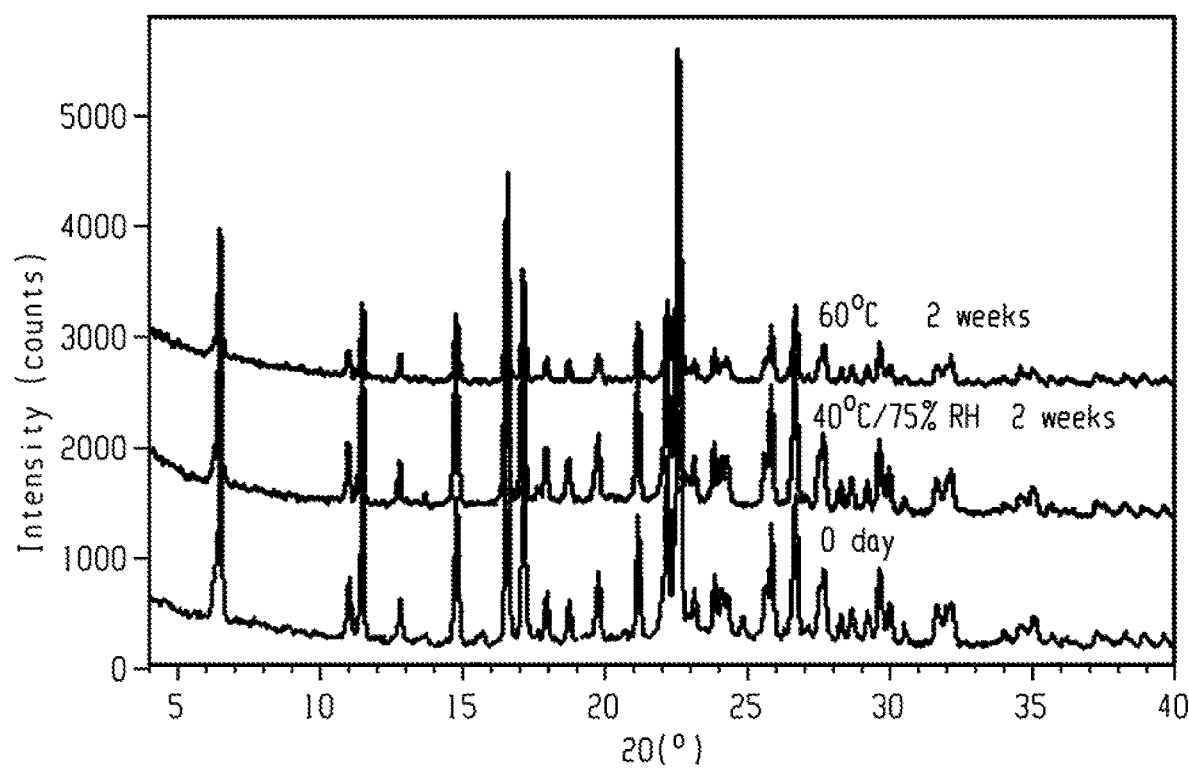
FIG. 45 is the XRPD overlay patttern of crystal form F of a phosphate of a compound of formula I of the invention after being placed at a high temperature and under accelerated conditions for 2 weeks.
Figure 46:
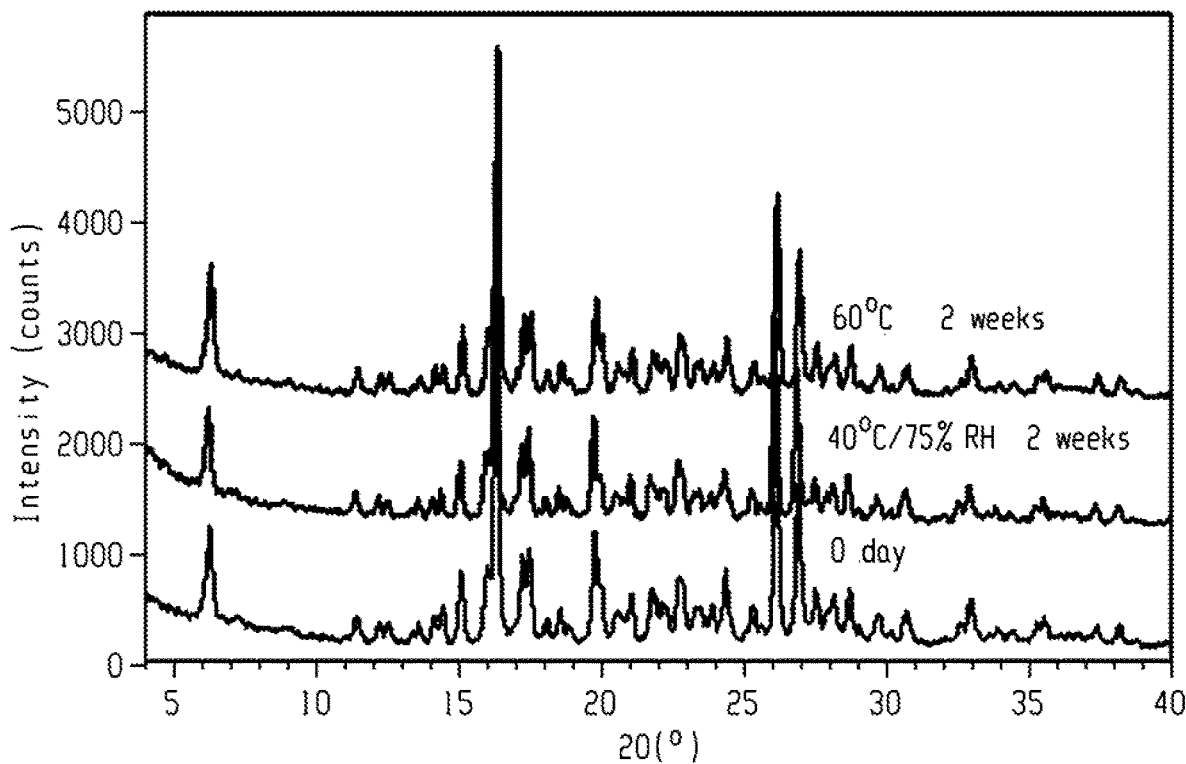
FIG. 46 is the XRPD overlay pattern of crystal form O of a tartrate of a compound of formula I of the invention after being placed at a high temperature and under accelerated conditions for 2 weeks.
Figure 47:
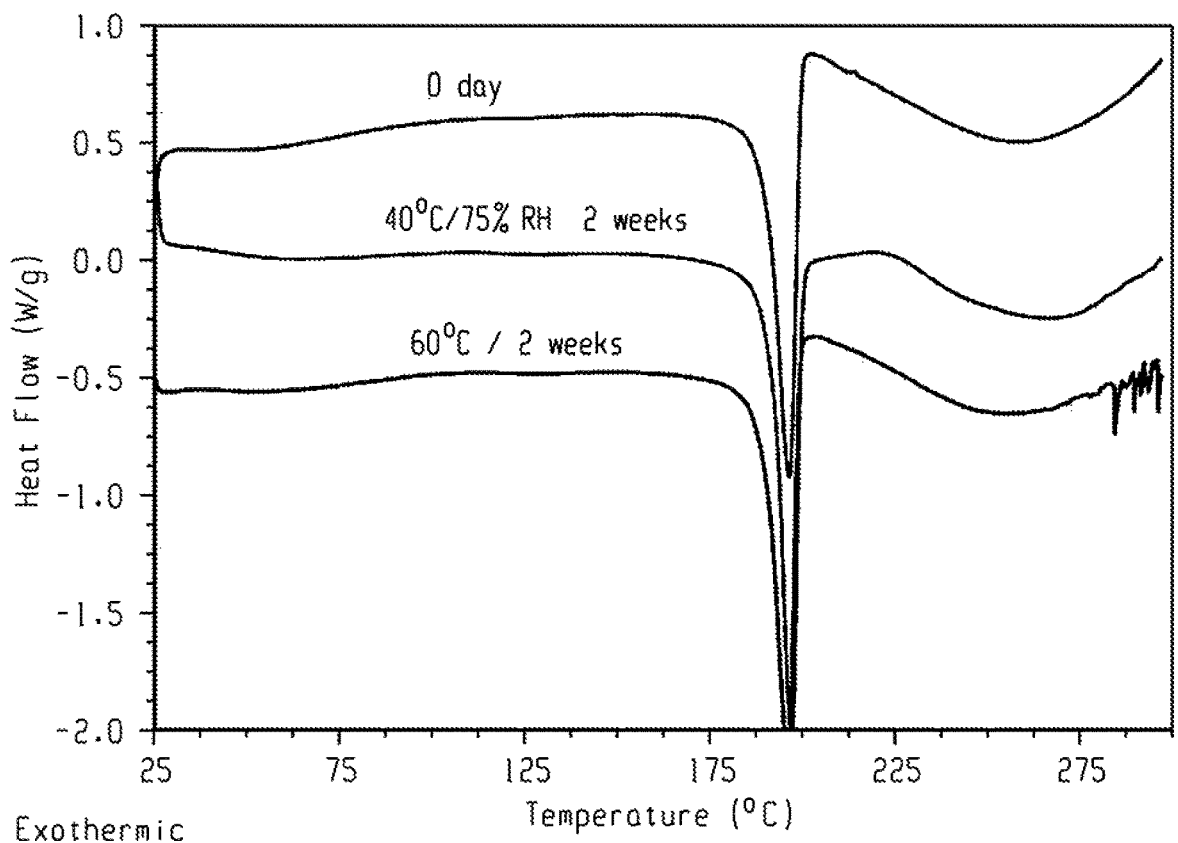
FIG. 47 is the DSC overlay thermogram of crystal form F of a phosphate of a compound of formula I of the invention after being placed at a high temperature and under accelerated conditions for 2 weeks.
Figure 48:
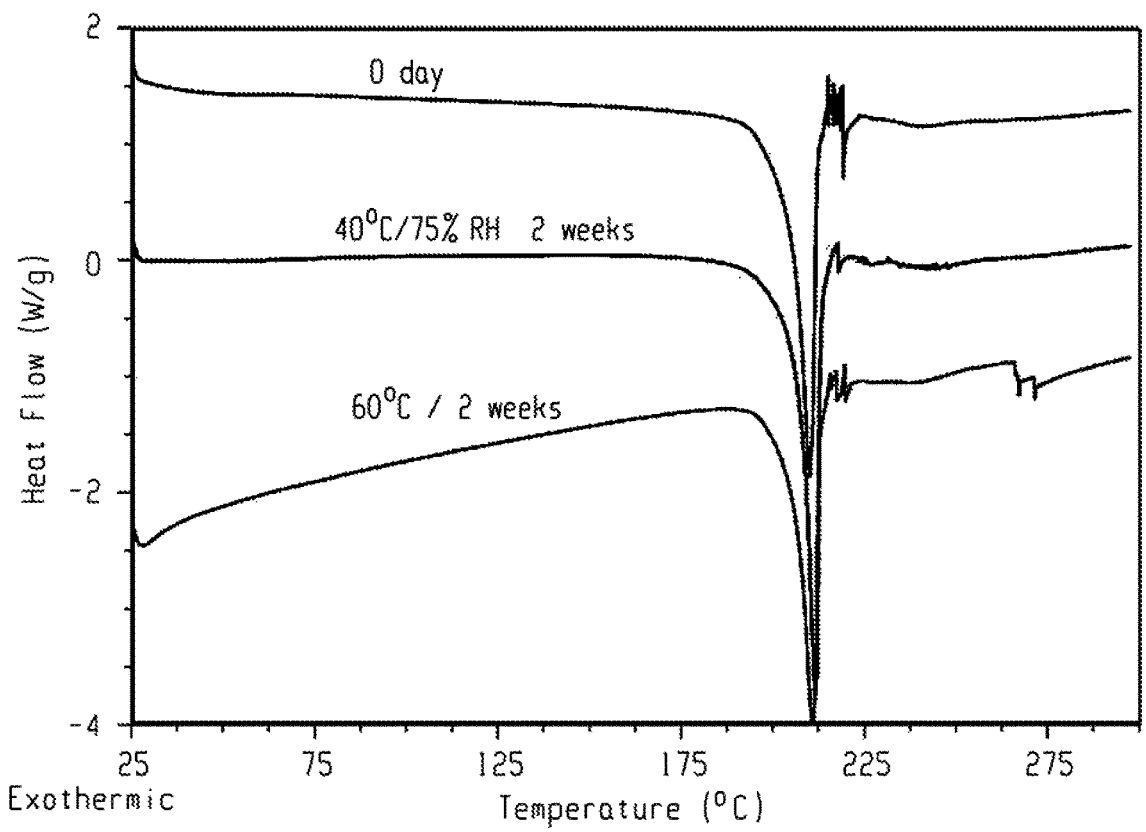
FIG. 48 is the DSC overlay thermogram of crystal form O of a tartrate of a compound of formula I of the invention after being placed at a high temperature and under accelerated conditions for 2 weeks.
Figure 49:
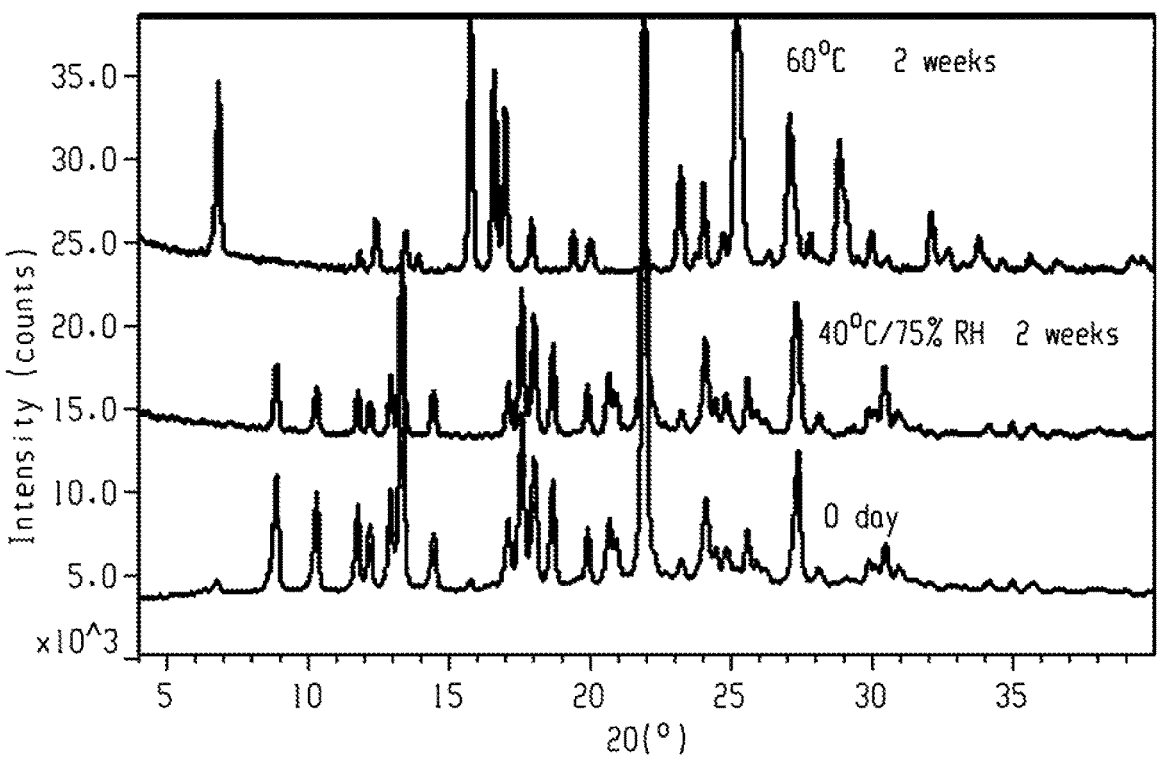
FIG. 49 is the XRPD overlay pattern of crystal form 1 of a compound of formula I of the invention after being placed at a high temperature and under accelerated conditions for 2 weeks.
Figure 50:
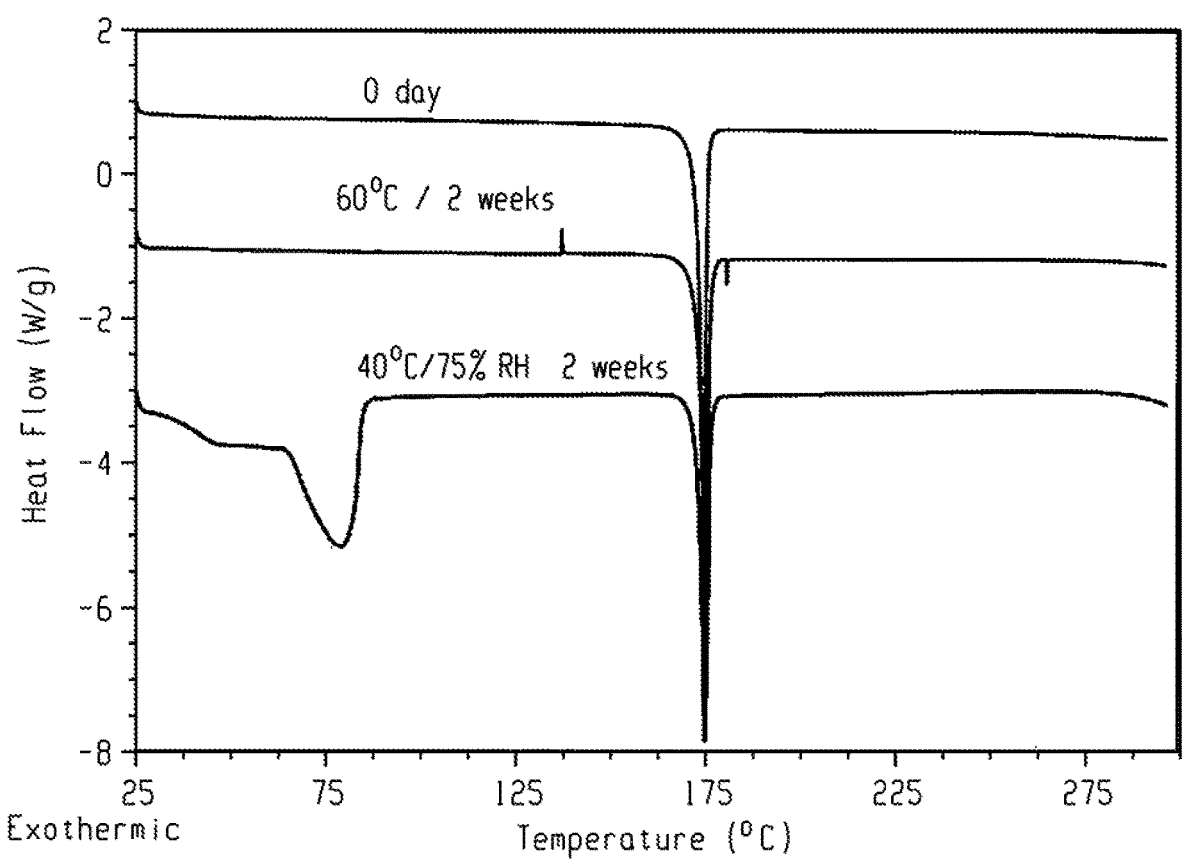
FIG. 50 is the DSC overlay thermogram of crystal form 1 of a compound of formula I of the invention after being placed at a high temperature and under accelerated conditions for 2 weeks.

The NMR spectrums showed that the $^1$H NMR of crystal form O of a tartrate of a compound of formula I contained one more hydrogen than that of the compound of formula I. Because tartaric acid is a diacid. It can be seen that the salt-forming molar ratio of the free base to tartaric acid is 2:1. See FIGS. 43 and 44 for the specific information.

The salt-forming percentage test of crystal form O of a tartrate of a compound of formula I was conducted with a chemical titration:

A nonaqueous titration instrument was adopted, and methanolic potassium hydroxide VS was adopted to titrate the sample. The content of tartaric acid in the sample was calculated with the formula according to the concentration of the titrant and the volume consumed of the titrant.

TABLE 18

Blank titration condition

| | |
|---|---|
| System | Tiamo 2.2 light |
| Electrode | pH-electrode filled with 1M LiCl/EtOH, Metrohm, No. 6.0299.010 |
| Titrator | Metrohm 809 Titrando |
| Titrant | 0.1 mol/ L methanolic potassium hydroxide VS |
| Titration volume | 1 mL |

TABLE 19

Sample titration condition

| | |
|---|---|
| System | Tiamo 2.2 light |
| Electrode | pH-electrode filled with 1M LiCl/EtOH, Metrohm, No. 6.0299.010 |
| Titrator | Metrohm 809 Titrando |
| Titrant | 0.1 mol/ L methanolic potassium hydroxide VS |
| Titration volume | 1 mL |
| Sample concentration | 1.25 mg/mL |

80 mL of methanol solution was taken and placed into a titration cup, titration was conducted according to the blank titration condition in triplicate. 160 mg of standard potassium acid phthalate that has been dried to a constant weight at 105° C. was weighed accurately, 50 ml of methanol solution was added, the system was subjected to ultrasonicationg to dissolve, and was then transferred to the titration cup, and titration was conducted according to the sample titration condition in triplicate. 100 mg of crystal form O of a tartrate of a compound of formula I was weighed accurately, 80 mL of methanol solution was added, the system was subjected to ultrasonicationg to dissolve and was then transferred to the titration cup, and titration was conducted according to the sample titration condition in triplicate.

The titer (T) of the titrant was calculated according to the following formula:

$$T(\text{mol/L}) = \frac{W}{M \times (V - V_0)} \times 1000$$

W: Weighting of standard potassium hydrogen phthalate (g)

V: The volume of methanolic potassium hydroxide VS consumed for titrating standard potassium acid phthalate solution (mL)

$V_0$: The volume of methanolic potassium hydroxide VS consumed for titrating blank solution (mL)

M: The molecular weight of standard potassium hydrogen phthalate

The tartaric acid content in the sample was calculated according to the following formula:

$$\text{Assay }(\%) = \frac{T \times (V - V_0)}{1000 \times W \times 2} \times 100\%$$

T: The titer of a calibrated methanolic potassium hydroxide VS (mol/L)

V: The volume of methanolic potassium hydroxide VS consumed for titrating sample solution (mL)

$V_0$: The volume of methanolic potassium hydroxide VS consumed for titrating blank solution (mL)

M: The molecular weight of tartaric acid

W: Sample weighting (g)

The final titration test results indicated that the content of tartaric acid in crystal form O of a tartrate of a compound of formula I was 19.2 w/w % and 21.1 w/w %, respectively, which was consistent with the theoretical value 20.2 w/w % when the molar ratio of the free base: tartaric acid was 2:1.

Example 55

About 500 mg of a compound of formula I was weighed and placed into a small bottle, 20 mL of acetone was added, the system as subjected to ultrasonication and heating until the compound was completely dissolved, to prepare 25 mg/mL a compound of formula I in acetone. The sample bottle was placed on a magnetic stirring plate, magnetic stirring was conducted and 11.2 mL of L-(+)-tartaric acid in acetone (the concentration of the L-(+)-tartaric acid in acetone was 25 mg/mL) was slowly added dropwise, the system was stirred overnight, filtered, and the solid was dried under vacuum at 50° C. to obtain a compound of formula I L-(+)-tartrate solid. Upon testing, the solid was crystal form O of a tartrate of a compound of formula I. Its XRPD pattern is consistent with FIG. 38.

Example 56

2.0 g of a compound of formula I with an HPLC purity of 99.9% prepared by the purification of component A in example 27 and 40 mL of acetone (20 V) were added to flask 1 #, the system was stirred to dissolve until the solution was clear; 0.61 g of L-(+)-tartaric acid and 40 mL of acetone (20 V) were added to flask 2 #, the system was stirred to dissolve until the solution was clear; the solution in flask 2# was added to flask 1# within 2-3 minutes; the temperature of the system was raised to 50-60° C. and the system was stirred for 2 hours; the system was cooled to room temperature; and was copncetntrated to about 40 mL; the system was stirred at room temperature between 25-30° C. for 1 hour; the system was cooled to 5-10° C., stirred between 5-10° C. for 1 hour; filterred, and the filter cake was dried with an air blower between 50-55° C. for 16 hours to obtain 2.4 g of product, with an HPLC purity of 99.6% and a yield of 95.6%. Upon testing, the solid was crystal form O of a tartrate of a compound of formula I. Its XRPD pattern is consistent with FIG. 38.

Example 57

2.0 g of a compound of formula I with an HPLC purity of 99.9% prepared by the purification of component A in example 27 and 40 mL of acetone (20 V) were added to flask 1 #, the temperature was raised to 50-55° C., the system was stirred to dissolve until the solution was clear; 0.61 g of L-(+)-tartaric acid and 40 mL of acetone (20 V) were added to flask 2 #, the temperature was raised to 50-55° C., the system was stirred until the solution was clear the solution in flask 2# was added to flask 1# within 2-3 minutes; the system was stirred between 45-50° C. for 2 hours; the system was concentrated under vacuum to about 40 mL at 45-50° C.; cooled to 20-25° C., stirred for 1 hour; cooled to 5-10° C., stirred between 5-10° C. for 1 hour; filterred, and the filter cake was dried with an air blower between 50-55° C. for 16 hours to obtain 2.4 g of product, with an HPLC purity of 99.8% and a yield of 95.62%. Upon testing, the solid was crystal form O of a tartrate of a compound of formula I. Its XRPD pattern is consistent with FIG. 38.

Example 58

36.0 g of a compound of formula I with an HPLC purity of 99.85% prepared by the purification of component A in example 26 and 720 mL of acetone (20 V) were aded to flask 1 #, the temperature was raised to 50-55° C., the system was stirred to dissolve until the solution was clear; 11.0 g of L-(+)-tartaric acid and 720 mL of acetone (20 V) were added to flask 2 #, the temperature was raised to 50-55° C., the system was stirred to dissolve until the solution was clear; the solution in flask 2# was added to flask 1# between 45-55° C. within 2-3 minutes; the system was stirred between 45-50° C. for 2 hours; concentrated under vacuum to about 720 mL; cooled to 5-10° C., stirred for 1 hour between 5-10° C.; filterred, and the filter cake was dried with an air blower between 50-55° C. for 16 hours to obtain 43.6 g of product, with an HPLC purity of 99.96% and a yield of 96.6%. Upon testing, the solid was crystal form O of a tartrate of a compound of formula I. Its XRPD pattern is consistent with FIG. 38.

Example 59

189.6 g of a compound of formula I with an HPLC purity of 99.9% prepared by the purification of component A in example 28 and 3792 mL of acetone (20 V) were added to flask 1 #, the temperature was raised to 50-55° C., the system was stirred to dissolve until the solution was clear; 57.6 g of L-(+)-tartaric acid and 3792 mL of acetone (20 V) were added to flask 2 #, the temperature was raised to 50-55° C., the system was stirred to dissolve until the solution was clear ; the solution in flask 2# was added to flask 1# between 45-55° C.; the system was stirred between 45-50° C. for 2 hours; concentrated under vacuum to about 3800 mL (about 20 V); cooled to 17-21° C., stirred for 1 hour; cooled to 5-10° C., stirred between 5-10° C. for 1 hour; filterred, and the filter cake was dried with an air blower between 50-55° C. for 28 hours to obtain 223.2 g of product, with an HPLC purity of 99.98% and a yield of 94.0%. Upon testing, the solid was crystal form O of a tartrate of a compound of formula I. Its XRPD pattern is consistent with FIG. 38.

Example 60

0.65 kg of a compound of formula I with an HPLC purity of 100.0% prepared by the purification of component A in example 30 and 7.7 kg of acetone were added to a rotary flask, the flask was rotated in a 40-50° C. water bath for 1 hour to make the solution clear; tthe clear solution was transferred to PT1 (reactor 1), compressed with nitrogen through a pipeline filter to the reactor in the purification area; 2.6 kg of acetone was added to the rotary flask, the flask was washed and then transferred to PT1, compressed to the reactor through a pipeline filter; the volume of the reaction liquid in the reactor in the purification room was calibrated to 13.0 L; 7.7 kg of acetone and 0.198 kg of L-tartaric acid were aded to the rotary flask, the rotary flask was rotated in a 40-50° C. water bath for 1 hour to make the solution clear; the clear solution was transferred to PT1, compressed with nitrogen through a pipeline filter to PT2 (reactor 2); 2.6 kg of acetone was added to the rotary flask, the flask was wasshed and the system was transferred to PT1, compressed with nitrogen through a pipeline filter to PT2; the temperature of the material liquid in the reactor was heated to 40-50° C., the materials in PT2 was added to the reactor within 1 hour; the temperature of the materials in the reactor was controlled between 40-50° C., the system was stirred and reacted for 4 hours; cooled, the temperature in reactor was lowered to 25-35° C.; the system was distilled under vacuum, the vacuum was controlled ≤−0.080 MPa, the material liquid in the reactor was distilled under vacuum to the calibration volume of 13.0 L; the temperature of the material liquid in the reactor was cooled to 15-25° C., and the system was stirred at this temperature for 1 hour; the temperature in the reactor was cooled to 0-10° C.; the temperature in the reactor was controlled between 0-10° C. and the system was stirred for 1 hour; the system was subjected to suction filtration, the filter cake was washed with acetone (2.5 kg); samples were taken and analyzed. The HPLC purity of the compound of formula I tartrate in the filter cake was 99.98%; the maximum individual impurity: 0.02%; the filter cake was dried for 24 hours at 45-55° C., under vacuum ≤−0.080 MPa; samples were taken and analyzed, acetone residue≤5000 ppm; the oven was cooled to 15-25° C.; dried and 0.74 kg of product was obtained, samples were taken and analyzed. The HPLC purity of the compound of formula I tartrate: 99.95%; the maximum individual impurity: 0.03%; the residual solvents comply with the requirements. Upon further testing, the product was crystal form O of a tartrate of a compound of formula I. Its XRPD pattern is consistent with FIG. 38.

Experimental Section

Experimental Example 1

Solubility Test 4 proportions of each of crystal form 1 of a compound of formula I, crystal form F of a phosphate of a compound of formula I and crystal form O of a tartrate of a compound of formula I with suitable amounts were weighed and each placed into a 4 mL transparent glass bottle, 1 mL of water, simulated gastric fluid (SGF), fasted-state simulated intestinal fluid (FaSSIF) and fed-state simulated intestinal fluid (FeSSIF) were added respectively to obtain sample suspension and the suspension was transferred to a shaker quickly (37° C., 200 rpm) and was shaked. The samples were observed 5 minutes later, a quantity of sample or medium was supplemented to obtain mild suspension, and sampling was conduct at 30 minutes, 2 hour, 4 hours and 24 hours, respectively. The samples were centrifuged for 10 minutes at 12000 rpm to obtain the supernatant, the supernatant was diluted appropriately and was subjected to high performance liquid chromatography. See Table 20 for chromatographic conditions.

TABLE 20

High performance liquid chromatographic conditions of the solubility test

| | | | |
|---|---|---|---|
| Instrument | Agilent 1200 DAD HPLC system | | |
| Chromatographic olumn | Waters XBridge Shield RP18 4.6 × 150 mm, 3.5 μm | | |
| Mobile phase | A: 0.1% trifluoroacetic acid solution B: 0.1% trifluoroacetic acid in acetonitrile | | |
| Column temperature | 30° C. | | |
| Detector | DAD | | |
| Detection wavelength | 230 nm | | |
| Injection volume | 5 μL | | |
| Column flow rate | 1.0 mL/min | | |
| Run time | 15 min | | |
| Collection time | 15 min | | |
| Elution procedure | Time (min) | A (%) | B (%) |
| | 0.0 | 95 | 5 |
| | 7.0 | 65 | 35 |
| | 10.0 | 5 | 95 |
| | 10.1 | 95 | 5 |
| | 15 | 95 | 5 |

The sample concentration was calculated with an external standard method. The test results are shown in Table 21.

The results showed that crystal form F of a phosphate of a compound of formula I and crystal form O of a tartrate of a compound of formula I can significantly improve the solubility of the compound in water, SGF, and FaSSIF. The solubilities of crystal form F of a phosphate of a compound of formula I in water, SGF, FaSSIF and FeSSIF at 24-hour time point were 27, 10, 60 and 1 time that of the compound of formula I, respectively; the solubilities of crystal form O of a tartrate of a compound of formula I in water, SGF, FaSSIF and FeSSIF at 24-hour time point were 9, 2, 7 and 1 time that of the compound of formula I, respectively.

Experimental Example 2

Stability Test 1

About 1 mg of crystal form 1 of a compound of formula I, crystal form F of a phosphate of a compound of formula I and crystal form O of a tartrate of a compound of formula I samples were weighed and each was placed into a 20 mL transparent glass bottle respectively, and each sample was placed to a stability chamber in accelerated conditions (40° C./75% RH, open) and at a high temperature (60° C., sealed). For the open samples, the bottle cap was removed and the bottle neck was coverred with an aluminium-foil paper stabbed with pinholes to avoid cross contamination; for the closed samples, the bottled were coverred and sealed tightly. Samples were taken at weeks 1 and 2, respectively, the samples were diluted with a diluent (methanol/water (1/1) (v/v)), the liquid phase was injected according to the chromatographic conditions in Table 22 and the sample purities were determined.

TABLE 21

Results of solubilities of crystal form 1 of a compound of formula I, crystal form F of a phosphate of a compound of formula I and crystal form O of a tartrate of a compound of formula I in water, SGF, FaSSIF, and FeSSIF at different time points

| | | Solubility (based ona compound of formula I, mg/mL) | | | |
|---|---|---|---|---|---|
| Sample | Medium | 30 min | 2 h | 4 h | 24 h |
| Crystal form 1 of a compound of formula I | Water | 1.35 | 1.73 | 1.49 | 1.43 |
| | Simulated gastric fluid (SGF) | 16.40 | 16.96 | 15.17 | 16.41 |
| | Fasted-state simulated intestinal fluid (FaSSIF) | 2.59 | 1.86 | 1.81 | 1.56 |
| | Fed-state simulated intestinal fluid (FeSSIF) | 2.91 | 2.20 | 2.61 | 3.29 |
| Crystal form F of a phosphate of a compound of formula I | Water | 35.73 | 35.14 | 36.32 | 39.53 |
| | Simulated gastric fluid (SGF) | 155.84 | 176.85 | 148.76 | 174.35 |
| | Fasted-state simulated intestinal fluid (FaSSIF) | 57.23 | 79.34 | 85.21 | 93.28 |
| | Fed-state simulated intestinal fluid (FeSSIF) | 4.22 | 3.89 | 3.56 | 3.64 |
| Cyrstal form O of a tartrate of a compound of formula I | Water | 12.53 | 12.11 | 12.13 | 12.97 |
| | Simulated gastric fluid (SGF) | 31.18 | 29.85 | 33.21 | 30.22 |
| | Fasted-state simulated intestinal fluid (FaSSIF) | 9.95 | 10.03 | 10.24 | 11.36 |
| | Fed-state simulated intestinal fluid (FeSSIF) | 4.28 | 4.31 | 4.41 | 3.98 |

Table 22 High performance liquid chromatographic conditions in the solid state stability test

| Instrument | Agilent 1200 DAD HPLC system | | |
|---|---|---|---|
| Chromatographic column | WATERS Xbridge C18 250 × 4.6 mm 5 μm | | |
| Mobile phase | A: 20 mM dipotassium phosphate solution; B: methanol | | |
| Column temperature | 40° C. | | |
| Detector | DAD | | |
| Detection wavelength | 220 nm | | |
| Injection volume | 5.0 μL | | |
| Column flow rate | 1.0 mL/min | | |
| Run time | 35 min | | |
| Post run time | 42 min | | |
| Sample concentration | 0.5 mg/mL | | |
| Elution procedure | Time (min) | A (%) | B (%) |
| | 0 | 95 | 5 |
| | 30 | 25 | 75 |
| | 35 | 25 | 75 |

The sample purities were calculated with an area normalization method. The test results are shown in Table 23.

TABLE 23

Results of short-term solid state stabilities of crystal form 1 of a compound of formula I, crystal form F of a phosphate of a compound of formula I and crystal form O of a tartrate of a compound of formula I

| | | Stability study (purity, Area %) | | | | | |
|---|---|---|---|---|---|---|---|
| | | 60° C. | | | 40° C./75% RH | | |
| Sample | 0 day | 1 week | 2 weeks | Crystal form | 1 week | 2 weeks | Crystal form |
| Crystal form 1 of a compound of formula I | 99.80 | 99.81 | 99.83 | Change | 99.82 | 99.82 | Change |
| Crystal form F of a phosphate of a ompound of formula I | 99.34 | 99.32 | 99.16 | Unchange | 99.33 | 99.35 | Unchange |
| Crystal form O of a tartrate of a ompound of formula I | 99.22 | 99.34 | 99.36 | Unchange | 99.31 | 99.36 | Unchange |

The results indicated that the appearances of crystal form 1 of a compound of formula I, crystal form F of a phosphate of a compound of formula I and crystal form O of a tartrate of a compound of formula I didn't change within 2 weeks and they were off-white powder. There were no significant differences in the purities and no obvious increased in impurities, indicating good chemical stabilities within 2 weeks. The XRPD and DSC tests (FIGS. 45-50) indicated that there were no significant differences in the crystal forms and the initial melting points of crystal form F of a phosphate of a compound of formula I and crystal form O of a tartrate of a compound of formula I samples compared with those on Day 0, showing good physical stability of the compound of formula I phosphate and tartrate within 2 weeks at a high temperature (60° C.) and in accelerated conditions (40° C./75% RH). The crystal form of crystal form 1 of a compound of formula I changed at a high temperature (60° C.) and in accelerated conditions (40° C./75% RH). On the basis of the characterization results of the free base before and after the DVS test, it can be seen that the stability of the crystal form of the free base was poor.

Experimental Example 3

Stability Test 2

Crystal form O of a tartrate of a compound of formula I tartrate crystal form O was tested with a suspension balance method, a heating-fast/slow cooling crystallization method, an anti-solvent method and a solution volatilization and crystallization method to investigate whether crystal transformation occurred in different solvents and test conditions, so as to further verify its thermodynamic stability.

1. Slow Solution Volatilization Method (EVA)

5 proportions (10 mg/proportion) of crystal form O of a tartrate of a compound of formula I prepared in example 55 were weighed and each was placed into a sample bottle, a suitable amount of tetrahydrofuran, ethanol, methanol, acetone and isopropanol (see Table 24 for the specific amounts) were added respectively, the bottled were subjected to ultrasonication to dissolve the samples, the obtained solution was filtered to a new sample bottle with a 0.45 μm nylon membrane, the sample bottle was opened and placed in a fuming cupboard, the solvent was evaporated naturally at room temperature (about 20-25° C.), the precipitated solid was collected. Upon testing, the obtained solid in 5 tests was crystal form O of a tartrate of a compound of formula I and their XRPD patterns are consistent with FIG. 38.

TABLE 24

Test conditions and results summary of the slow solution volatilization method

| Solvent | Total volume of solvent (mL) | Crystal form |
|---|---|---|
| Tetrahydrofuran | 1.8 | Crystal form O |
| Ethanol | 1.5 | Crystal form O |
| Methanol | 0.6 | Crystal form O |
| Acetone | 3.6 | Crystal form O |
| Isopropanol | 4.8 | Crystal form O |

2 Suspension Balance Method (Slurry)

18 proportions of crystal form O of a tartrate of a compound of formula I samples, each with a suitable amount were weighed, then aa certain amount of tetrahydrofuran, ethanol, ethyl acetate, n-heptane, toluene, methyl tertiary-butyl ether, isopropanol, methanol and acetone (see Table 25 for the specific amounts) was added respectively to obtain two proportions of suspension sample in each solvent system, the samples were stored at room temperature and at a high temperature (50° C.) and were slurried. The sample bottles (wrapped with a tin foil paper to protect from light) in a room temperature system were placed on Labquaker rotator for rotating 360°; the samples in a high temperature system were placed in a 50° C. thermostatic shaking incubator and were slurried, part of the suspension samples were taken on days 3, 7 and 14, respectively and were centrifuged, solid residue was collected, the solvents were volatilized at room temperature (20-25° C.) to dryness, the solid was collected. Upon testing, the obtained solid was crystal form O of a tartrate of a compound of formula I and their XRPD pattern are consistent with FIG. 38.

TABLE 25

Test conditions and results summary of the suspension balance method

| Mass of crystal form O of a tartrate of a compound of formula I (mg) | Solvent | Total volume of solvent (mL) | Crystal form |
|---|---|---|---|
| 34.5 | Tetrahydrofuran | 1 | Crystal form O |
| 28.1 | Ethanol | 1 | Crystal form O |
| 23.1 | Ethyl acetate | 1 | Crystal form O |
| 22.4 | N-heptane | 1 | Crystal form O |
| 20.0 | Toluene | 1 | Crystal form O |
| 20.3 | Methyl tert-butyl ether | 1 | Crystal form O |
| 30.1 | Isopropanol | 1 | Crystal form O |
| 50.6 | Methanol | 0.5 | Crystal form O |
| 28.9 | Acetone | 1 | Crystal form O |

3. Anti-Solvent Method (Anti-Solvent)

21 proportions of crystal form O of a tartrate of a compound of formula I samples were weighed, a certain volume of good solvents in Table 26 were added sequentially, the systems were subjected ultrasonication to dissolve, the obtained solutions were filtered with a 0.45 μm nylon membrane to a new sample bottle, different anti-solvents were slowly added dropwise to each sample bottle under magnetic stirring, the solvent system wherein solid was precipitated was centrifuged, the solid was collected, the solvent was volatilized at room temperature (20-25° C.) to dryness; the solvent system wherein no solids were precipitated was stirred for 48 hours. If no solid was precipitated, the system was stirred with the bottle opened until solid was precipitated. Upon testing, the obtained solid was crystal form O of a tartrate of a compound of formula I and their XRPD patterns are consistent with FIG. 38.

TABLE 26

Test conditions and results summary of the anti-solvent method

| Anti-solvent | Good solvent | Volume ratio (mL:mL) (Anti-solvent/good solvent) | Product crystal form |
|---|---|---|---|
| N-heptane | Tetrahydrofuran | 10/2.2 | Crystal form O |
|  | Ethanol | 8.5/1.7 |  |
|  | Isopropanol | 16.8/4.2 |  |
|  | Methanol | 5/0.5 |  |
|  | Acetone | 8/4 |  |
| Toluene | Tetrahydrofuran | 20/2.2 | Crystal form O |
|  | Ethanol | 8.5/1.8 |  |
|  | Isopropanol | 25.2/4.2 |  |
|  | Methanol | 5/0.5 |  |
|  | Acetone | 24/4 |  |
| Methyl tert-butyl ether | Tetrahydrofuran | 20/2.2 | Crystal form O |
|  | Ethanol | 17/1.8 |  |
|  | Isopropanol | 25.2/4.2 |  |
|  | Methanol | 5/0.5 |  |
|  | Acetone | 24/4 |  |
| Ethyl acetate | Tetrahydrofuran | 20/2.3 | Crystal form O |
|  | Ethanol | 17/1.7 |  |
|  | Isopropanol | 25.2/4.2 |  |
|  | Methanol | 5/0.5 |  |
|  | Acetone | 24/4 |  |

5. Solution Heating-Fast Cooling Method (HFC)

5 proportions (about 20 mg/proportion) of crystal form O of a tartrate of a compound of formula I samples were weighed and placed into sample bottles, a suitable amount of tetrahydrofuran, acetone, ethanol, isopropanol and methanol (see Table 27 for the specific amounts) was added respectively, the sample bottles were placed on a magnetic heating stirrer, heated to dissolve in a water bath at about 50° C. at 200 rpm. The temperature was maintained for 15 minutes, the solution was filtered with a 0.45 μm membrane when hot and was transferred to new sample bottles, the bottled were immediately transferred to a −20° C. refrigerator overnight, the solvent systems wherein solid was precipitated were centrifuged and the solid was collected, the solvent was volatilized at room temperature (20-25° C.) to dryness; the solvent systems wherein no solid was precipitated were placed to a −20° C. refrigerator until a large amount of solids precipitated. In the tetrahydrofuran and acetone systems, solid didn't precipitate all the time. Upon testing, the obtained solid obtained from ethanol, isopropanol and methanol systems was crystal form O of a tartrate of a compound of formula I and their XRPD spectra were consistent with FIG. 38.

TABLE 27

Test conditions and results summary of the solution heating-fast cooling method

| Solvent | Volume of solvent (mL) | Crystal form |
|---|---|---|
| Tetrahydrofuran | 1.5 | / |
| Acetone | 2.0 | / |
| Ethanol | 0.8 | Crystal form O |
| Isopropanol | 2.0 | Crystal form O |
| Methanol | 0.3 | Crystal form O |

6. Solution Heating-Slow Cooling Method (HSC)

5 proportions (about 20 mg/proportion) of crystal form O of a tartrate of a compound of formula I samples were weighed and placed in sample bottles, a suitable amount of tetrahydrofuran, acetone, ethanol, isopropanol and methanol (see Table 28 for the specific amounts) was added respectively, the sample bottles were placed on a magnetic heating stirrer, heated to dissolve in a water bath at about 50° C. at 200 rpm. The temperature was maintained for 15 minutes, the solution was filterred with a 0.45 μm membrane when hot and transferred to new sample bottles, slowly cooled to room temperature at 6° C./h overnight, the sample bottles were placed in a refrigerator (2-8° C.), the solvent systems wherein solid precipitated were centrifuged and the solid was collected, the solvent was volatilized at room temperature (20-25° C.) to dryness; the solvent systems wherein no solid precipitated were placed in a −20° C. refrigerator until a large amount of solids precipitated. In the tetrahydrofuran, acetone and methanol systems, solids didn't precipitate all the time. Upon testing, the obtained solid obtained from the ethanol and isopropanol systems was crystal form O of a tartrate of a compound of formula I and their XRPD pattern were consistent with FIG. 38.

TABLE 28

Test conditions and results summary of the solution heating-fast cooling method

| Solvent | Volume of solvent (ml) | Crystal form |
|---|---|---|
| Tetrahydrofuran | 1.5 | / |
| Methanol | 0.3 | / |
| Acetone | 2.0 | / |
| Ethanol | 0.8 | Crystal form O |
| Isopropanol | 2.0 | Crystal form O |

The above test results indicated that after processing crystal form O of a tartrate of a compound of formula I with different methods including suspension balance, heating-fast/slow cooling crystallization, anti-solvent and solution volatilization and crystallization methods, the products were still the single crystal form O. Crystal form O of a tartrate of a compound of formula I is a thermally stable preponderant crystal form.

Test 4: TYK2 Biochemical Test

A suitable amount of a compound of formula I was weighed for TYK2 biochemical test.

The test was conducted by Reaction Biology Corp, Malvern, PA (Anastassiadis et al. Nat Biotechnol. 2011; 29(11):1039-45). The steps are briefly described as follows.

Reagents:

Basic reaction buffer: 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT and 1% DMSO. The required cofactors were added to each kinase reaction.

Reaction Steps:

1. Preparing the designated substrate in the newly prepared basic reaction buffer;
2. Transferring the required cofactor to the above matrix solution;
3. Transferring the designated kinase to the substrate solution and mixing well slightly;
4. Transferring a compound of formula I in DMSO to a kinase reaction mixture with Acoustic technique (Echo550; nanoliter range), culturing for 20 minutes at room temperature;
5. Introducing $^{33}$P-ATP (specific activity: 10 μCi/μl) to the reaction mixture to trigger a reaction;
6. Culturing at room temperature and conducting a kinase reaction for 2 hours;
7. Plotting the reaction on P81 ion exchange paper;
8. Testing the kinase activity with a filter binding assay.

The test results indicated that a compound of formula I was also a potent TYK2 inhibitor and its $IC_{50}$ was less than 10 nM.

A person skilled in the art can understand and make some modifications or changes to the invention under the instruction of the present description. These modifications and changes should be in the scope specified in the claims of the invention.

The invention claimed is:

1. Crystal form O of a tartrate of a compound of formula I

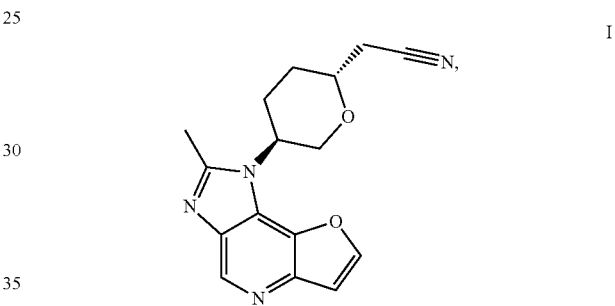

wherein the X-ray powder diffraction pattern of the crystal form shows characteristic peaks at 2theta angles of 6.3°±0.2°, 26.1°±0.2° and 26.9°±0.2°.

2. The crystal form O of a tartrate of a compound of formula I according to claim 1, wherein the X-ray powder diffraction pattern of the crystal form shows characteristic peaks at 2theta angles of 6.3°±0.2°, 12.5°±0.2°, 15.1°±0.2°, 26.1°±0.2°, 26.9°±0.2° and 27.5°±0.2°.

3. The crystal form O of a tartrate of a compound of formula I according to claim 1, wherein the X-ray powder diffraction pattern of the crystal form shows characteristic peaks at 2theta angles of 6.3°±0.2°, 11.4°±0.2°, 12.5°±0.2°, 14.1°±0.2°, 14.4°±0.2°, 15.1°±0.2°, 26.1°±0.2°, 26.9°±0.2° and 27.5°±0.2°.

* * * * *